US008885038B2

(12) United States Patent
Kawada et al.

(10) Patent No.: US 8,885,038 B2
(45) Date of Patent: Nov. 11, 2014

(54) MEASURING APPARATUS AND MEASURING METHOD THEREOF, APPARATUS FOR CORRECTING PROCESSING POSITION OF CUTTING MACHINE AND METHOD THEREOF FOR CORRECTING PROCESSING POSITION, AND IMAGING APPARATUS AND CUTTING MACHINE COMPRISING THE SAME

(75) Inventors: Tosuke Kawada, Chiryu (JP); Masaki Kato, Chiryu (JP); Shinji Ichino, Nagoya (JP)

(73) Assignee: Fuji Machine Mfg. Co., Ltd., Chiryu-shi (JP)

( * ) Notice: Subject to any disclaimer, the term of this patent is extended or adjusted under 35 U.S.C. 154(b) by 418 days.

(21) Appl. No.: 13/266,006
(22) PCT Filed: Apr. 20, 2010
(86) PCT No.: PCT/JP2010/056995
§ 371 (c)(1),
(2), (4) Date: Oct. 24, 2011
(87) PCT Pub. No.: WO2010/125947
PCT Pub. Date: Nov. 4, 2010

(65) Prior Publication Data
US 2012/0038763 A1 Feb. 16, 2012

(30) Foreign Application Priority Data
Apr. 28, 2009 (JP) ................................. 2009-109909

(51) Int. Cl.
| H04N 7/18 | (2006.01) |
| G01K 5/50 | (2006.01) |
| B23Q 17/20 | (2006.01) |
| B23Q 17/24 | (2006.01) |
| B23Q 11/00 | (2006.01) |
| B23Q 17/09 | (2006.01) |
| B23B 25/06 | (2006.01) |
| G01N 21/86 | (2006.01) |

(52) U.S. Cl.
CPC . *B23B 25/06* (2013.01); *G01K 5/50* (2013.01); *B23Q 17/20* (2013.01); *G01N 21/86* (2013.01); *B23Q 17/2495* (2013.01); *B23Q 11/0003* (2013.01); *B23Q 17/09* (2013.01); *G01K 2217/00* (2013.01); *B23Q 17/0928* (2013.01); *H04N 7/18* (2013.01)
USPC ............................................. 348/95; 250/561

(58) Field of Classification Search
CPC ................................. H04N 7/18; G01N 21/86
See application file for complete search history.

(56) References Cited

U.S. PATENT DOCUMENTS 4,220,977 A * 9/1980 Yamanaka ..................... 348/265
4,928,019 A * 5/1990 Tomikawa et al. ......... 250/559.3
(Continued)

FOREIGN PATENT DOCUMENTS

DE 3620118 A1 * 12/1987
EP 1 130 372 A1 9/2001
(Continued)

*Primary Examiner* — Jorge L Ortiz Criado
*Assistant Examiner* — Paul Myers, III
(74) *Attorney, Agent, or Firm* — Foley & Lardner LLP

(57) ABSTRACT

Provided is an apparatus and a method thereof which can detect a displacement amount of a cutting tool with respect to a workpiece with high accuracy and can correct a processing position with high accuracy. Accordingly, a turret gauge 46 is comprised of an invar body 47 and a gauge main body 48 with a different thermal expansion coefficient. A point A of the gauge main body 48 and a leading edge 47A of the invar body are imaged in a state of viewing the whole thereof at a time of an initialization and a calibration cycle (CS), and a temperature of the gauge main body 48 is detected by comparing each image data. Furthermore, the length between the point A and a point B of the gauge main body 48 at the time of the CS is obtained based on the image data. The actual length is compared with a theoretical length between the point A and the point B at a temperature of the gauge main body 48 at the time of the CS, and consideration is given to the comparison. Therefore, a heat displacement amount of a ball screw can be accurately detected, the displacement of a processing position of a cutting tool can be corrected with high accuracy, and processing accuracy of a workpiece can be improved.

14 Claims, 41 Drawing Sheets

(56) References Cited

U.S. PATENT DOCUMENTS

| | | | | |
|---|---|---|---|---|
| 5,301,003 | A * | 4/1994 | Ikeda | 356/73 |
| 6,089,750 | A | 7/2000 | Murakami et al. | |
| 7,405,388 | B2 * | 7/2008 | Reilley | 250/221 |
| 7,848,022 | B2 | 12/2010 | Hayata | |
| 8,180,477 | B2 * | 5/2012 | Mori et al. | 700/160 |
| 2003/0059103 | A1 * | 3/2003 | Shiomi et al. | 382/144 |
| 2008/0193120 | A1 * | 8/2008 | Nishimoto et al. | 396/280 |
| 2009/0124028 | A1 | 5/2009 | Hayata | |
| 2010/0118137 | A1 * | 5/2010 | Avila et al. | 348/125 |

FOREIGN PATENT DOCUMENTS

| | | | |
|---|---|---|---|
| JP | 04-353751 | A | 12/1992 |
| JP | 05-133813 | A | 5/1993 |
| JP | 05-133814 | | 5/1993 |
| JP | 08-255819 | A | 10/1996 |
| JP | 09253979 | A * | 9/1997 |
| JP | 10-096616 | A | 4/1998 |
| JP | 11-099449 | A | 4/1999 |
| JP | 2000-012442 | A | 1/2000 |
| JP | 2001-269844 | | 10/2001 |
| JP | 2005-215295 | A | 8/2005 |
| JP | 2006-010445 | A | 1/2006 |
| JP | 2007-294727 | A | 11/2007 |
| JP | 2008-306039 | A | 12/2008 |
| JP | 2009-061565 | A | 3/2009 |
| WO | WO 87/07550 | A1 | 12/1987 |
| WO | WO 2009/125577 | A1 | 10/2009 |

* cited by examiner

MEASURING APPARATUS AND MEASURING METHOD THEREOF, APPARATUS FOR CORRECTING PROCESSING POSITION OF CUTTING MACHINE AND METHOD THEREOF FOR CORRECTING PROCESSING POSITION, AND IMAGING APPARATUS AND CUTTING MACHINE COMPRISING THE SAME

TECHNICAL FIELD

The present invention relates to a measuring apparatus for measuring a displacement amount of a cutting tool by processing an image of an object to be measured, such as a cutting tool, and a measuring method thereof, and to an apparatus for correcting a processing position of a cutting machine and a method thereof for correcting the processing position. Furthermore, the present invention constitutes a part of the above-mentioned apparatus for correcting a processing position, and relates to an imaging apparatus for respectively imaging a plurality of subjects at substantially the same time, and a cutting machine for detecting a state of a cutting tool by imaging the cutting tool or the like by the said imaging apparatus.

BACKGROUND ART

For example, Patent Literature 1 discloses a measuring apparatus for measuring an expansion coefficient or the like of a sample whose expansion coefficient or contraction coefficient is unclear, based on an amount of change of the sample at a predetermined temperature. This measuring apparatus sets a temperature of a sample to be a predetermined temperature, and measures the expansion coefficient or the like of the above-mentioned sample based on image data in a transmitted light quantity of a lens positioned at a predetermined position.

Furthermore, Patent Literature 2 describes a tool observing method comprising imaging, using a camera, a cutting tool such as a tool bit (hereinafter, also referred to as tool) for cutting a workpiece which is an object to be processed, and observing the tool for any breakage, wear or the like based on image data thereof, wherein at least either before or after processing the object to be processed, a tool is rotated or moved so as to capture multiple pieces of image data thereof, and the tool is observed for any breakage, wear or the like using image data in focus which is selected from the multiple pieces of image data. Furthermore, Patent Literature 3 discloses a system for automatically inspecting a tool chip of a machine tool for any wear or the like using a visual sensor. This system illuminates a slit on a chip from an illuminating window of a structure light unit, and shoots with a camera through an imaging window, thereby automatically inspecting the tool chip for any wear or the like.

PRIOR ART DOCUMENT

Patent Document

Patent Document 1: JPA-04-353751
Patent Document 2: JPA-2001-269844
Patent Document 3: JPA-10-96616

SUMMARY OF THE INVENTION

Problem to be Solved by the Invention

Patent Literature 1 is an apparatus for measuring an expansion coefficient or contraction coefficient of a sample, and not for measuring a temperature of the sample. Furthermore, it would be difficult, for even an apparatus for observing a tool by processing an image of a tip of the tool using a camera, as described in Patent Literature 2 and Patent Literature 3, to maintain accuracy against a heat displacement or the like of a camera itself and a camera holding bracket. In other words, even when the camera slightly inclines, a measurement error thereof is geometrically magnified in accordance with a distance between the camera and a tool to be detected, and thereby measurement accuracy is decreased. Therefore, when the conventional technique described in the above-mentioned Patent Literature 2 is applied to a cutting machine, it has been difficult to measure with high accuracy a wear amount or a displacement amount of a tool bit with respect to a workpiece, which is an original purpose.

In addition, there are an inner diameter tool bit and an outer diameter tool bit available as a cutting tool; however, it is difficult to image these tool bits at the same position. More specifically, the directions of chips in an inner diameter tool bit and an outer diameter tool bit are precisely opposite to each other, and thus it is necessary to arrange reference gauges of the inner diameter tool bit and the outer diameter tool bit, which check if each tool bit is at a reference position, respectively on, for example, a chuck, and also to move each tool bit to an imaging position of including and imaging (hereinafter, also referred to as viewing the whole) the reference gauges and the chips of the tool bit in an imaging area of a camera. Therefore, problems would occur, such as that a mechanism for viewing the whole of the reference gauges and the chips becomes complex. Meanwhile, Patent Literature 2 and Patent Literature 3 have no configuration that enables imaging or the like of different types of tool bits. It should be noted that Patent Literature 2 has a complex configuration as it performs imaging using a plurality of cameras.

The present invention provides a measuring apparatus which can accurately measure a temperature of an object to be measured, and a measuring method thereof, as well as an apparatus for correcting a processing position of a cutting machine, which can detect a displacement amount of a cutting tool with respect to a workpiece with high accuracy and can correct the processing position with high accuracy, and a method thereof for correcting the processing position. In addition, it is an object of the present invention to provide an imaging apparatus which can image a subject at different imaging positions at substantially the same time, and a cutting machine which can detect a state of a cutting tool by imaging the cutting tool or the like by this imaging apparatus.

Means for Solving the Problem

A measuring apparatus according to the present invention comprises: a reference body which is a reference of a heat displacement amount of a heat-displaced object to be measured; an imaging means for imaging the reference body and the object to be measured in a same imaging area; a recording means for recording reference image data at a reference temperature generated by the imaging means; a collating means for collating the reference image data, which has been recorded in advance in the recording means, with measured image data at a time of an arbitrary measurement, which is generated by the imaging means; and a calculating means for calculating a temperature of the object to be measured at the time of the arbitrary measurement based on a collation result by the collating means. Furthermore, a measuring method according to the present invention images, as a subject, a reference body which is a reference of a heat displacement amount of a heat-displaced object to be measured in a same imaging area in an imaging means; collates reference image data at a reference temperature, which has been recorded in advance in a recording means, with measured image data at a time of an arbitrary measurement by a collating means; and measures a temperature of the object to be measured at the time of the arbitrary measurement based on a collation result by the collating means.

An apparatus for correcting a processing position of a cutting machine according to the present invention comprises: an imaging means for imaging a subject; a reference gauge (arranged on a chuck for holding a workpiece) for measuring a position error of the imaging means; a reference means, which is arranged on a mounting table on which a cutting tool is to be mounted, for detecting a displacement amount of a (displaced or deficient) cutting tool and a temperature of the mounting table; a recording means for recording reference image data at a reference temperature, in which the reference gauge and the reference means corresponding to the reference gauge are imaged as a subject in a same imaging area by the imaging means; a collating means for collating the reference image data, which has been recorded in advance in the recording means, with measured image data at a time of an arbitrary measurement of the subject, which is generated by the imaging means; and a correcting means for correcting a processing position of the cutting tool based on a collation result by the collating means. The method for correcting a processing position thereof establishes correspondence between a reference gauge (arranged on a chuck) for measuring a position error of an imaging means, and a reference means which is arranged on a mounting table in order to detect a displacement amount of a (displaced or deficient) cutting tool and a temperature of the mounting table of the cutting tool; images, as a subject of the imaging means, the corresponding reference gauge and the corresponding reference means in a same imaging area in the imaging means; collates reference image data at a reference temperature, which has been recorded in advance in a recording means, with measured image data at a time of an arbitrary measurement by a collating means; and corrects a processing position of the cutting tool based on a collation result by the collating means. The thus-configured reference means may comprise: a mounting means which has an identical quality of material to that of a metal constituting the mounting table and has a reference section; and a reference body which has a free end fixed to only one end thereof and corresponding to the reference section, and which is a reference of a heat displacement amount of the mounting means. In addition, the thus-configured mounting means may comprise at least two or more of measurement base points. Furthermore, the thus-configured reference body may be formed with a material with a different thermal expansion coefficient from that of the metal constituting the mounting table, such as a material with a smaller coefficient or with a larger coefficient. Moreover, the thus-configured reference body may be a bimetal body.

Furthermore, an apparatus for correcting a processing position of a cutting machine according to the present invention comprises: an imaging means for imaging a subject; a reference gauge which is arranged on a chuck for holding a workpiece in order to measure a position error of the imaging means; a reference body which is arranged in such a manner that one end is fixed to the chuck and that a free end corresponds to the reference gauge, and which is a reference of a heat displacement amount of the reference gauge; a recording means for recording reference image data at a reference temperature, which is obtained by imaging, as a subject, the reference gauge and the free end of the reference body corresponding to the reference gauge in a same imaging area by the imaging means; a collating means for collating the reference image data, which has been recorded in advance in the recording means, with measured image data at a time of an arbitrary measurement of the subject, which is generated by the imaging means; and a correcting means for correcting a processing position of a cutting tool based on a collation result by the collating means. The thus-configured reference body may be made of a material with a different thermal expansion coefficient from that of the material holding the reference gauge. In addition, the thus-configured reference body may be a bimetal body. The said method for correcting a processing position thereof establishes correspondence between a reference gauge which is arranged on a chuck for holding a workpiece in order to measure a position error of an imaging means, and a reference body which is a reference of a heat displacement amount of the reference gauge and which is arranged in such a manner that one end is fixed to the chuck and that a free end corresponds to the reference gauge; images, as a subject of the imaging means, the corresponding reference gauge and the corresponding free end of the reference body in a same imaging area in the imaging means; collates reference image data at a reference temperature, which has been recorded in advance in a recording means, with measured image data at a time of an arbitrary measurement by a collating means; and corrects a processing position of a cutting tool based on a collation result by the collating means. More specifically, the present invention is a measuring apparatus and an apparatus for correcting a processing position of a cutting machine which is provided with the measuring apparatus, as well as a measuring method and a method for correcting a processing position of a cutting machine which uses the measuring method.

Furthermore, an imaging apparatus according to the present invention comprises: an optical path separating means for separating an optical path respectively corresponding to a subject at a different imaging position; and an image pickup device which is arranged on a same optical path in the optical path separating means, wherein the optical path separating means blocks an optical path at one imaging position, when imaging the subject at the other imaging position. In this case, one of the optical path separating means may be a half mirror, and the other may be a full mirror. In addition, a shutter for opening the optical path corresponding to the optical path separating means at the time of imaging may be further provided. Furthermore, the imaging apparatus according to the present invention may fold an optical path back to the half mirror so as to be of the same length as that of an optical path of the full mirror. In addition, a mirror chamber for housing the image pickup device and the mirror, and a shutter chamber for preventing air from flowing into the mirror chamber at a time of opening the shutter may be provided, so that air may be supplied from the mirror chamber to the shutter chamber. In addition, an imaging apparatus according to the present invention may be configured so as to arrange a plurality of image pickup devices on an optical path respectively corresponding to a subject at a different imaging position.

A cutting machine which comprises the imaging apparatus according to the present invention images a subject at a different imaging position with a time difference in switching an optical path by any one of the above-mentioned imaging apparatuses. Furthermore, a cutting machine comprising the imaging apparatus according to the present invention comprises: any one of the above-mentioned imaging apparatuses; a reference gauge which is arranged on a chuck for holding a workpiece in order to measure a position error of the imaging means; and a reference body which is arranged in such a manner that one end is fixed to the chuck and that a free end corresponds to the reference gauge, and which is a reference of a heat displacement amount of the reference gauge, wherein the imaging apparatus images, as a subject, the reference gauge and the free end of the reference body corresponding to the reference gauge, at one imaging position in the one optical path, and a cutting tool at the one imaging position, in a same imaging area; or images, as a subject, the reference gauge and the free end of the reference body corresponding to the reference gauge, at the one imaging position in the one optical path, in a same imaging area, and images a cutting tool at the other imaging position in the other optical path with a time difference in switching an optical path.

Furthermore, a cutting machine comprising an imaging apparatus according to the present invention comprises: anyone of the above-mentioned imaging apparatuses; a reference gauge for measuring a position error of the imaging means; and a reference means which is arranged on a mounting table where a cutting tool is to be mounted, for detecting a displacement amount of a cutting tool and a temperature of the mounting table, wherein the imaging apparatus uses the reference gauge at the one imaging position in the one optical path as a subject, and the reference means corresponding to the reference gauge or a cutting tool at the other imaging position in the other optical path as a subject; and images the reference gauge at one imaging position in the one optical path, and images the reference means or the cutting tool at the other imaging position in the other optical path with a time difference in switching an optical path.

Effects of the Invention

The measuring apparatus and the measuring method thereof according to the present invention image, as a subject, a reference body which is a reference of a heat displacement amount of a heat-displaced object to be measured in a same imaging area in an imaging means, collates reference image data at a reference temperature, which has been recorded in advance in a recording means, with measured image data at a time of an arbitrary measurement by a collating means, and measures a temperature of the object to be measured at a time of an arbitrary measurement based on a collation result by the collating means, and therefore can accurately measure the temperature of the object to be measured. In addition, the temperature of the object to be measured can be measured from a distant point in a noncontact state without any connection by wiring or the like, so that the need of a member for a wiring connection, for example, a brush holder can be eliminated, and that the configuration of measuring apparatus can be simplified.

The apparatus for correcting a processing position of a cutting machine and the method for correcting a processing position thereof according to the present invention establish correspondences between a reference gauge (arranged on a chuck) for measuring a position error of an imaging means and a reference means which is arranged on a mounting table in order to detect a displacement amount of a (displaced or deficient) cutting tool and a temperature of the mounting table of the cutting tool, images, as a subject of the imaging means, the corresponding reference gauge and the corresponding reference means in a same imaging area in the imaging means, collates reference image data at a reference temperature, which has been recorded in advance in a recording means, with measured image data at a time of an arbitrary measurement by a collating means, and corrects a processing position of the cutting tool based on a collation result by the collating means, so as to, for example at a time of not cutting during an operation, correct a processing position by calculating a temperature of a feed mechanism of a mounting table or the like (ball screw mechanism or the like) and a displacement amount of the cutting tool. Therefore, even if a processing position is displaced due to the thermal expansion/contraction of the feed mechanism during the operation, the displacement of the processing position thereof can be corrected with high accuracy, and processing accuracy of a workpiece can be improved.

Furthermore, the apparatus for correcting a processing position of a cutting machine and the method for correcting a processing position thereof according to the present invention establishes correspondence between a reference gauge which is arranged on a chuck for holding a workpiece in order to measure a position error of an imaging means, and a reference body which is a reference of a heat displacement amount of the reference gauge, and which is arranged in such a manner that one end is fixed to the chuck and a free end corresponds to the reference gauge, images, as a subject of the imaging means, the corresponding reference gauge and the corresponding free end of the reference body in a same imaging area in the imaging means, collates reference image data at a reference temperature, which has been recorded in advance in a recording means, with measured image data at a time of an arbitrary measurement by a collating means, and corrects a reference position of a cutting tool based on a collation result by the collating means. Therefore, even if a processing position is displaced due to the thermal expansion/contraction of the chuck, the displacement of the processing position thereof can be corrected with high accuracy, and processing accuracy of a workpiece can be improved.

Furthermore, the imaging apparatus or the cutting machine comprising this imaging apparatus according to the present invention respectively opens and closes each shutter in a time considered to be a moment (time difference in switching optical paths), so that there is no variation between positions of subjects at the time of imaging, and that subjects at different imaging positions can be imaged in a state which can be substantially considered as viewing the whole thereof. More specifically, according to the imaging apparatus or the cutting machine comprising this imaging apparatus according to the present invention, for example, five million pixels (size of 17 mm in a short side and 21.5 mm in a long side) can be effectively used as they are without reducing an imaging area of the imaging apparatus by, for example, dividing, so that image recognition can be improved. Furthermore, according to the imaging apparatus or the cutting machine comprising this imaging apparatus according to the present invention, a subject at a different imaging position, such as an inner diameter tool bit or an outer diameter tool bit, can be imaged respectively, so that a type of a tool bit, such as an inner diameter tool bit, an outer diameter tool bit or other special tool bits, can be imaged in a state which can be substantially considered as viewing the whole thereof, without separately providing, for example, a reference gauge for an inner diameter tool bit. Furthermore, according to the imaging apparatus or the cutting machine comprising this imaging apparatus according to the present invention, a subject at a different imaging position can be imaged respectively, so that for example a travel amount of the cutting tool can be reduced, and that a moving mechanism f the cutting tool can be downsized.

BRIEF DESCRIPTION OF THE DRAWINGS

FIG. 7(A) is a view illustrating a manner of obtaining edges of a chip thereof, and FIGS. 7(B) to 7(D) are views illustrating a manner of obtaining a nose of a chip;

FIG. 34(A) is an end view of the imaging apparatus, and FIG. 34(B) is a plan view of a shutter thereof;

FIG. 38(A) is an end view of the imaging apparatus, and FIG. 38(B) is a plan view of a shutter thereof;

BEST MODE FOR CARRYING OUT THE INVENTION

Hereinafter, with regard to the best mode for carrying out the present invention, embodied first to tenth embodiments will be described.

First Embodiment

Hereinafter, a measuring apparatus and an apparatus for correcting a processing position of a cutting machine which is provided with the measuring apparatus, as well as a measuring method and a method for correcting a processing position of a cutting machine which uses the measuring method, which are first embodiment of the present invention, will be described based on FIG. 1 to FIG. 13. It should be noted that a cutting machine according to first embodiment will be described as a single-spindle turret lathe (hereinafter, simply referred to as lathe) S.

(Schematic Configuration of Lathe S)

Figure 1:
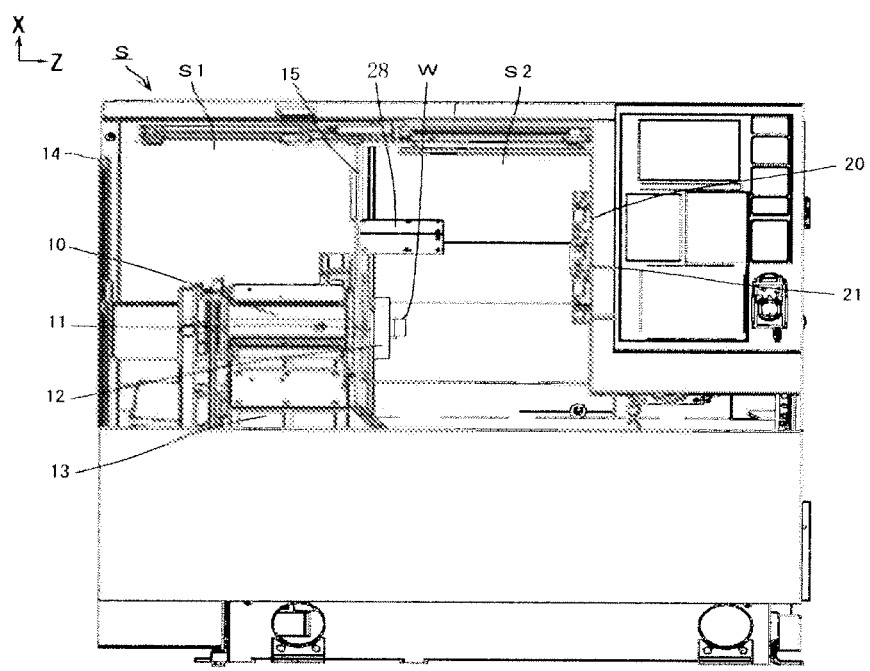
FIG. 1 is a front view illustrating a single-spindle turret lathe of first embodiment.

As illustrated in FIG. 1, in a lathe S, a headstock 10 which is fixed in such a manner that an axis line thereof is parallel to a Z-axis direction (horizontal direction), and a turret apparatus 20 which is movable in a direction parallel to the Z-axis direction and a direction parallel to an X-axis direction, which is inclined rearward at an angle of 60 with respect to a vertical direction orthogonal to the Z-axis direction, are arranged so as to face each other. In the headstock 10, a main spindle 11 is rotatably supported around an axis line parallel to the Z-axis direction. The main spindle 11 is configured so as to be rotationally driven by a main spindle driving motor (not shown). A chuck 12 for gripping a workpiece W which is an object to be processed is mounted on a tip of the main spindle 11 on the turret apparatus 20 side. The thus-configured headstock 10 and main spindle driving motor are arranged on a bed 13.

In the turret apparatus 20, a turret tool post (hereinafter, simply referred to as tool post) 21 which is a mounting table is provided around an axis line parallel to the Z-axis direction so as to be capable of rotary indexing. On the tool post 21, a plurality of cutting tools 25, 26 (see FIG. 4) are mounted equiangularly on the circumference. The thus-configured turret apparatus 20 is arranged so as to be able to slide in the X-axis direction and the Z-axis direction. It should be noted that the turret apparatus 20 moves through a ball screw mechanism (not shown) by an NC motor 52 of an NC table 50 shown in FIG. 13. More specifically, the turret apparatus 20 moves with respect to the headstock 10 fixed in place. Meanwhile, the tool post 21 is rotationally driven by a turret motor 54 shown in FIG. 13.

As illustrated in FIG. 1, in the lathe S, a cover 14 for covering the headstock 10 and the turret apparatus 20 is provided, and in the cover 14, a partition wall 15 for partitioning the headstock 10 side and the turret apparatus 20 side is provided. This partition wall 15 is provided in order for swarf or a cutting fluid flying apart not to be attached to the headstock 10 or the like when the cutting tools 25, 26 shown in FIG. 4 on the tool post 21 cut an outer periphery or an edge face or the like of the workpiece W gripped by the chuck 12. More specifically, the headstock 10 side partitioned by this partition wall 15 is an isolating zone S1, and the turret apparatus 20 side is a processing zone S2.

Figure 2:
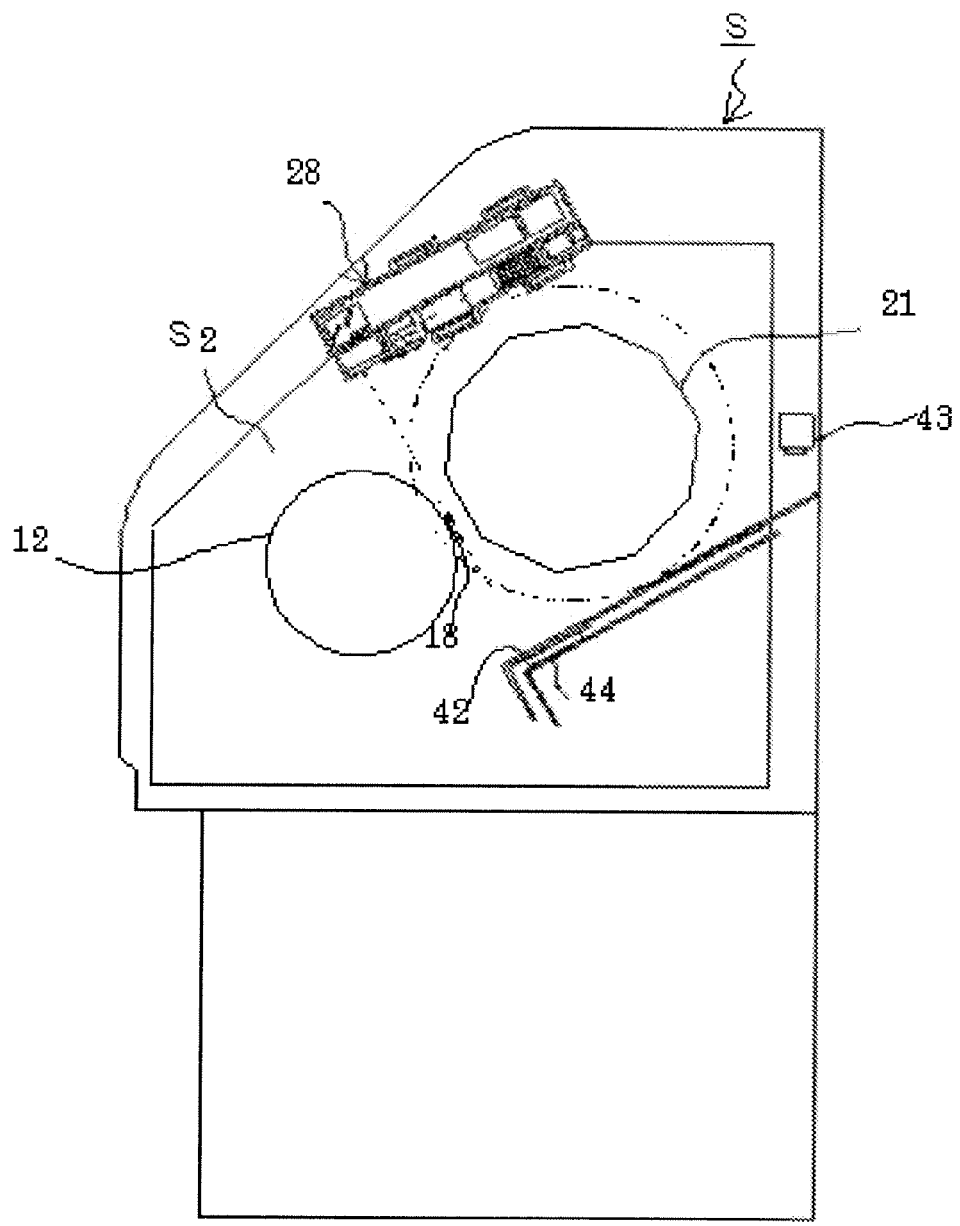
FIG. 2 is a side view illustrating a principal section of the turret lathe shown in FIG. 1.
Figure 4:
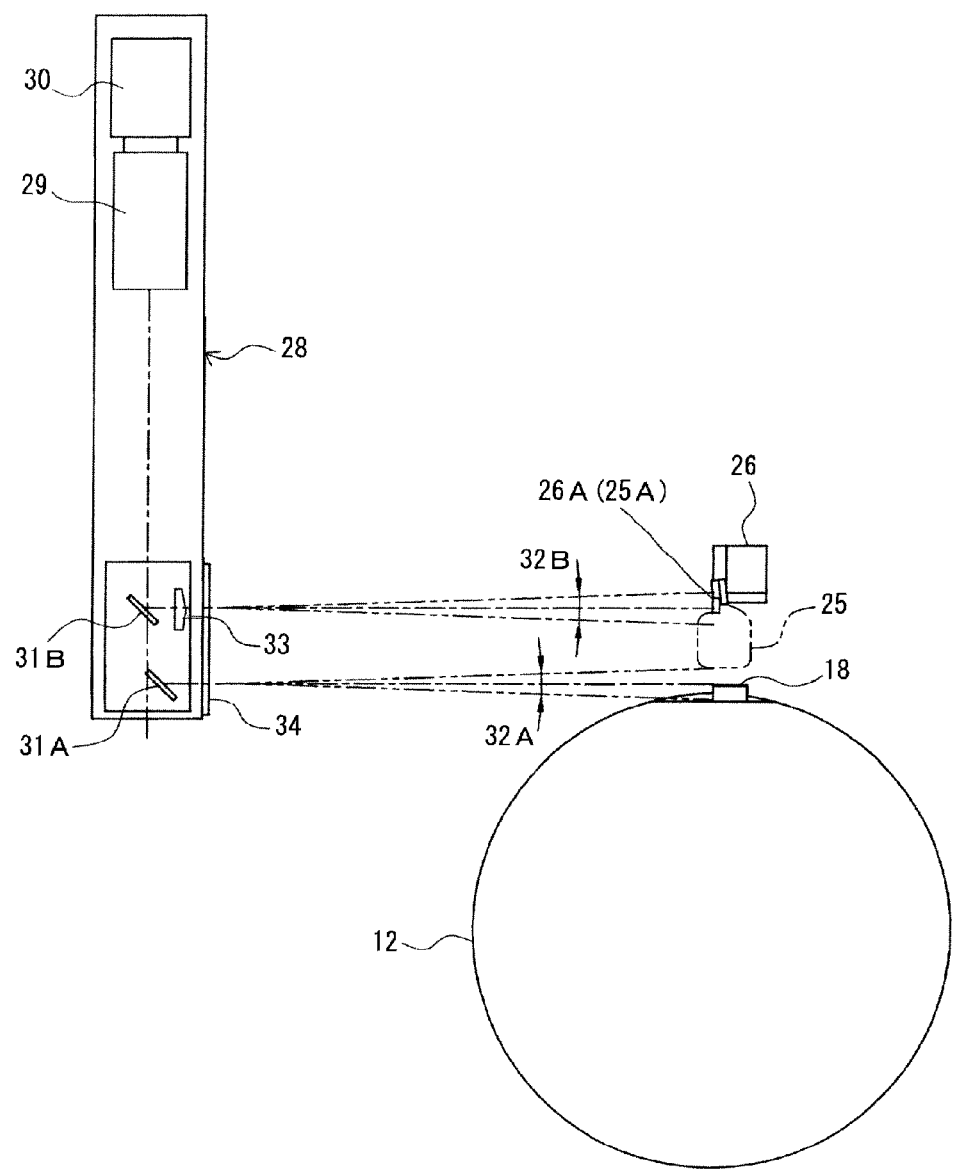
FIG. 4 is a view illustrating a positional relationship when a tool bit and a reference gauge are included in a camera view and imaged by the camera shown in FIG. 2.

The main spindle 11 is protruded to the processing zone S2 side from a hole provided on the partition wall 15, and the chuck 12 is mounted on the tip of the main spindle 11 thereof. As illustrated in FIG. 2 and FIG. 4, a reference gauge 18 which is arranged so as to be protruded from an outer periphery of the chuck 12 measures a position error of a camera apparatus 28 which is an imaging means, and is used in common for both of an inner diameter processing tool bit 25 and an outer diameter processing tool bit 26 which are cutting tools. In addition, the reference gauge 18 is formed by a heat-treated steel in order to prevent wear due to swarf or the like. This reference gauge 18 has a small amount of protrusion from an outer peripheral surface of the chuck 12, and thus a rotation range of the reference gauge 18 is small when the chuck 12 rotates. In addition, the reference gauge 18 is fixed on the chuck 12, so that alignment for imaging can be fascinated.

(Configuration of Camera Apparatus 28)

As illustrated in FIG. 1 and FIG. 2, in the lathe S, a camera apparatus 28 which is an imaging means is fixed at a predetermined position on the processing zone S2 side. This camera apparatus 28 is configured so as to image chips 25A, 26A (a cutting edge in the case of a cutting tool, except for a chip, such as a tool bit) or the like shown in, for example, FIG. 4 of the cutting tools (hereinafter, also referred to as tool bit) 25, 26, and to output the imaged image data to a CPU 60 (see FIG. 13). In addition, the CPU 60, which is a collating means, a calculating means and a correcting means, collates/calculates displacement or the like of chips 25A, 26A, and corrects a processing position of a cutting tool based on those results.

Figure 3:
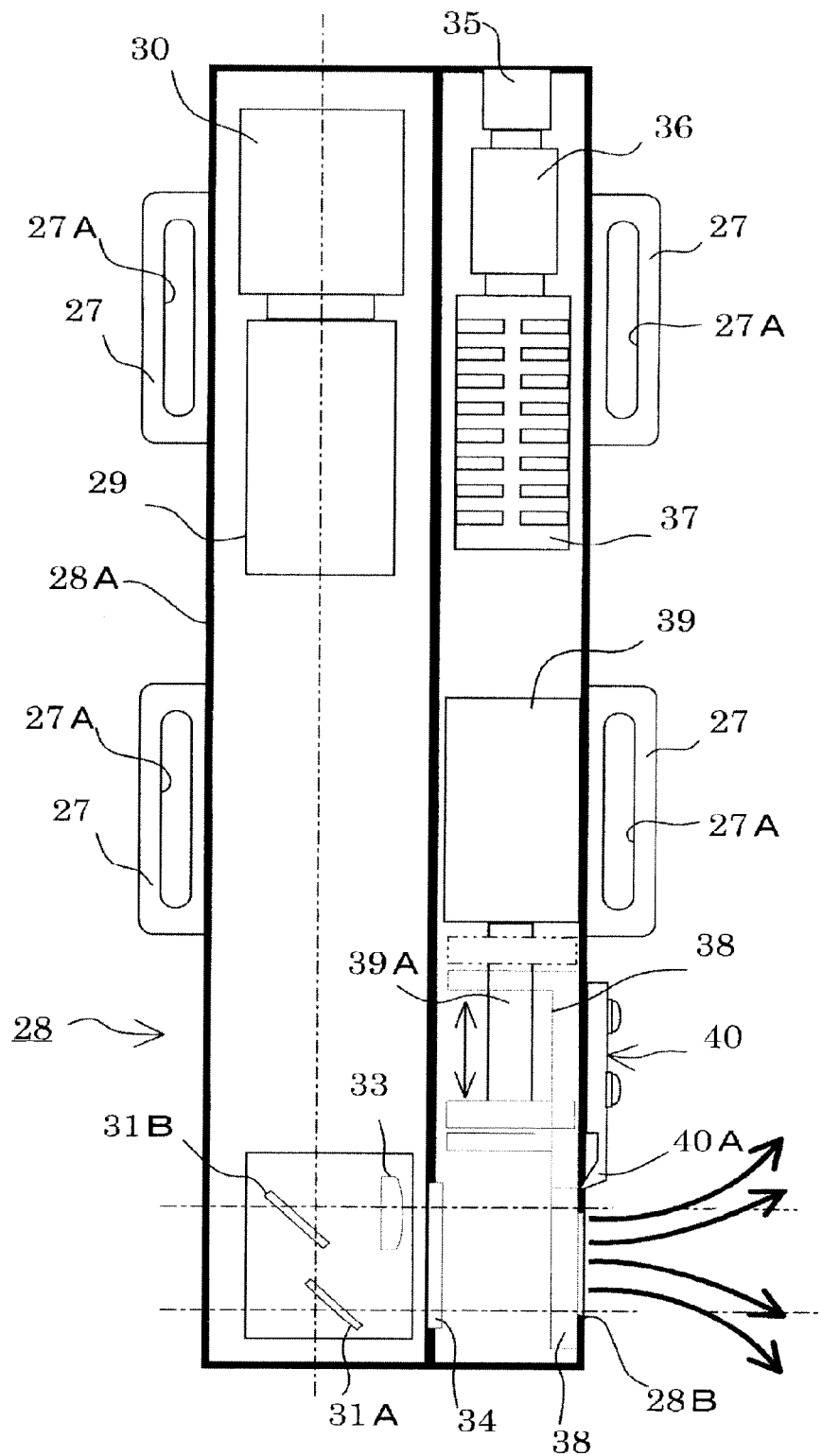
FIG. 3 is an end view of a camera apparatus shown in FIG. 2.

As illustrated in FIG. 3, a housing 28A of the camera apparatus 28 has a two-stage structure, where an upper stage of the housing 28A is an imaging space (also referred to as lens chamber) and a lower stage of the housing 28A is a dust-proof space (also referred to as shutter chamber). Specifically, a camera 30 of, for example, five million pixels, an imaging lens body 29, mirrors 31A, 31B and a focusing lens 33 are housed in the upper stage of the rectangular tube-shaped housing 28A. In addition, in an undersurface of the upper stage of the housing 28A, a transparent protective glass 34 is placed so as to face a lower side of the mirrors 31A, 31B and the focusing lens 33 (that is, a portion to be an optical path). In addition, a pair of the mirrors 31A, 31B and the focusing lens 33 are positioned and fixed as a pair of a mirror lens bodies with respect to each other. In addition, the imaging space is always kept at a predetermined air pressure such as +0.05 MPa.

In the lower stage of the housing 28A, an air connection unit 35, an air filter 36, a silencer (muffling apparatus) 37, a shutter 38 and a solenoid 39 for sliding the shutter 38 are arranged. The air connection unit 35 is connected with a compressor (not shown) for generating/outputting compressed air. In addition, the air continues injecting into the dust-proof space through the air filter 36/silencer 37 during a time from before opening the shutter 38 to the completion of closing the same.

In the lower stage of the housing 28A, an opening 28B for imaging is opened facing the protective glass 34 (a portion to be an optical path). The shutter 38 opens and closes the opening 28B, and is coupled to an operation unit 39A of the solenoid 39. Moreover, a metallic wiper 40 is fixed on the housing 28A, and a tip 40A of the wiper 40 is arranged so as to abut with the opening 28B and come in contact with the shutter 38. In addition, when the camera apparatus 28 is used, the shutter 38 is slid, and the opening 28B, more particularly the optical path of the camera 30, is opened. When the camera apparatus 28 is not used, the shutter 38, more particularly the opening 28B, is closed to cover an outer surface of the protective glass 34 to protect from swarf, oil and dust, or the like flying apart at a time of cutting. In addition, when the solenoid 39 is on, the shutter 38 slides to the solenoid 39 side, the opening 28B is opened, and swarf or the like is stripped off which is attached to an outer surface of the shutter 38 when the shutter 38 slides. This is to prevent swarf or the like from being attached to an outside of the shutter 38 and thereafter hampering the closing and opening of the shutter 38.

More specifically, the camera apparatus 28 is configured so as to be insusceptible to the environment even when being placed in the processing zone S2 (see FIG. 1) where swarf is filled, and thus can perform imaging securely. In addition, the camera eliminates the need of a slider mechanism or the like for moving the camera apparatus 28 to the processing zone S2 and the isolating zone S1, so that the camera can be cheaper and requires no time needed for sliding. Although a means for sliding the shutter 38 has been illustrated as an example of the solenoid 39, the means may be changed to other pneumatic cylinder apparatus.

Figure 5:
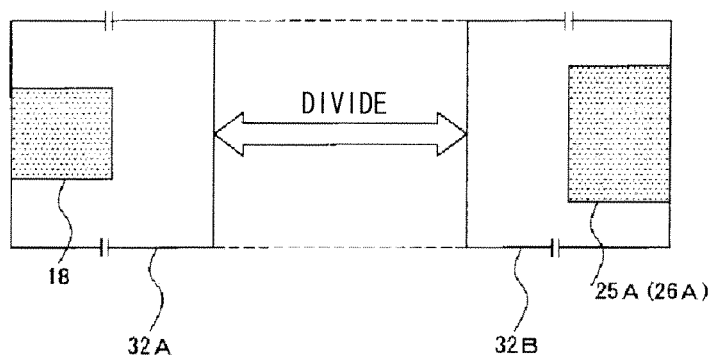
FIG. 5 is a view illustrating a division of the fields of view of the camera apparatus shown in FIG. 2.

As illustrated in FIG. 4, the above-mentioned mirrors 31A, 31B are disposed so as to divide a field of view of an imaging optical system thereof into two fields of view 32A, 32B and to extend an interval between both of the fields of view 32A, 32B. These mirrors 31A, 31S bend at a right angle each of optical paths between the imaging lens body 29 of the camera 30 and two subjects (the reference gauge 18, and the tool bits 25, 26), and divide each field of view area (synonymous with an imaging area) respectively (see FIG. 5). In addition, as illustrated in FIG. 4, the camera 30 is predetermined to image the reference gauge 18 in one field of view 32A that has been divided, and image chips 25A, 26A of tool bits 25, 26 for processing an outer diameter and an inner diameter, respectively, in the other field of view 32B. It should be noted that an imaging area shown in FIG. 5 is one in the case of using a camera of five million pixels, and has a size of 17 mm (2000 pixels) in a short side and 21. 5 mm (2500 pixels) in a long side. In addition, the inner diameter processing tool bit 25 is represented by a double-dashed chain line in FIG. 4. FIG. 4 is a diagram where the lower stage of the camera apparatus 28 is abbreviated.

As illustrated in FIG. 3, mounting boards 27 are provided at several places in the housing 28A, and a long hole 27A along a light axis of the camera 30 is formed on these mounting boards 27 respectively. In addition, the housing 28A makes alignment using a long hole 60 to adjust a position of an axial direction of the camera apparatus 30, so that an optical system of the camera 30 can be moved in the axial direction of the camera 30 corresponding to an outer diameter of the chuck 12. This moving mechanism may be configured so as to allow the optical system of the camera 30 to be automatically moved in the axial direction of the camera 30 corresponding to the outer diameter of the chuck 12 by a motor or the like, or to allow the optical system of the camera 30 to be manually moved in the axial direction of the camera 30 by an operator.

As illustrated in FIG. 2, a light source 44 for illumination is arranged at a position facing the camera apparatus 28 through a transparent tempered glass 42. In addition, a coolant injection section 43 is disposed for sluicing down swarf, grease or the like which is fallen onto the tempered glass 42. It should be noted that the light source 44 may be, for example, a light-emitting LED.

(Chip Detecting Method)

Figure 6:
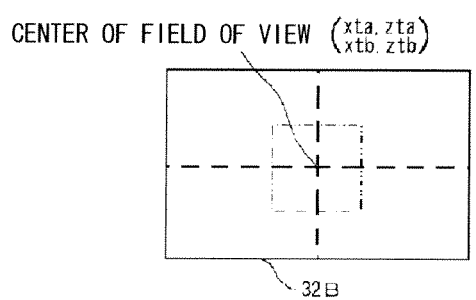
FIG. 6 is a view illustrating one of the fields of view shown in FIG. 5.
Figure 7:
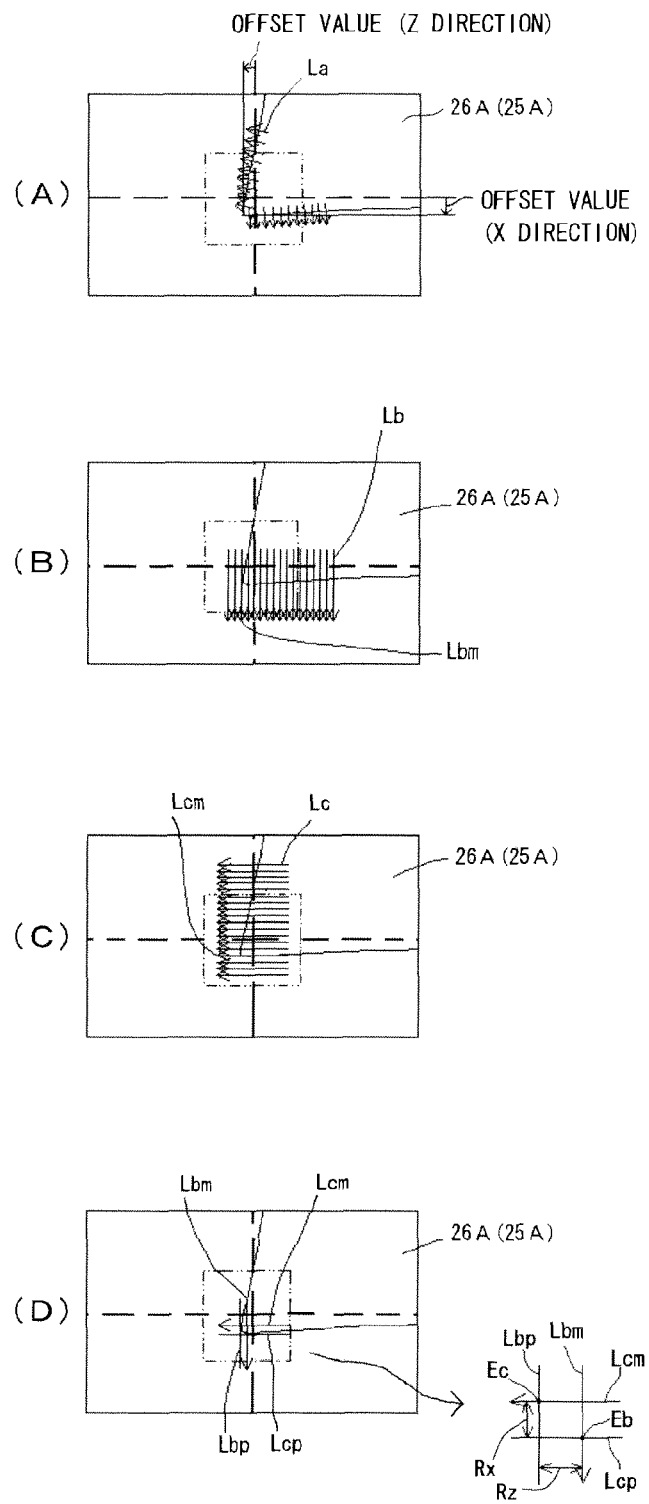
FIG. 7 is a view illustrating an inspection by a cutting tool.

As illustrated in FIG. 4, in a case of including and imaging (synonymous with viewing the whole) each of the reference gauge 18, and the chips 25A, 26A of the tool bits 25, 26 in each of the fields of view 32A, 32B of the camera 30, the top surfaces of the reference gauge 18 and the chips 25A, 26A of the tool bits 25, 26 are as aligned at the same length. In addition, edges of chips 25A, 26A shown in FIG. 4 can be obtained using, for example, a seek line. This seek line is a line segment free in a length and a slope that are set in a two-dimensional virtual screen, and is intended to obtain an position of an edge with respect to a center position in a line direction thereof. It should be noted that a solid line portion of FIG. 6 is an imaging area showing the chips 25A, 26A in the other field of view 32B (see FIG. 5), and is an overall detection area used for detecting the chips 25A, 26A in whole, and that a double-dashed chain line portion of FIG. 6 is a cutting edge detecting area used for detecting the tips of the chips 25A, 26A.

First, a method for detecting the chips 25A, 26A is performed as follows. As illustrated in FIG. 7(A), the edges of the chips 25A, 26A are obtained by setting a plurality of seek lines La. The edges of the chips 25A, 26A before and after being used are obtained and subjected to a pattern matching, and, if positions of the respective edges vary by not greater than a threshold value, the chips 25A, 26A is determined to be broken. Meanwhile, if the positions of the respective edges vary by greater than or equal to a threshold value, the chips 25A, 26A is determined to be expanded (also referred to as built-up edge) due to, for example, swarf adhering to the chips 25A, 26A. It should be noted that the threshold value has a range of, for example, 20 μm, which can be arbitrarily changed.

A nose of a chip can be also obtained using the seek line. First, as illustrated in FIG. 7(B), a plurality of seek lines Lb going downward are set at a predetermined interval, and a seek line Lbm at which a luminance maximal value (a point of changing from dark to light) is a lowermost point is obtained to be set as an X direction cutting line. Similarly, as illustrated in FIG. 7(C), a plurality of seek lines Lc going to the left are set at a predetermined interval, and a seek line Lcm at which a luminance maximal value (a point for changing from dark to light) becomes a leftmost point is obtained to be set as a Z direction cutting line. Next, as illustrated in FIG. 7(D), a distance Rz is obtained between the X direction cutting line Lbm and a line Lbp which is parallel to this X direction cutting line Lbm and passes through an edge Ec in the Z direction cutting line Lcm. Similarly obtained is a distance Rx between the Z direction cutting line Lcm and a line Lcp which is parallel to this Z direction cutting line Lcm and passes through an edge Eb in the X direction cutting line Lbm. In addition, one of the distance Rz or the distance Rx, which is larger, is set as a nose. If noses of the chips 25A, 26A after being used vary by greater than or equal to a set value from those of the chips 25A, 26A before being used, the chips 25A, 26A is determined to be worn.

More specifically, according to the present first embodiment, the reference gauge 18 and the chips 25A, 26A adjacent to the reference gauge 18 for measuring the position error of the camera apparatus 28 are imaged in a same field of view by the camera 30, and image processing of the chips 25A, 26A is performed, with the chips 25A, 26A and the reference gauge 18 being set at a reference position, and therefore the states of the chips 25A, 26A can be accurately detected.

(Configuration of Turret Gauge 46)

Figure 8:
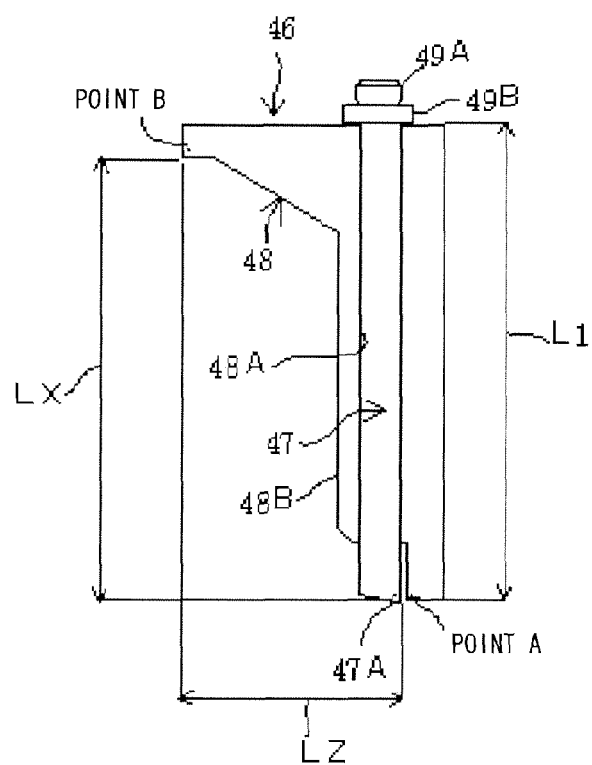
FIG. 8 is a side view of a turret gauge according to first embodiment.
Figure 9:
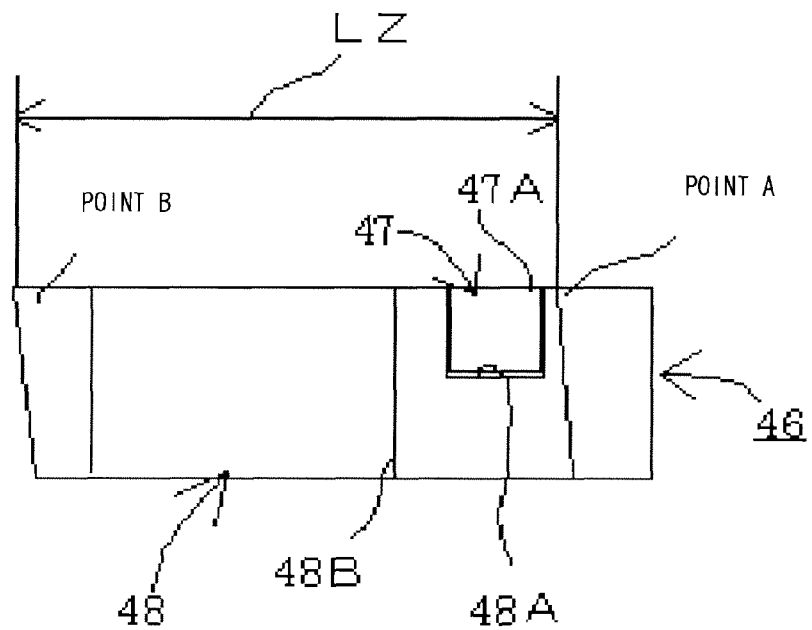
FIG. 9 is a bottom view of the turret gauge shown in FIG. 8.
Figure 10:
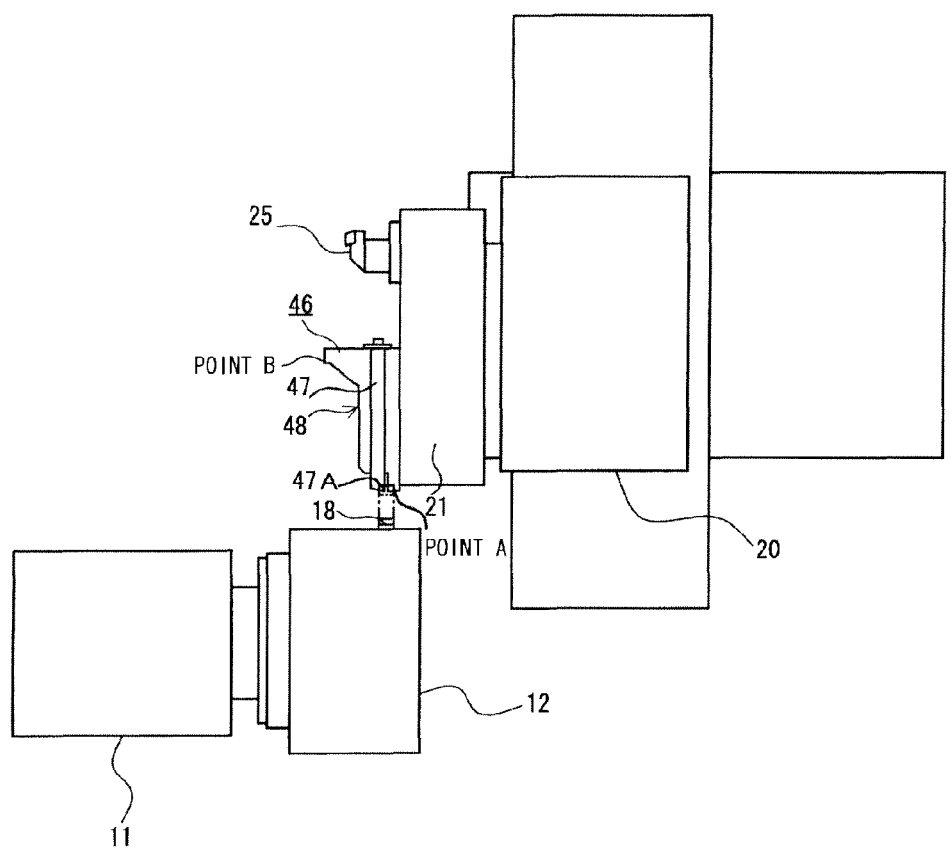
FIG. 10 is a view illustrating a measurement base point A of the turret gauge shown in FIG. 8 and a state of the field of view thereof.

A turret gauge 46 shown in FIG. 8 and FIG. 9 is a gauge for measuring a degree of thermal expansion/contraction of an NC table 50 (see FIG. 13) which includes a ball screw mechanism (not shown) (for example, an X axis and a Y axis) of the lathe S (see FIG. 1), and that of a lathe main body which includes the turret apparatus 20 (see FIG. 1). As illustrated in FIG. 10, the turret gauge 46 which is a reference means is configured so as to be mounted at a predetermined position of the tool post 21 (one of positions of placing a cutting tool).

This turret gauge 46 is comprised of an invar body 47 which is a reference body, and a gauge main body 48 which is an object to be measured and a mounting means. The invar body 47 is formed in, for example, a prismatic shape using a material (for example, an invar which is an invariable steel) with a smaller thermal expansion coefficient than that of a heat-treated steel constituting the lathe S (see FIG. 1). In addition, it is preferable that there is a difference in the thermal expansion coefficient between the object to be measured and the material of the reference body, and it is especially desirable that the difference is as remarkable as possible. Generally, a steel which is a constitutional material of a machine tool is used for the object to be measured, and therefore an invar with an extremely small thermal expansion coefficient, an aluminum alloy with a thermal expansion coefficient twice larger than that of a steel, or a magnesium alloy with a thermal expansion coefficient three times larger than that of a steel, or the like may be used for the reference body. Meanwhile, the gauge main body 48 is formed in an approximately right triangle shape using the heat-treated steel shown in FIG. 1 which is the same as that of the turret apparatus 20 (including the tool post 21) or the like.

In addition, in the gauge main body 48, as illustrated in FIG. 8, a hole 48A into which the invar body 47 is to be inserted is formed. This hole 48A is a bit larger than a thickness of the invar body 47, so that there is a clearance to prevent the invar body 47 from interfering with a wall constituting the hole 48A. As illustrated in FIG. 8, the invar body 47 has one end thereof fixed to the gauge main body 48 by a bolt 49A and a check plate 49B. In the invar body 47, a distance L1 from a fixed end which is one end thereof to an inclined leading edge 47A which is a free end has been set to a predetermined dimension in advance. In addition, in order that the invar body 47 is mounted on the gauge main body 48, only one point of the invar body 47 is supported by the gauge main body 48 and other points thereof remain free. The reason for doing so is that if the invar body 47 is fixed at two or more points, a bimetal effect would be generated by a difference in the thermal expansion coefficient between the invar body 47 and the gauge main body 48, thereby causing deformity.

As illustrated in FIG. 8, in the gauge main body 48, right-angled edges are formed respectively, so that each of two edges is a point A and a point B (measurement base point), which are base points for measurements in the X direction and the Z direction. Here, the edge interval in the X direction between the point A and the point B is set to have a reference dimension LX in the X direction, and the edge interval in the Z direction therebetween is set to have a reference dimension LZ in the Z direction. The gauge main body 48 is processed, when being manufactured, in such a manner that these reference dimensions LX and LZ would satisfy a certain accuracy (for example ±5 μm). The reason for this is that if a high accuracy of ±5 μm or better is required, the gauge main body 48 would be very expensive. Moreover, before the gauge main body 48 is mounted on a machine, a temperature of the gauge main body 48 and the above-mentioned dimensions LX and LZ are measured by a precision measuring instrument and recorded in a memory such as a RAM.

It should be noted that the thermal expansion coefficient of the invar body 47 is approximately one-tenth that of a steel, and that when the temperature of the turret gauge 46 changes by 1° C., a difference between the point A of the gauge main body 48 and the leading edge 47A of the invar body 47 becomes 1.8 μm. In addition, the CPU 60 (see FIG. 13) detects lengths of the reference dimensions Lx and LZ based on image data in a predetermined dimension at a predetermined temperature, and therefore there may be variation to some extent in the above-mentioned accuracy of the gauge main body 48. Here, the predetermined temperature is a predetermined temperature (normal ambient temperature of 20 to 22 degree C.) which is specified to detect and measure a dimension of the turret gauge 46 or the like, and the predetermined dimension is a dimension of the turret gauge 46 or the like at the above-mentioned predetermined temperature. It should be noted that when initializing a machine, the temperature of the gauge main body 48 is measured and a dimension within 1 μm in the distance between the point A and the point B of the gauge main body 48 is acquired. This acquiring method is performed by processing an image of the point A and the point B of the gauge main body 48 and the reference gauge 18 in a same imaging area. In addition, formed in the gauge main body 48 is a parallelism measuring reference surface 48B, which is used to position the turret gauge 46 at the tool post 21 in a parallel state.

Figure 11:
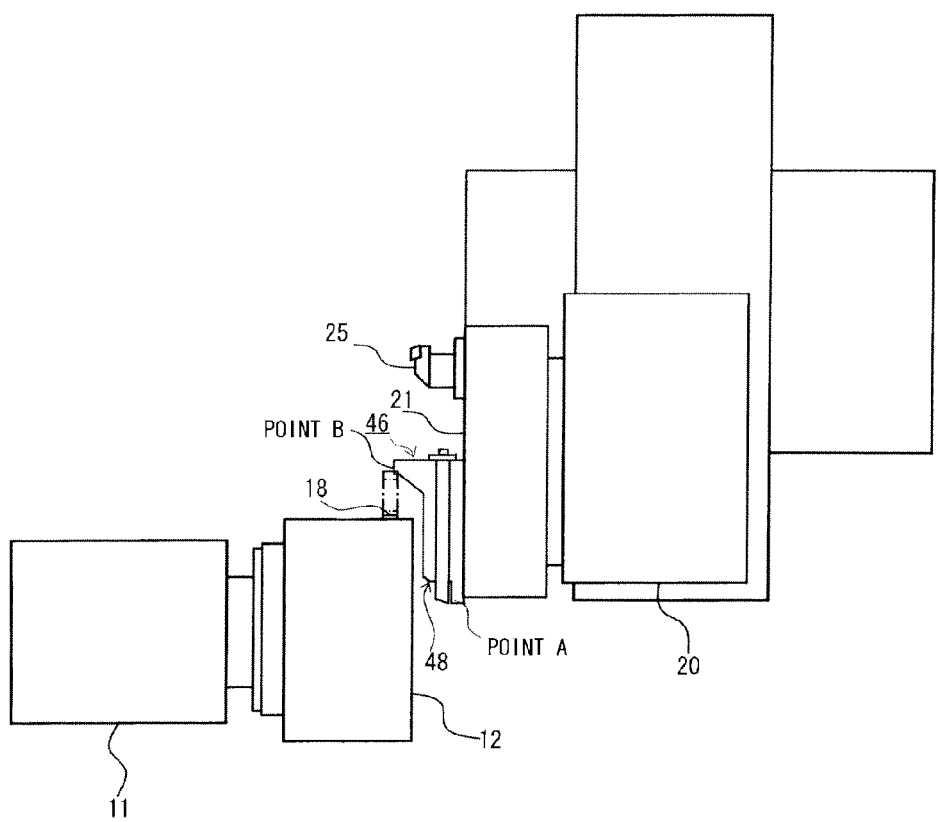
FIG. 11 is a view illustrating a measurement base point B of the turret gauge shown in FIG. 8 and a state of the field of view thereof.

When imaging by the camera apparatus 28, as illustrated in FIG. 10, positions of the point A of the gauge main body 48 and the leading edge 47A of the invar body 47 are obtained based on the reference gauge 18 fixed on the chuck 12. Furthermore, as illustrated in FIG. 11, a position of the point B of the gauge main body 48 is obtained based on the reference gauge 18 fixed on the chuck 12. It should be noted that frames indicated by a single-dashed chain line shown in FIG. 10 and FIG. 11 correspond to zones in fields of view 32A and 32B of the camera apparatus 28 shown in FIG. 4 and FIG. 5.

Figure 12:
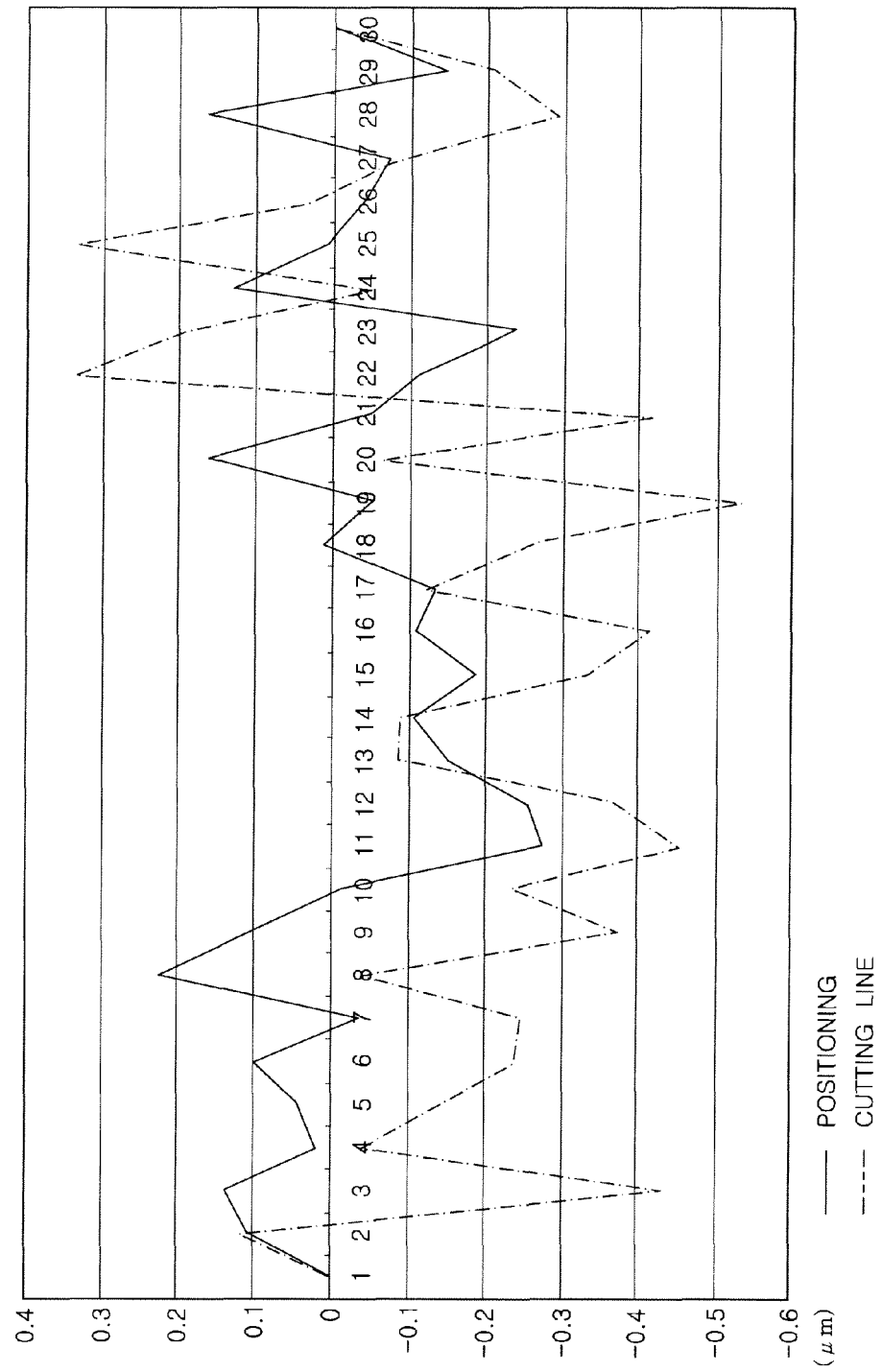
FIG. 12 is a view illustrating experimental data of image recognition accuracy.

In addition, in a camera of five million pixels, image recognition can be performed with a recognition accuracy of positioning the edges of a chip or the like illustrated in FIG. 7(A) being accurate to ±0.25 μm (=1/34 pixels), and with a recognition accuracy of positioning the cutting line Lcm or Lbm illustrated in FIG. 7(B) to FIG. 7(D) being accurate to ±0.45 μm (=1/19 pixels). More specifically, as illustrated in FIG. 12, thanks to the improvement in the above-mentioned recognition accuracy in a recent image processing technique, even a camera of an inexpensive optical system of five million pixels (actual dimension per 1 pixel is 8.6 μm) can sufficiently recognize a breakage/wear or the like of a chip, etc. in an image, and can measure the temperature of the gauge main body 48 on a 1° C. basis. It should be noted that FIG. 12 shows experimental data on accuracy of image recognition of the above-mentioned chip, wherein a vertical axis thereof indicates a size of a pixel (in μm), and a horizontal axis thereof indicates the number of experiments.

(Configuration of Control System of Lathe S)

Figure 13:
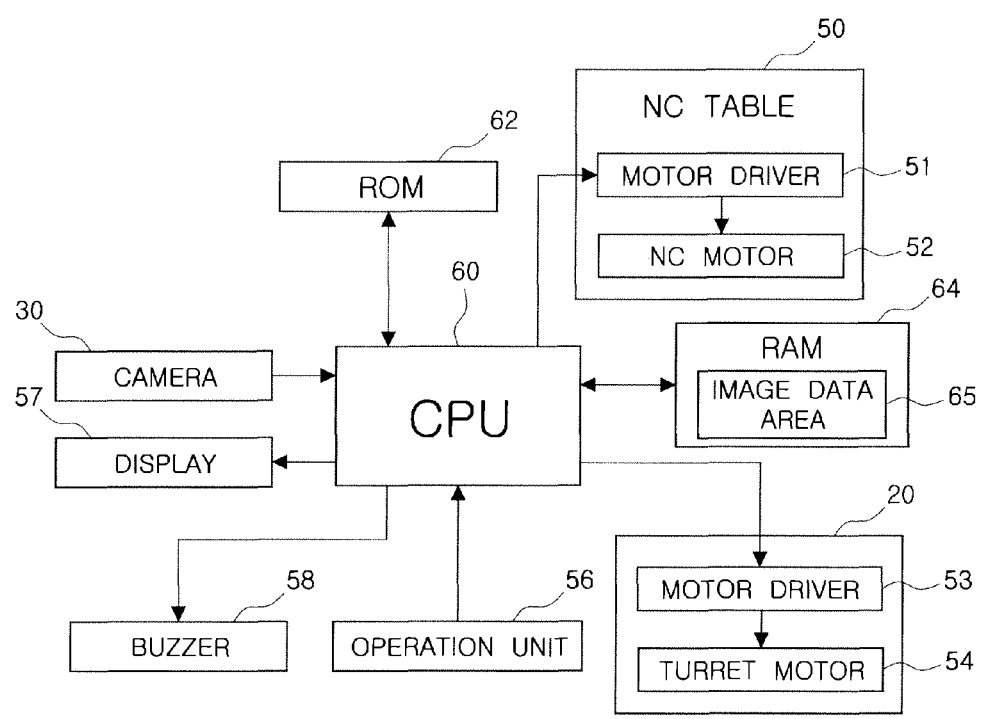
FIG. 13 is a block diagram of the turret lathe shown in FIG. 1.

As illustrated in FIG. 13, the lathe S is provided with a CPU 60, a ROM 62 which is nonvolatile memory, a RAM 64, a motor driver 51 arranged on the NC table 50, an NC motor 52, a motor driver 53 arranged on the turret apparatus 20, a turret motor 54, an operation unit 56, a display 57 and a buzzer 58. The CPU 60 which is a collating means and a correcting means controls an overall operation of the lathe S; for example, when an operation key arranged on the operation unit 56 is operated, performs processing based on the operation thereof. Furthermore, the CPU 60 is connected to the camera 30 which constitutes a part of the imaging means, and image data imaged by the camera 30 is input to the CPU 60.

The ROM 62 which is a recording means records a program for controlling various types of processes in the lathe S, based on which the lathe S is controlled. The RAM 64 which is a recording means has a recording area for reading and writing various types of data, such as an image data area 65, in which image data or the like is recorded. The motor 52 or 54 rotates based on a driving signal of the CPU 60 through the motor driver 51 or 53. The display 57 which is a display means displays image data or the like imaged by the camera 30. The buzzer 58 which is an alerting means outputs an alert sound.

Effects of Present Embodiment

A flow of image processing will be described based on flow charts shown in FIG. 14, FIG. 15 and FIG. 17 to FIG. 19. Here, processing in the lathe S is executed by the CPU 60, and represented by the flow charts shown in FIG. 14, FIG. 15 and FIG. 17 to FIG. 19. These programs have been recorded in advance in a program area of the ROM 62.

(Mode for Setting Initial Data of Turret Gauge)

A mode for setting initial data of a turret gauge (represented by TG in FIG. 14) shown in FIG. 10 or FIG. 11 is a process performed in an adjustment step during manufacturing a machine or during maintenance of the same using the lathe S. For example, when the machine is shipped from a factory, a temperature of the turret gauge 46 is measured by a hand-operated measuring instrument (not shown) with a machine temperature in a stable state.

Figure 14:
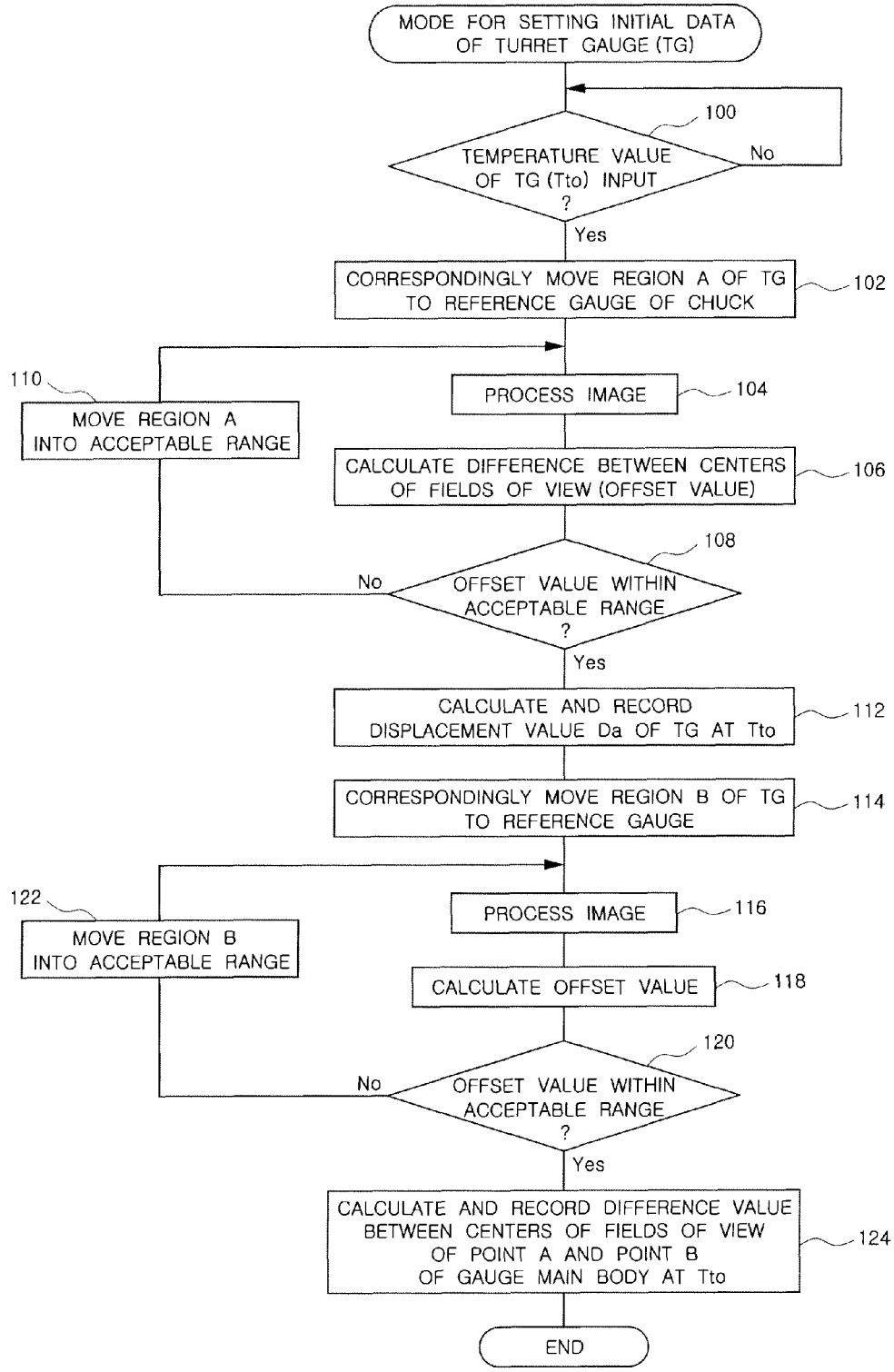
FIG. 14 is a flow chart diagram of a mode for setting initial data of a turret gauge according to the turret lathe shown FIG. 1.

In addition, as illustrated in FIG. 14, in step 100, the CPU 60 determines whether or not a temperature value of the turret gauge (a temperature value measured by the hand-operated measuring instrument) Tto has been input. If no in step 100, i.e., if no temperature value Tto has been input, the CPU 60 waits for the input. In this case, the CPU 60 reminds the data input using the display 57 or the buzzer 58 shown in FIG. 13. If yes in step 100, i.e., if the temperature value Tto has been input, the flow proceeds to step 102, where the CPU 60 correspondingly moves a region A of the turret gauge 46 to the reference gauge 18 of the chuck 12 (position shown in FIG. 10). More specifically, the CPU 60 rotates the tool post 21 in order to position the turret gauge 46 at an image processing position. Here, the region A is a region where the whole of the point A of the gauge main body 48 and the leading edge 47A of the invar body 47 can be viewed.

In step 104, the CPU 60 performs image processing, and in step 106, the CPU 60 calculates a difference between the centers of the fields of view (center position Xta, Zta with reference to the reference gauge 18), i.e., an offset value shown in FIG. 6. In step 108, the CPU 60 determines whether or not the offset value is within an acceptable range (for example, within 100 μm). If no in step 108, i.e., if the offset value is out of the acceptable range, the flow proceeds to step 110, where the CPU 60 moves the region A of the turret gauge 46 in such a manner that the region A is within the acceptable range. This process is continued until the region A is included in the acceptable range. If yes in step 108, i.e., if the offset value is within the acceptable range, the flow proceeds to step 112, where, based on the image data which is image-processed in step 104 (specifically, the image data in which the whole is viewed of the leading edge 47A of the invar body 47 and the point A of the gauge main body 48 in the acceptable range), the CPU 60 calculates a displacement value Da of the turret gauge 46 at the temperature value Tto, and records the value in the RAM 64. The displacement value Da is a difference value in a relative difference position of the point A of the gauge main body 48 with respect to the leading edge 47A of the invar body 47. More specifically, the displacement value Da is used to detect a dimension value after heat displacement (expansion or contraction) of the gauge main body 48 of a steel at the temperature value Tto, based on which the CPU 60 detects the temperature of the gauge main body 48 at the time of a subsequent measurement.

In step 114, the CPU 60 correspondingly moves the region B of the turret gauge 46 to the reference gauge 18 of the chuck 12 (position shown in FIG. 11). Here, the region B is a region where the whole of the vicinity of point B of the gauge main body 48 can be viewed. In step 116, the CPU 60 performs image processing, and in step 118, the CPU 60 calculates a difference between the centers of the fields of view (Xtb, Ztb), i.e., the offset value shown in FIG. 6. In step 120, the CPU 60 determines whether or not the offset value is within an acceptable range. If no in step 120, i.e., if the offset value is out of the acceptable range, the flow proceeds to step 122, where the CPU 60 moves the region B of the turret gauge 46 in such a manner that the region B is within the acceptable range. If yes in step 120, i.e., if the offset value is within the acceptable range, the flow proceeds to step 124, where the CPU records in the RAM 64 difference values Dtx, Dtz between the centers of the fields of view of the point A and the point B of the gauge main body 48 at the temperature value Tto. In addition, if the offset value is within the above-mentioned acceptable range, an NC table position at a time of the mode for setting the initial data is regarded as an NC table position at which a region A and a region B are present with the above-mentioned offset value being in the center of the field of view. The difference values are a X difference in an X direction (Dtx=Xta−Xtb) and a Z difference in a Z direction (Dtz=Zta−Ztb). More specifically, the reason for providing the point A and the point B on the gauge main body as the measurement base points is to detect a heat displacement in the X direction and the Z direction in the turret apparatus 20 (including a ball screw mechanism)

(Mode for Setting Initial Data of Image Capturing Position)

Figure 15:
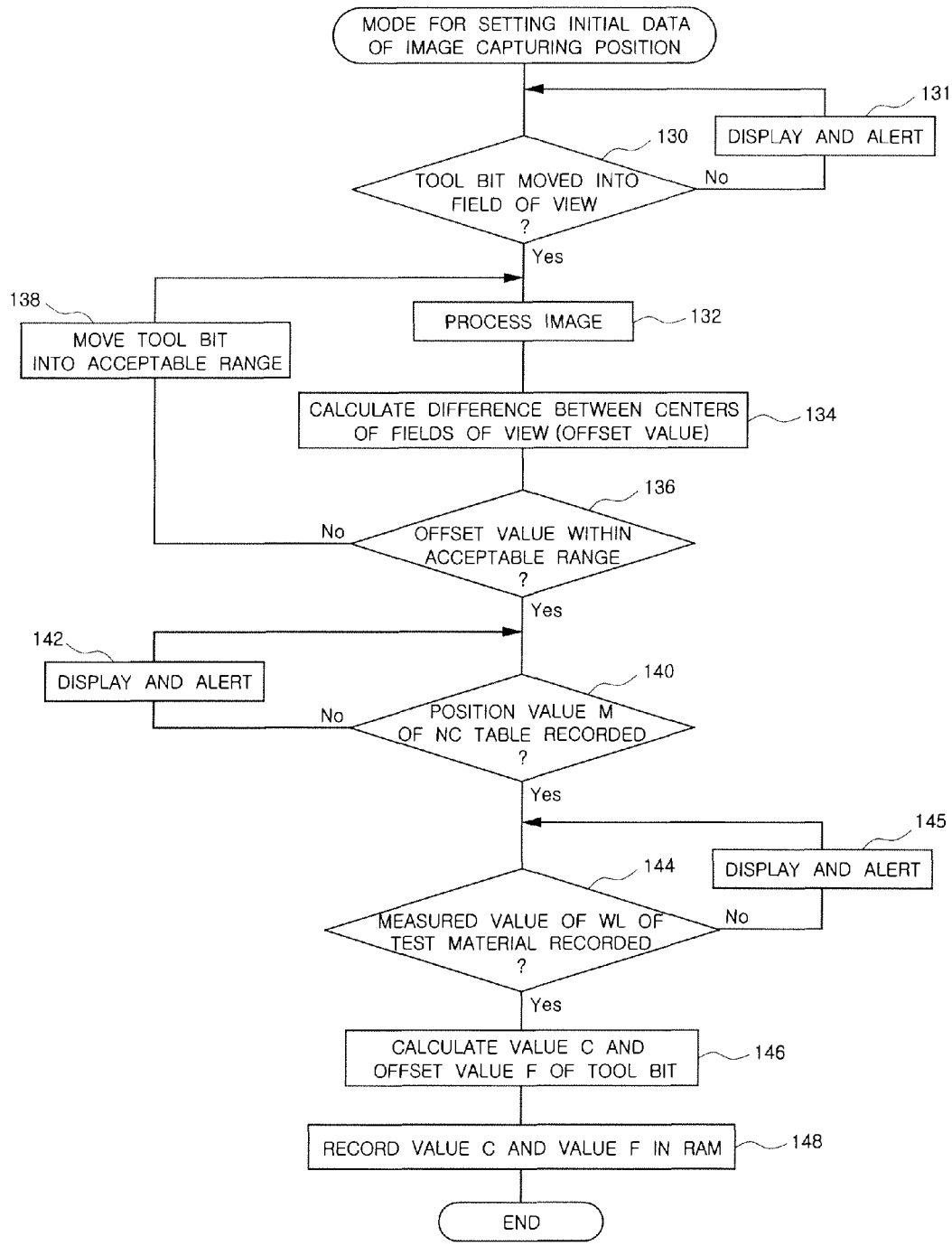
FIG. 15 is a flow chart diagram of a mode for setting initial data of an image capturing position according to the turret lathe shown FIG. 1.
Figure 16:
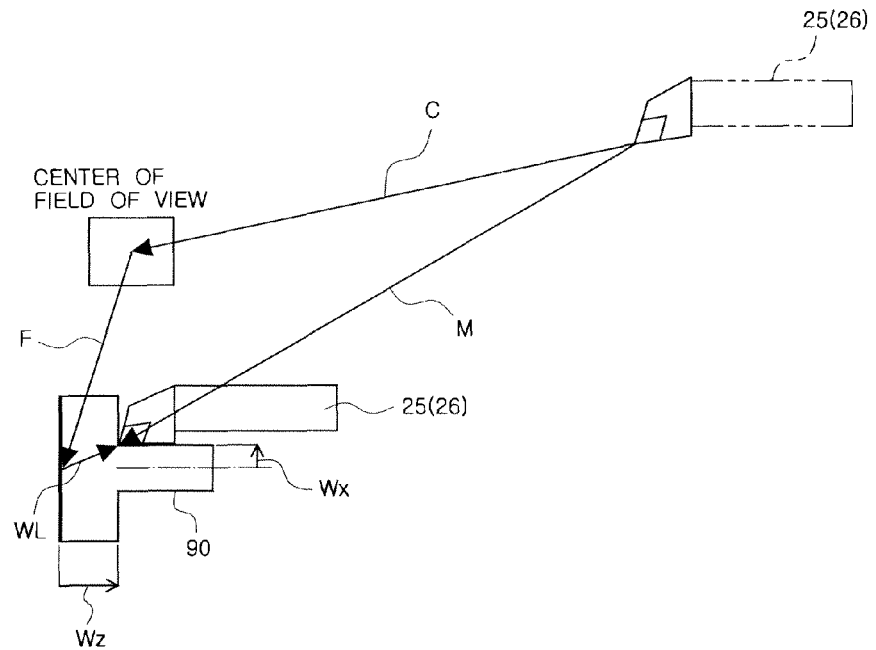
FIG. 16 is a view illustrating the details of the process of the flow chart of FIG. 15.

A mode for setting initial data of an image capturing position shown in FIG. 15 or FIG. 16 is a process which is performed in an adjustment step or the like during manufacturing a machine using the lathe S. First, using a test material 90 shown in FIG. 16, the tool bits 25, 26 are manually moved into a field of view of the camera 30. Hereinafter, the above-mentioned mode will be described with reference to FIG. 16. It should be noted that setting of the initial data of the image capturing position is made after setting the initial data of the above-mentioned turret gauge.

As illustrated in FIG. 15, in step 130, the CPU 60 (see FIG. 13) determines whether or not the tool bits 25, 26 have been moved into the field of view. If no in step 130, i.e., the tool bits 25, 26 have not been moved into the field of view, the flow proceeds to step 131, where the CPU 60 makes the display 57 to display and the buzzer 58 to issue an alert, as shown in FIG. 13. In step 132, the CPU 60 performs image processing, and in step 134, the CPU 60 calculates a difference between the centers of the fields of view, i.e., an offset value F shown in FIG. 16. In step 136, the CPU 60 determines whether or not the offset value F is within an acceptable range (for example, within 100 μm). If no in step 136, i.e., if the offset value is out of the acceptable range, the flow proceeds to step 138, where the CPU 60 moves the tool bits 25, 26 in such a manner that the tool bits 25, 26 is within the acceptable range. This process is continued until the tool bits 25, 26 are included in the acceptable range.

If yes in step 136, i.e., if the offset value is within the acceptable range (a position of a center of the field of view at that time is defined as C), the flow proceeds to step 140, where the CPU 60 determines whether or not a position value M of the NC table 50 (see FIG. 13) has been recorded. It should be noted that this process is premised on that the test material 90 is finish-cut manually (cut with a small cutting amount), and the position value M of the NC table 50 at that time is obtained and recorded in the RAM 64. If no in step 140, i.e., if no position value M has been recorded, the flow proceeds to step 142, where the CPU 60 makes the display 57 to display and the buzzer 58 to sound an alert.

If yes in step 140, i.e., if the position value M has been recorded, the flow proceeds to step 144, where the CPU 60 determines whether or not a measured value of a workpiece dimension WL has been recorded. It should be noted that this process is premised on that the dimension WL of the workpiece W (specifically, values of the Wx, Wz shown in FIG. 16) is obtained by a micrometer and recorded in the RAM 64. If no in step 144, i.e., if no measured value of the dimension WL has been recorded, the flow proceeds to step 145, where the CPU 60 makes the display 57 to display and the buzzer 58 to sound an alert.

If yes in step 144, i.e., if the measured value of the dimension WL has been recorded, the flow proceeds to step 146, where the CPU 60 makes calculation by substituting the value C and the offset value F of a tool bit into a vector formula (M=C+F+WL or F=M−C−WL), and in step 148, records the value C and the value F in the RAM 64.

It should be noted that the value C varies for every tool bit, and that only one value F is available in one turret apparatus. In addition, the test material 90 is applicable if having one diameter and one edge face respectively. Furthermore, the CPU 60 obtains the value C and the value M of each tool bit and records the values in the RAM 64. In practice, based on the value M calculated by the above-mentioned formula M=C+F+WL, the CPU 60 moves the NC table 50 to a location M shown in FIG. 16 to perform cutting.

(Image Processing Mode in Calibration Cycle)

Figure 17:
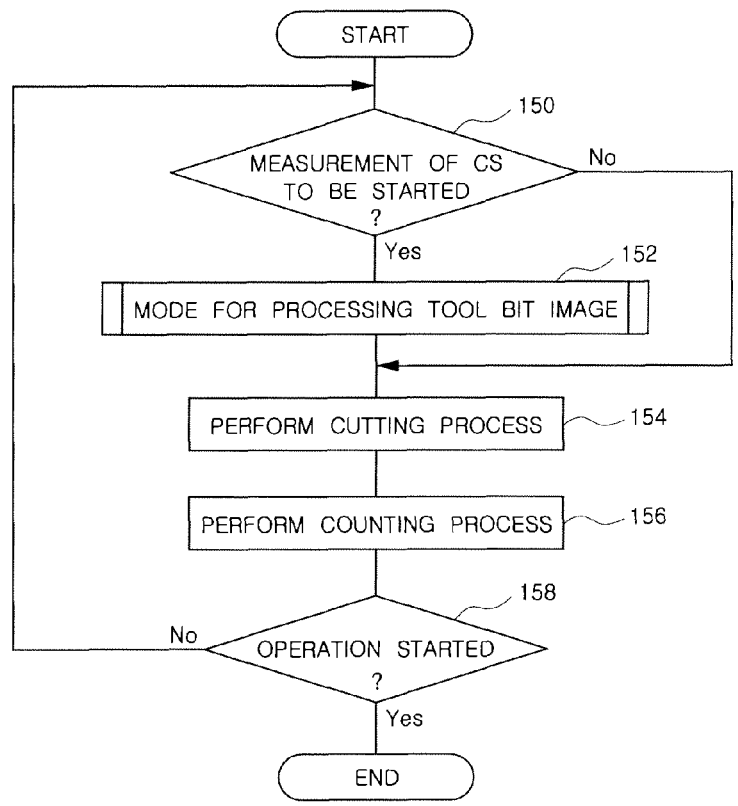
FIG. 17 is a flow chart diagram illustrating a process flow in a calibration cycle.
Figure 18:
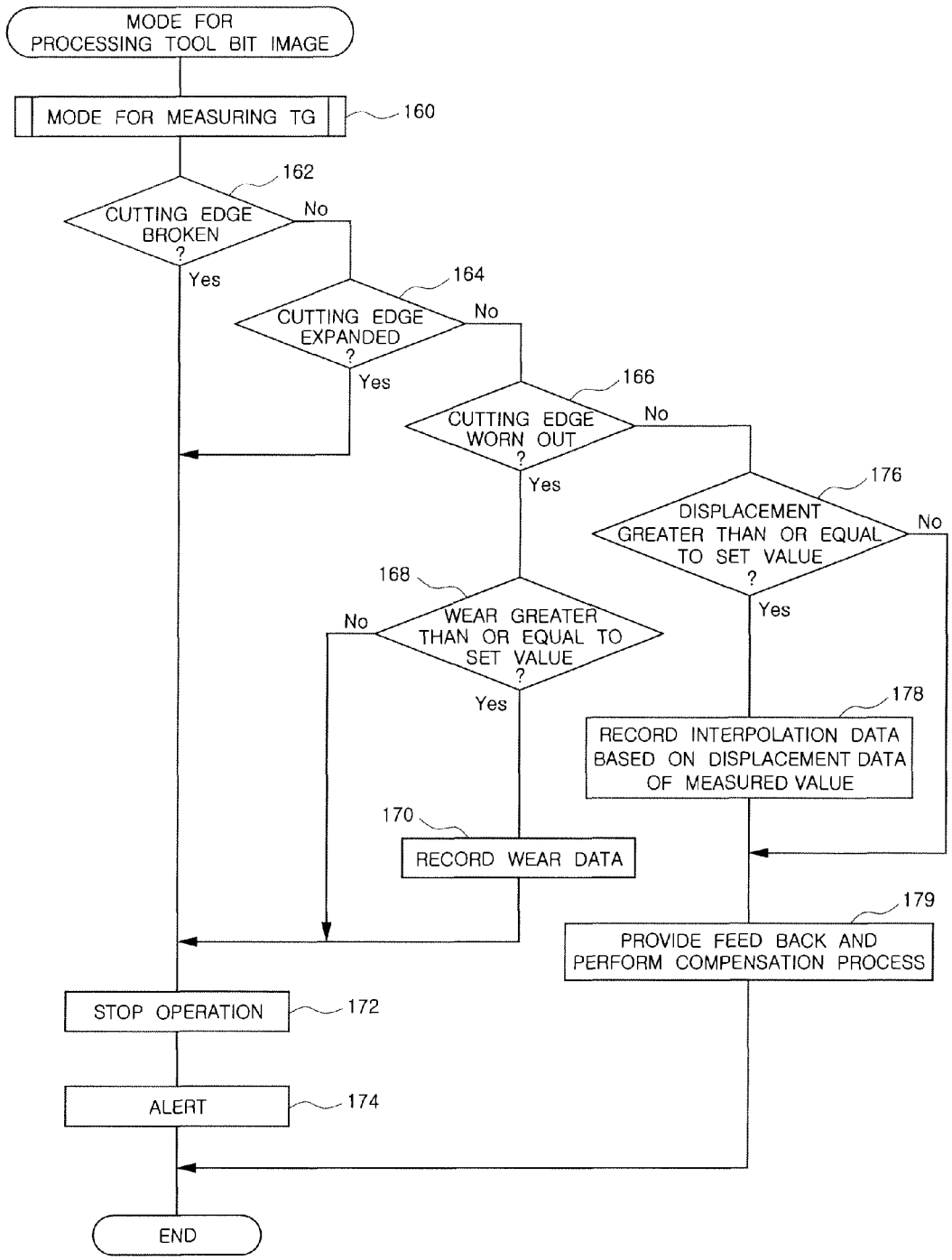
FIG. 18 is a subroutine diagram of a mode for processing a tool bit image shown FIG. 17.
Figure 19:
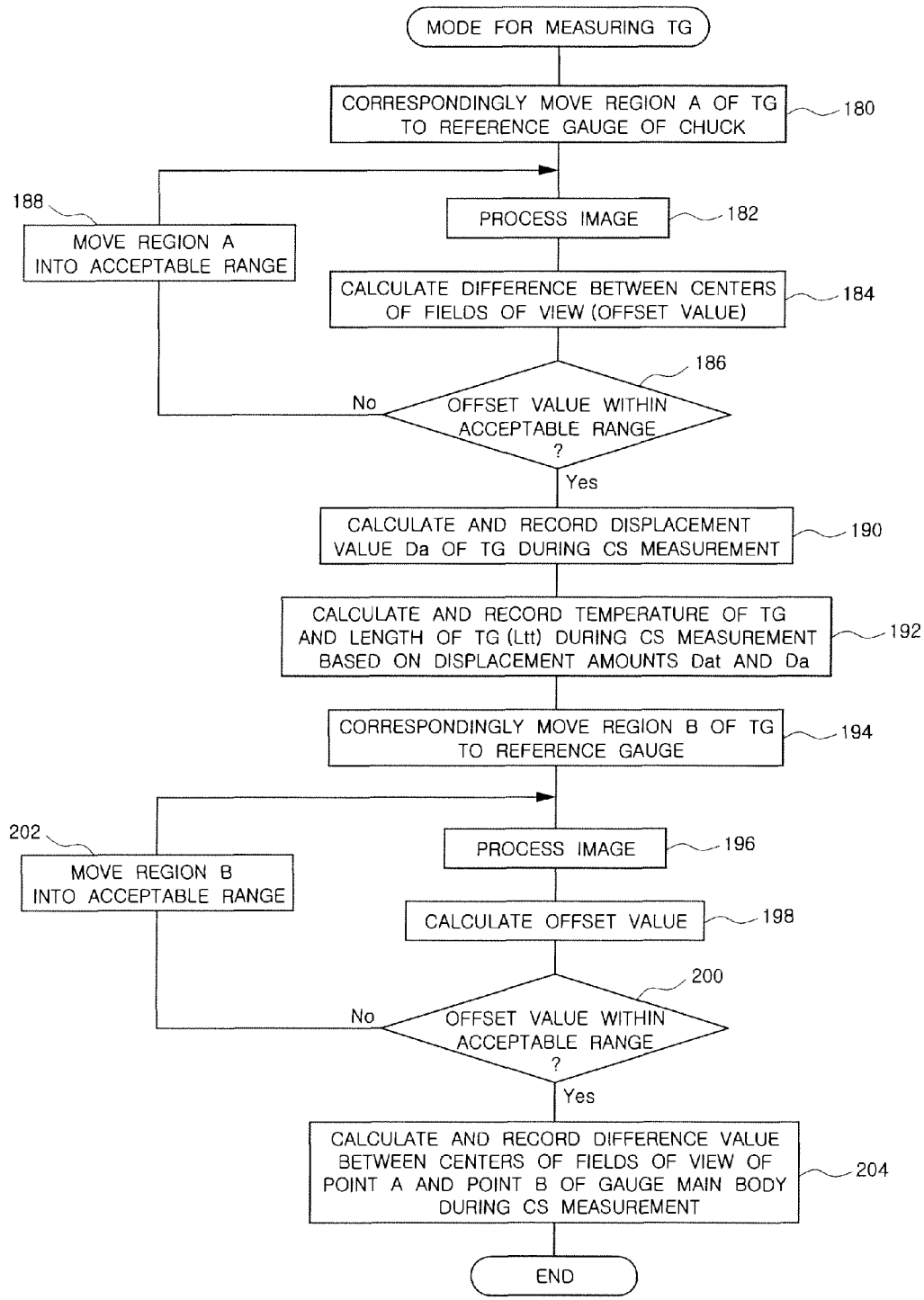
FIG. 19 is a subroutine diagram of a mode for measuring a turret gauge shown in FIG. 18.

The flow charts shown in FIG. 17 to FIG. 19 illustrate a routine performed in a calibration cycle (represented by CS in FIG. 17). The calibration cycle is for conducting an inspection, forcibly providing a predetermined interval when the lathe S is in operation, in order to obtain a compensation value to keep cutting accuracy at a predetermined standard. More specifically, the flow charts shown in FIG. 17 to FIG. 19 illustrate a process after starting an operation of the lathe S.

As illustrated in FIG. 17, in step 150, the CPU 60 determines whether or not a measurement of a calibration cycle (represented by CS in FIG. 17) is to be started. The CPU 60 determines whether or not the measurement is to be started by counting a preset number of cutting times (for example, 100) or a preset time. If yes in step 150, i.e., if the measurement is to be started, the flow proceeds to step 152, where the CPU 60 performs a process of a mode for processing a tool bit image. This mode for processing a tool bit image is for a process in a subroutine shown in FIG. 18.

If no in step 150 (if no measurement is to be started) or after completion of the process in step 152, the CPU 60, in step 154, performs a cutting process, and, in step 156, performs a counting process for counting the number of cutting times (or the number of calibration times). In step 158, the CPU 50 determines whether or not the operation of the lathe is completed (including the case of performing an operation of stopping the calibration cycle). If yes in step 158, this routine is completed. If no in step 158, the flow returns to step 150, where the CPU 60 performs each process continuously.

(Mode for Processing Tool Bit Image)

The mode for processing a tool bit image in step 152 shown in FIG. 17 will be described with reference to the subroutine shown in FIG. 18. In step 160, the CPU 60 performs a process of a measuring mode. This measuring mode is a process in the subroutine shown in FIG. 19. When the process in step 160 is completed, in step 162, the CPU 60 determines whether or not a cutting edge is broken. If no in step 160, in step 164, the CPU 60 determines whether or not the cutting edge is expanded (synonymous with built-up edge), and if no in step 164, in step 166, the CPU 60 determines whether or not the cutting edge is worn out. It should be noted that these determination techniques use the above-mentioned seek line or the like.

If yes in step 166, i.e., if the CPU 60 determines that the cutting edge is worn out, the flow proceeds to step 168, where the CPU 60 determines that the wear is greater than or equal to a set value (for example, 20 μm). If yes in step 168, i.e., if the wear is greater than or equal to the set value, the flow proceeds to step 170, where the CPU 60 records data of a wear amount in the RAM 64 (as data for maintenance, etc.). In addition, if yes in step 162 or step 164, or if no in step 168, or after completion of the process in step 170, the CPU 60, in step 172, forcibly terminates the operation of the lathe S (including, for example, performing a fail-safe procedure for prohibiting a cutting operation or the like until a tool bit is replaced) and, in step 174, issues an alert. In particular, the CPU 60 makes the display (see FIG. 13) to display, and activates the buzzer 58 to issue an alert sound or to output an alert voice from a speaker (not shown). An operator is reminded of tool bit replacement by the above-mentioned alert. It should be noted that if any foreign matter such as swarf adheres to an imaged portion in a field of view, the CPU 60 can regard this situation as an error by means of an image recognition function, and thus can perform a fail-safe procedure. In addition, if, in step 166, determining that the cutting edge is worn out, the CPU 60 terminates the operation of the lathe S to replace a chip, even though the wear is less than or equal to the set value.

If no in step 166, i.e., if the CPU 60 determines that no cutting edge is worn out, the flow proceeds to step 176, where the CPU 60 determines whether or not the displacement of the cutting edge is greater than or equal to a set value (for example 100 μm). The displacement of the cutting edge is determined by detecting an overall position of the cutting line in FIG. 7, and may include not only heat displacement but also wear of a cutting edge. If yes in step 176, i.e., if the displacement is greater than or equal to the set value, the flow proceeds to step 178, where the CPU 60 records interpolation data in the RAM 64 (as data for maintenance, etc.) based on displacement data at the time of a measurement. In addition, if no in step 176, or after completion of a process in step 178, the flow proceeds to step 179, where the CPU 60 provides a feed back and performs a compensation process. More specifically, according to first embodiment, the processing position is corrected by calculating the degree of thermal expansion/contraction of the lathe based on the temperature of the gauge main body 47 and positions of two points A and B at the time of not cutting during the operation of the lathe; and therefore even if the processing position is displaced by the thermal expansion/contraction of the lathe during the operation of the lathe, the displacement of the processing position can be corrected with high accuracy, and processing accuracy of the workpiece W can be improved.

(Mode for Measuring Turret Gauge)

The measuring mode in step 160 shown in FIG. 18 will be described with reference to the subroutine shown in FIG. 19. It should be noted that the measuring mode in FIG. 19 is a mode for measuring the turret gauge (represented by TG in FIG. 19 as well) 46. As illustrated in FIG. 19, in step 180, the CPU 60 correspondingly move the region A of the turret gauge 46 to the reference gauge 18 of the chuck 12 (position shown in FIG. 10).

The CPU 60, in step 182, performs image processing, and, in step 184, calculates a difference between the centers of the fields of view (Xtat, Ztat), i.e., an offset values. In step 186, the CPU 60 determines whether or not the offset value is within acceptable range (for example, within 100 μm). If no in step 186, i.e., if the offset value is out of the acceptable range, the flow proceeds to step 188, where the CPU 60 moves the region A of the turret gauge 46 in such a manner that the region A is within the acceptable range. This process is continued until the region A is included in the acceptable range. If yes in step 186, i.e., if the offset value is within the acceptable range, the flow proceeds to step 190 where, based on the image data which is image-processed in step 182 (specifically, the image data in which the whole is viewed of the leading edge 47A of the invar body 47 and the point A of the gauge main body 48 in the acceptable range), the CPU 60 calculates the displacement amount Dat of the turret gauge 46 at the time of a calibration cycle measurement (hereinafter, referred to as "at the time of a CS measurement"), and records the displacement amount in the RAM 64.

In step 192, based on the difference between the above-mentioned displacement values Dat and Da (data recorded in the RAM 64 in step 112 in FIG. 14), the CPU 60 calculates the temperature of the turret gauge 46 at the time of a CS measurement, and calculates and records in the RAM 64 lengths Ltt of an LX and an LZ (see FIG. 8) of the gauge main body 48 after heat displacement at the temperature. It should be noted that, when the temperature is changed by 1° C. from that of the thermal expansion coefficient of a steel, the thickness of a 100 mm steel increases or decreases by 1 μm, and therefore that if the CPU 60 calculates the difference between the displacement values Dat and Da, the temperature and the length Ltt of the turret gauge 46 can be calculated. In addition, if the reference body is made of an invariable steel such as an invar, a thermal expansion per se of the steel is measured.

In step 194, the CPU 60 correspondingly moves the region B of the turret gauge 46 to the reference gauge 18 of the chuck 12. The CPU 60, in step 196, performs image processing, and, in step 198, calculates a difference between the centers of the fields of view (Xtbt, Ztbt), i.e., an offset value. In step 200, the CPU 60 determines whether or not the offset value is within the acceptable range. If no in step 200, i.e., if the offset value is out of the acceptable range, the flow proceeds to step 202, where the CPU 60 moves the region B of the turret gauge 46 in such a manner that the region B is within the acceptable range. If yes in step 200, i.e., if the offset value is within the acceptable range, the flow proceeds to step 204, where the CPU 60 calculates a X difference value (Dtx=Xtat−Xtbt) and a Z difference value in the Z direction (Dtz=Ztat−Ztbt) between the centers of the fields of view of the point A and the point B of the gauge main body 48 at the time of the CS measurement, and records the values in the RAM 64.

More specifically, in step 179 shown in FIG. 18, the CPU 60 not only calculates the difference in the point A and the point B of the gauge main body 48 but also considers the heat displacement amount of the gauge main body 48, and therefore can accurately detect a heat displacement amount of a ball screw mechanism or the like. Consequently, according to first embodiment, the X difference value and the Z difference value mentioned above are compared to the length Ltt, and based on the ratio of the compared values, the movement of the turret apparatus 20 (see FIG. 1) in the X axis direction and the Z axis direction is corrected by two-point linear interpolation of a distance of the movement of a tool bit from the position of the center of the field of view shown in FIG. 16 to each cutting position in the X direction and the Z direction (a process in step 179 in FIG. 18 is performed).

For example, at the time of not cutting (at the time of a CS) during the operation of the lathe, regarding the temperature of the gauge main body 48 and a position difference between the point A and the point B (a plurality of measurement base points) of the gauge main body 48, not only a vector difference between the point A and the point B of the gauge main body 48 is measured, but also the temperature of the gauge main body 48 at the time of processing is measured, and the measured value thereof at the time of processing is calculated and interpolated, so that the thermal expansion/contraction of the lathe per se can be almost completely compensated. Therefore, even if a processing position is displaced by the thermal expansion/contraction of the lathe (including a ball screw mechanism) during the operation of the lathe, the displacement of the processing position can be corrected with high accuracy, and processing accuracy of a workpiece W (see FIG. 1) can be improved.

Second Embodiment

Figure 20:
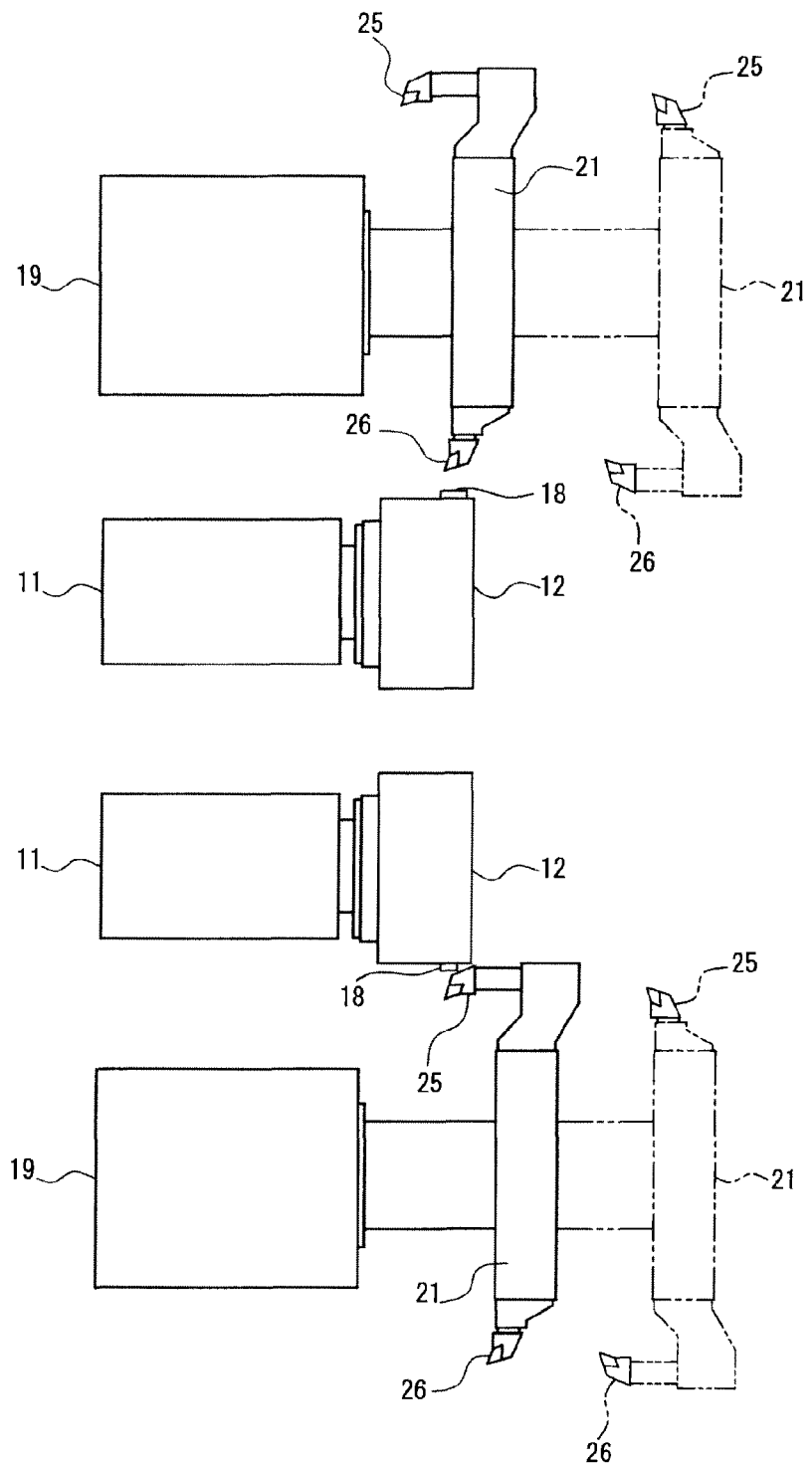
FIG. 20 is a top view illustrating a configuration of a principal section of a double-spindle face lathe of second embodiment.

Second embodiment of the present invention will be described using FIGS. 20 to 24. However, substantially the same parts as those in the above-mentioned first embodiment are denoted by the same reference signs to omit or simplify the explanation thereof, and different parts will be mainly described. Second embodiment is an example applied to a double-spindle face lathe as illustrated in FIG. 20. In particular, two main spindles 11 are provided so as to lie on the right side and the left side and extend horizontally and in parallel to each other, and a chuck 12 for holding a workpiece is provided at the anterior end of each main spindle 11. Tool posts 21 are arranged, in parallel to an axis line of each main spindle 11, at a position on the left side and a position on the right side of the right and left main spindles 11, respectively. Each of the tool posts 21 is configured so as to be movable in an anteroposterior direction and rotatable around a shaft center of the tool post 21 by a driving apparatus 19. Various types of tool bits (for example, an inner diameter processing tool bit 25, an outer diameter processing tool bit 26) are held at the outer periphery of each tool post 21, so that a tool bit used for cutting a workpiece can be selected by rotating each tool post 21.

Figure 21:
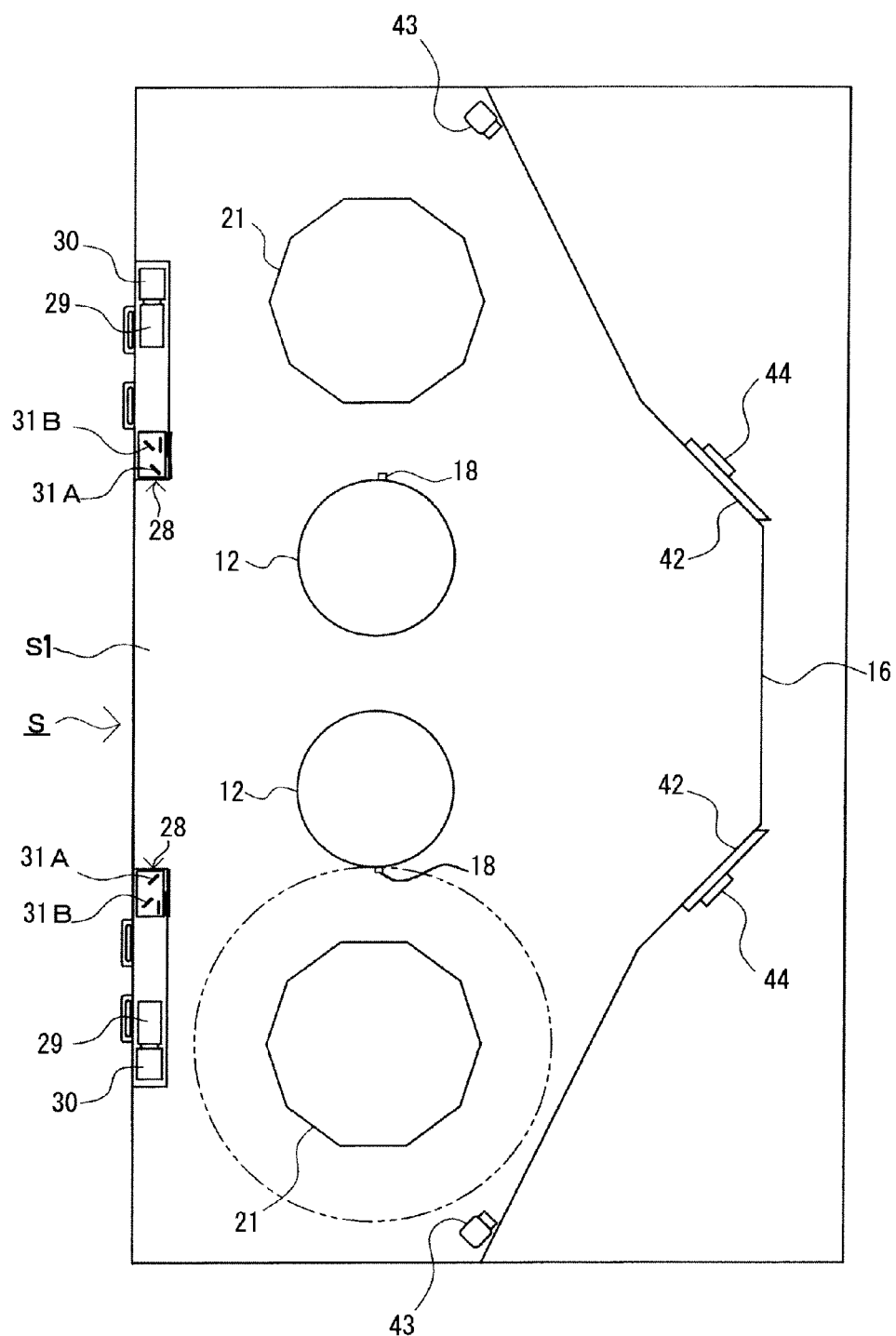
FIG. 21 is a front view illustrating the configuration of the principal section of the double-spindle face lathe shown in FIG. 20.

As illustrated in FIG. 21, two camera apparatuses 28 are arranged horizontally on a ceiling of a processing zone S1 of the lathe S, being positioned just above between each tool post 21 and each chuck 12. It should be noted that the camera apparatuses 28 in FIG. 21 have an abbreviated lower stage thereof.

The undersurface of a processing zone S1 is formed so as to incline downward from both the right and left sides to a chip conveyor 16 at the center, and a light source 44 for illumination is provided through the tempered glass 42 at a position just below each camera apparatus 28 in the undersurface section of the processing zone S1. Coolant injection sections 43 for sluicing down swarf, oil and dust, or the like, which is fallen onto the undersurface of the processing zone S1 and the tempered glass 42, onto the chip conveyor 16 are provided on both the right and left sides of the undersurface of the processing zone S1.

Figure 22:
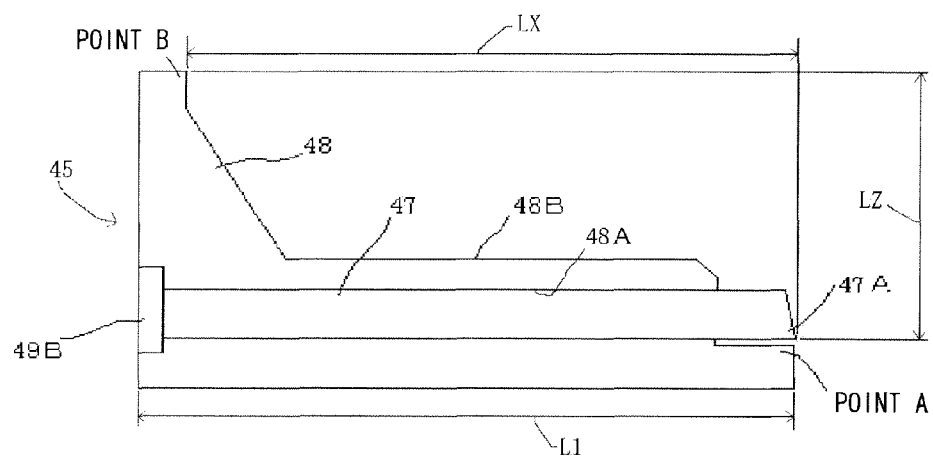
FIG. 22 is a side view of a turret gauge according to second embodiment.
Figure 23:
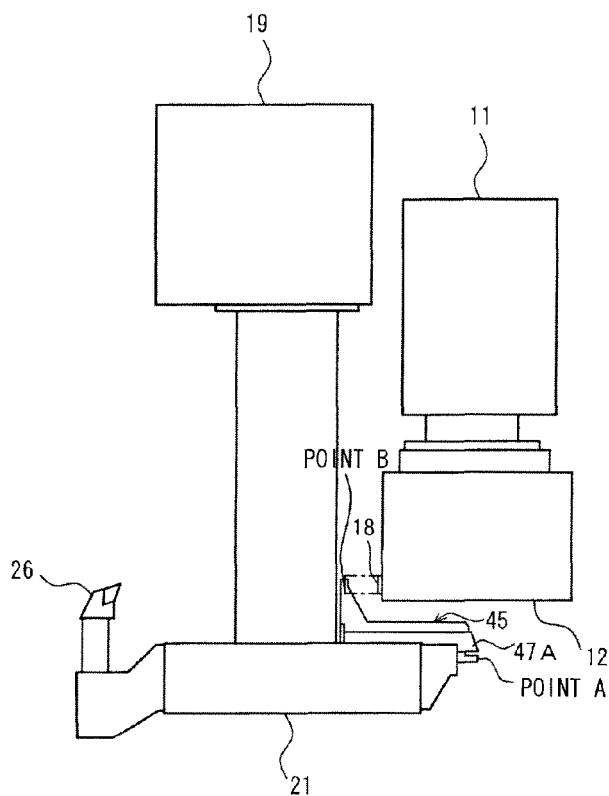
FIG. 23 is a view illustrating a measurement base point A of the turret gauge shown in FIG. 22 and a state of the field of view thereof.
Figure 24:
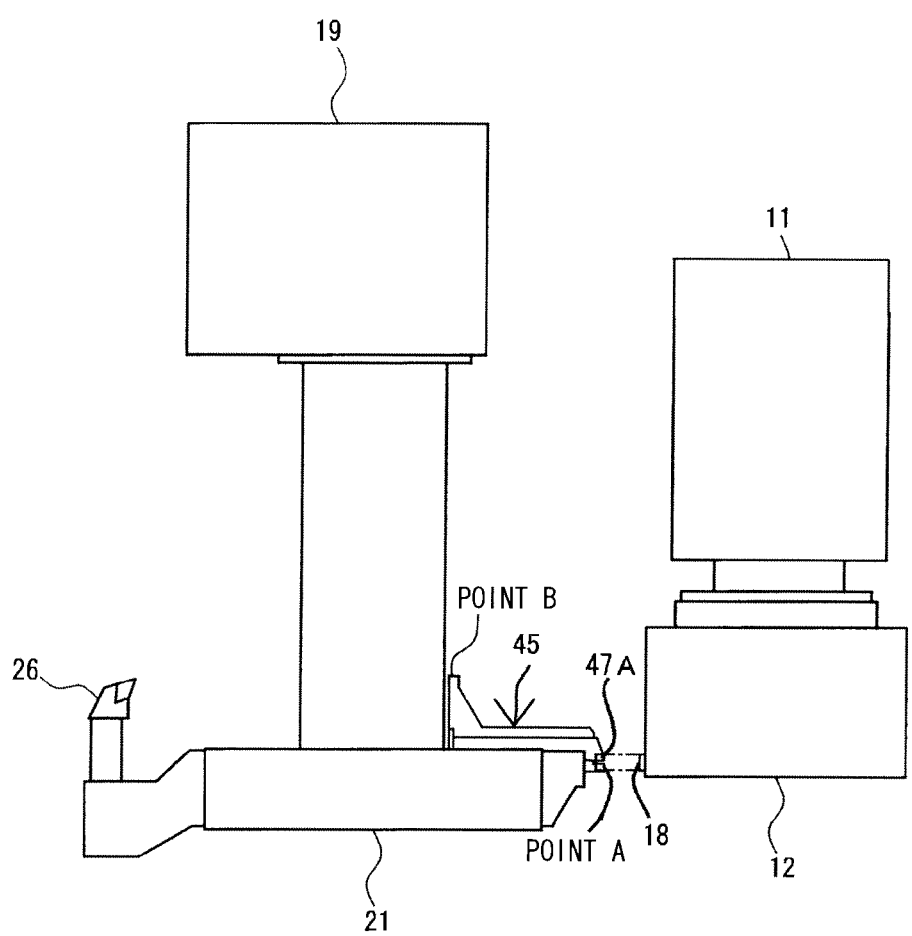
FIG. 24 is a view illustrating a measurement base point B of the turret gauge shown in FIG. 22 and a state of the field of view thereof.
Figure 25:
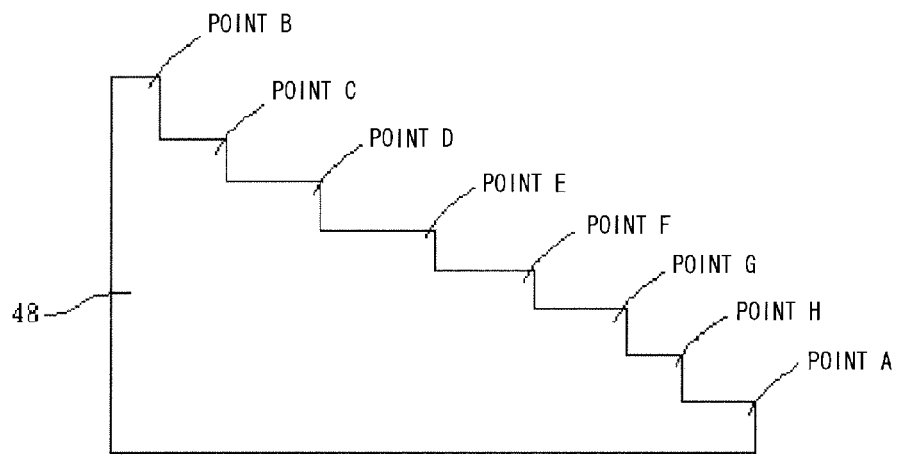
FIG. 25 is a side view illustrating a variation of a gauge main body constituting a turret gauge.

A turret gauge 45 to be placed on the tool post 21 shown in FIG. 20 is configured in such a manner that the check plate 49B is embedded in the turret gauge 45 and that the check plate 49B is flush with the turret gauge 45, as illustrated in FIG. 22. More specifically, the turret gauge 45 is adapted to the placements of the tool post 21 shown in FIG. 23 and FIG. 24. Other configurations and working effects are the same. It should be noted that FIG. 23 corresponds to FIG. 11 of first embodiment, and that FIG. 24 corresponds to FIG. 10 of first embodiment. The gauge main body 48 may have three or more of measurement points (points A to H) as illustrated in FIG. 25. In such a case, heat displacement may vary in several places on the gauge main body 48 (including the case where a ball screw mechanism (not shown) is nonlinearly displaced by heat), and therefore the gauge main body 48 can address each case, and can also detect a heat displacement of the ball screw mechanism with high accuracy.

Third Embodiment

Figure 26:
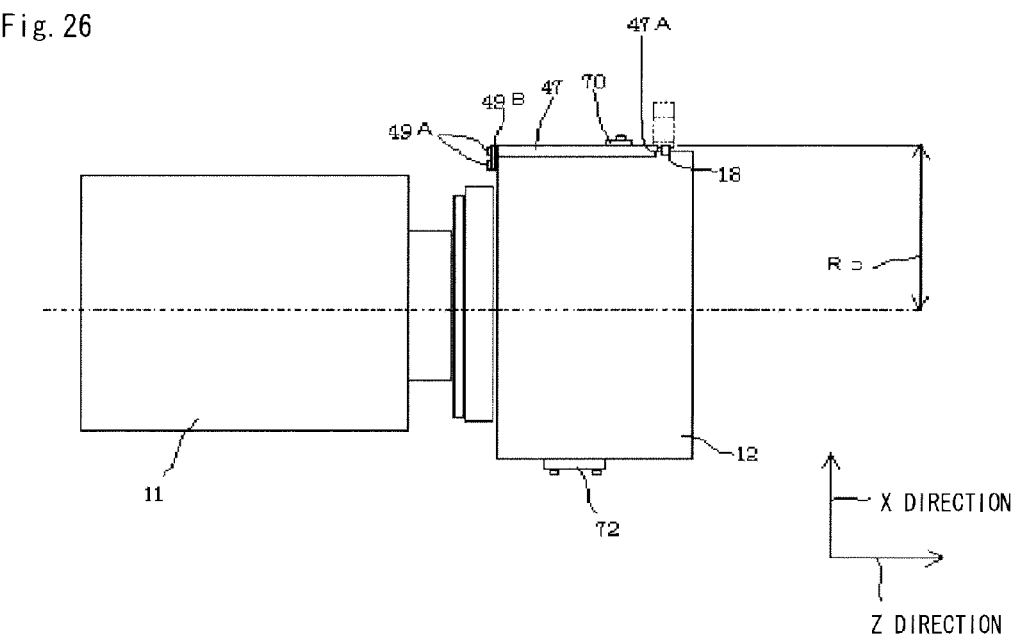
FIG. 26 is a view illustrating a configuration of a principal section of a chuck gauge of third embodiment.

Third embodiment of the present invention will be described using FIGS. 26 to 28. However, substantially the same parts as those in the above-mentioned first embodiment are denoted by the same reference signs to omit or simplify the explanation thereof, and different parts will be mainly described. In third embodiment, as illustrated in FIG. 26, the invar body 47 which is a chuck gauge is arranged on the outer periphery side of the chuck 12 so as to be capable of viewing the whole of the reference gauge 18 and the leading edge 47A of the invar body 47. The invar body 47 (also referred to as chuck gauge in third embodiment) has one end thereof fixed by a pair of bolts 49A through a check plate 49B. Therefore, a stopper 72 for preventing jumping out is arranged on a free end side of the invar body 47 in a state of being slightly separated from the invar body 47. In addition, a counterweight 70 for preventing vibration is arranged on the opposite side of the arrangement position of the invar body 47.

Effects of Present Embodiment

Processes of a mode for setting the initial data of a chuck gauge (represented by CG in FIG. 27) and of a mode for measuring a chuck gauge will be described base on the flow charts shown in FIG. 27 and FIG. 28, respectively.
(Mode for Setting Initial Data of Chuck Gauge)

A mode for setting initial data of the chuck gauge shown in FIG. 26 is a process performed in an adjustment step during manufacturing a machine or during maintenance of the same using the lathe. For example, when the machine is shipped from a factory, a temperature of the chuck gauge 47 is measured by a hand-operated measuring instrument (not shown) with a machine temperature in a stable state.

Figure 27:
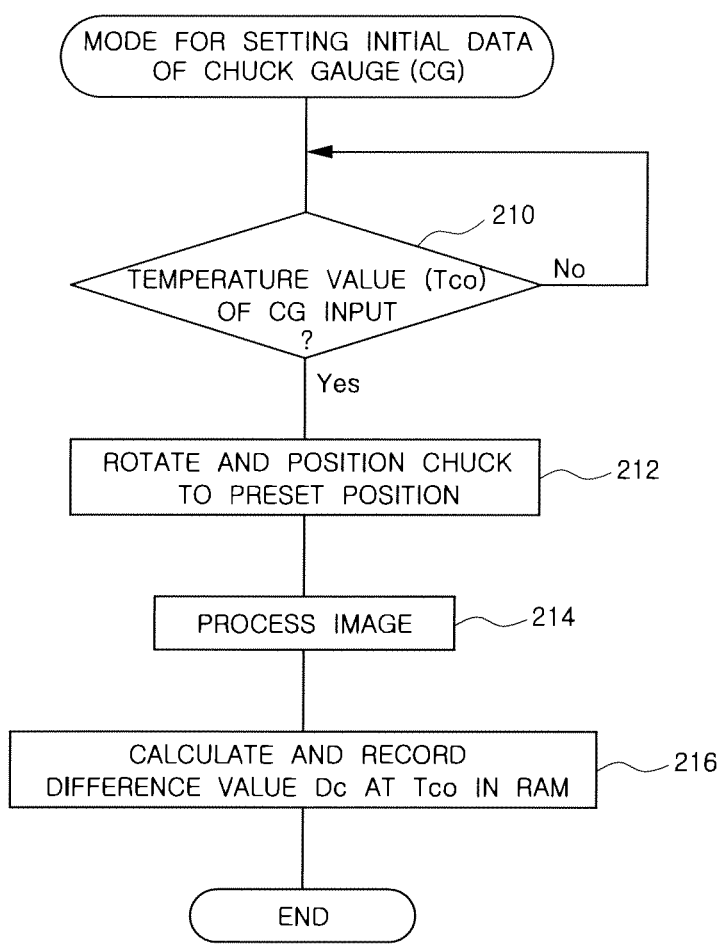
FIG. 27 is a flow chart diagram of a mode for setting initial data of the chuck gauge shown in FIG. 26.

In addition, as illustrated in FIG. 27, in step 210, the CPU 60 shown in FIG. 13 determines whether or not a temperature value of the chuck gauge 47 (a temperature value measured by the hand-operated measuring instrument) Tco has been input. If no in step 210, i.e., if no temperature value Tco has been input, the CPU 60 waits for the input. In this case, the CPU 60 reminds the data input using the display 57 or the buzzer 58 shown in FIG. 13.

If yes in step 210, i.e., if the temperature value Tco has been input, the flow proceeds to step 212, where the CPU 60 rotates and positions the chuck 12 at a preset position. More specifically, the CPU 60 allows the camera apparatus 28 (see FIG. 3) to view the whole of the leading edge 47A of the chuck gauge 47 and the reference gauge 18. The CPU 60, in step 214, performs image processing, and, in step 216, calculates a difference value Dc in a relative difference position of the reference gauge 18 with respect to the leading edge 47A of the invar body 47 at the temperature value Tco, and records the value in the RAM 64.
(Mode for Measuring Chuck Gauge)

Figure 28:
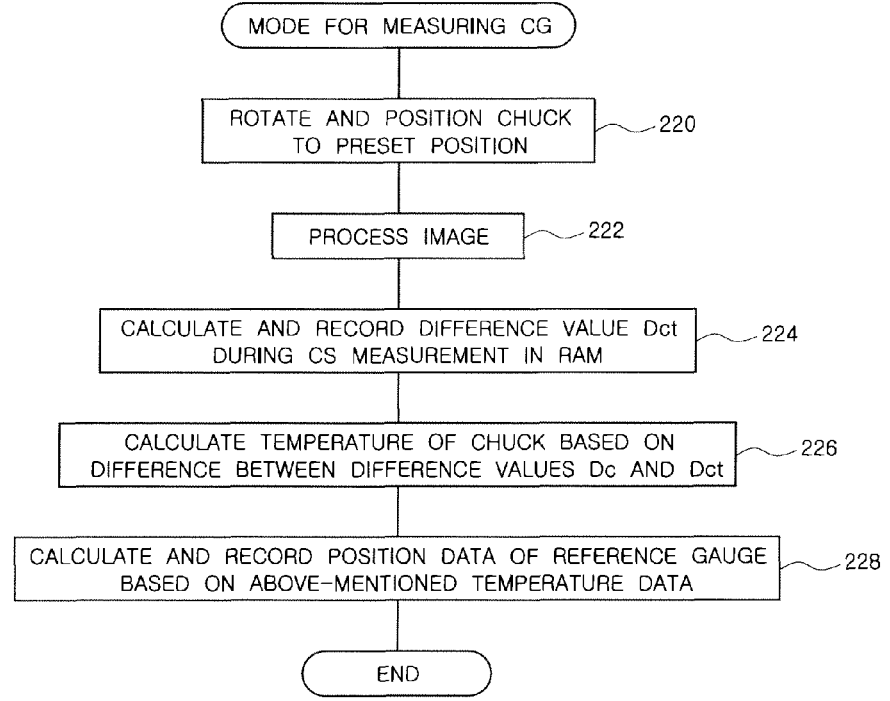
FIG. 28 is a flow chart diagram of a mode for measuring the chuck gauge shown in FIG. 26.

A mode for measuring a chuck gauge shown in FIG. 28 is a process performed during a calibration cycle. As illustrated in FIG. 28, in step 220, the CPU 60 rotates and positions the chuck 12 at a preset position. The CPU 60, in step 222, performs image processing, and in step 224, calculates a difference value Dct in a relative difference position with the reference gauge 18 with respect to the leading edge 47A of the invar body 47 in a calibration cycle CS, and records the value in the RAM 64.

In step 226, based on a difference between the above-mentioned the difference values Dct and Dc (data recorded in the RAM 64 in step 216 in FIG. 27), the CPU 60 calculates a temperature Tc of the chuck 12 at the time of a CS measurement, and records the temperature in the RAM 64. In step 228, the CPU 60 calculates position data of the reference gauge 18 based on the above-mentioned temperature data, and records the position data in the RAM 64. The position data is X direction position data of the reference gauge 18 at the time of the CS measurement, and the X direction position data thereof can be obtained by the formula: Vc (radius position of a reference gauge)=Vcn (radius position of the reference gauge at a specified temperature)+{Tc (temperature of a chuck)−Tco (specified temperature)}*Rc (radius of the reference gauge)*Ac (thermal expansion coefficient of the chuck). Here, a thermal expansion coefficient Ac of the chuck 12 formed with a steel is $1.15*10^{-5}$ (10 to the minus 5th power).

It should be noted that the CPU 60 moves the NC table 50 by driving the NC motor 52 (see FIG. 13) based on the above-mentioned position data of the reference gauge 18.

More specifically, according to third embodiment, even if processing position is displaced due to the heat displacement in the X direction of the chuck 12, the displacement of the processing position thereof can be corrected with high accuracy, and processing accuracy of the workpiece W (see FIG. 1) can be improved. In addition, the above-mentioned measuring mode may be performed before starting the operation of the lathe 5, in which case correction can be made with high accuracy at the time of a so-called cold start as well. Furthermore, third embodiment uses expansion and contraction in a longitudinal direction of the invar body 47, and thus has a simple configuration with high rigidity.

Fourth Embodiment

Figure 29:
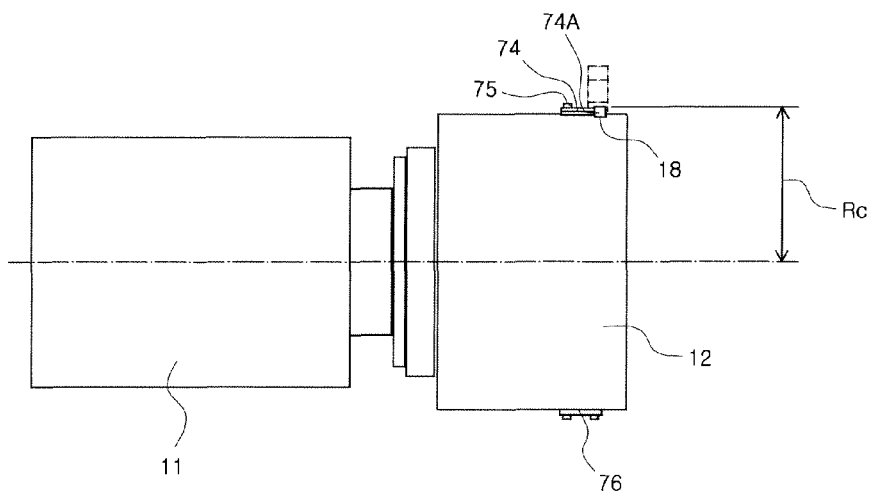
FIG. 29 is a view illustrating a configuration of a principal section of a chuck gauge of fourth embodiment.

Fourth embodiment of the present invention will be described using FIG. 29. However, substantially the same parts as those in the above-mentioned third embodiment are denoted by the same reference signs to omit or simplify the explanation thereof, and different parts will be mainly described. In fourth embodiment, as illustrated in FIG. 29, the bimetal body 74 which is a chuck gauge is arranged on the outer periphery side of the chuck 12 so as to be capable of viewing the whole of the reference gauge 18 and the leading edge 74A of the bimetal body 74. The bimetal body 74 is formed with a combination of two kinds of metal plates with different thermal expansion coefficients, and has one end thereof fixed by a bolt 75. In addition, a temperature of the chuck 12 is measured by processing an image of a relative degree of warpage (synonymous with curvature strain) of the leading edge 74A of the bimetal body 74. The measuring method is performed using a difference value obtained based on the processes in FIG. 27 and FIG. 28.

A counterweight 76 for preventing vibration is arranged on the opposite side of the arrangement position of the bimetal body 74. Fourth embodiment is a bimetal body 74 more compact than the invar body 47 (see FIG. 26), and therefore downsizes a chuck gauge, allows mounting of a collet chuck or the like, which has a smaller mounting portion on an outer peripheral surface than that of a scroll chuck or the like, and makes a counterweight 76 smaller than that of the example in FIG. 26. Other configurations and working effects are the same as those of third embodiment.

Figure 30:
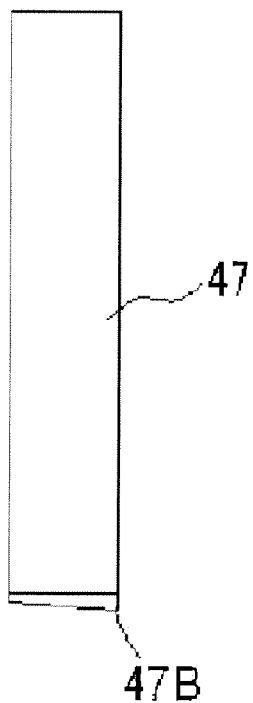
FIG. 30 is a view illustrating another variation of a reference body according to the present invention, such as an invar body.
Figure 31:
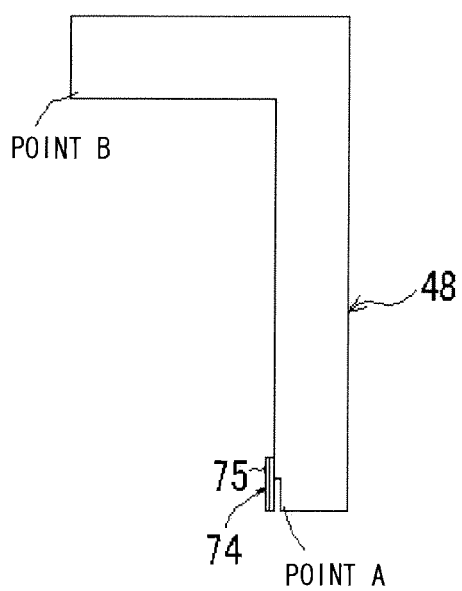
FIG. 31 is a view illustrating another variation of a reference means according to the present invention, such as a turret gauge.

It should be noted that the invar body according to first embodiment and second embodiment may be, as illustrated in FIG. 30, configured integrally by joining, by brazing or the like, a leading edge 47B made of a steel to the invar body 47 formed in a rectangular parallelepiped shape. The turret gauge according to first embodiment and second embodiment may be, as illustrated in FIG. 31, configured so as to mount the bimetal body 74 (see FIG. 29) on the gauge main body 48 (see FIG. 8 and FIG. 22). In this case again, the same working effects as that of first and second embodiments can be obtained. The chuck 12 adopting the present invention may be configured so as to have an outer shape thereof formed in a conical shape or the like and to reduce inclusion of swarf or the like. In addition, the present invention can arbitrarily select, for example, a combination of the configuration of third embodiment or fourth embodiment with that of first embodiment or second embodiment. Furthermore, the process flow of the above-mentioned program (see FIG. 14, etc.) is one example, and may be appropriately varied without departing from the scope of the present invention. For example, in the mode for processing a tool bit image (see FIG. 18), the CPU 60 may be configured so as to record breakage data or the like in the RAM 64, or provide a feedback and perform a compensation process if expansion or the like is less than or equal to a set value.

The measuring apparatus (an apparatus provided with at least a camera, a memory such as RAM, a CPU, and, for example, an invar body) according to the present application can accurately measure a temperature of an object to be measured by imaging the object to be measured, which is arranged in parallel to an invar body at a position approximately 10 m apart, using a telephoto lens arranged in the camera. More specifically, the temperature of the object to be measured can be measured from a distant point in a noncontact state without any connection by wiring or the like, so that the need of a member for a wiring connection, for example, a brush holder can be eliminated, and that the configuration of the measuring apparatus can be simplified. In addition, the measuring apparatus according to the present invention is also applicable to other machines than a cutting machine.

Fifth Embodiment

Hereinafter, an imaging apparatus and a cutting machine provided with the imaging apparatus, which are fifth embodiment of the present invention, will be described based on FIGS. 32 to 36. In addition, substantially the same parts as those in the above-mentioned first embodiment are denoted by the same reference signs to omit or simplify the explanation thereof, and different parts will be mainly described. Fifth embodiment is an example where an imaging apparatus 127 which is an imaging means is arranged slidably along a Z direction (horizontal direction), and where an unchanged range of a pixel region (synonymous with the range of an imaging area) of an image pickup device 30A can be effectively used without reducing the imaging area of the camera 30 by, for example, dividing.

(Configuration of Imaging Apparatus 127)

Figure 32:
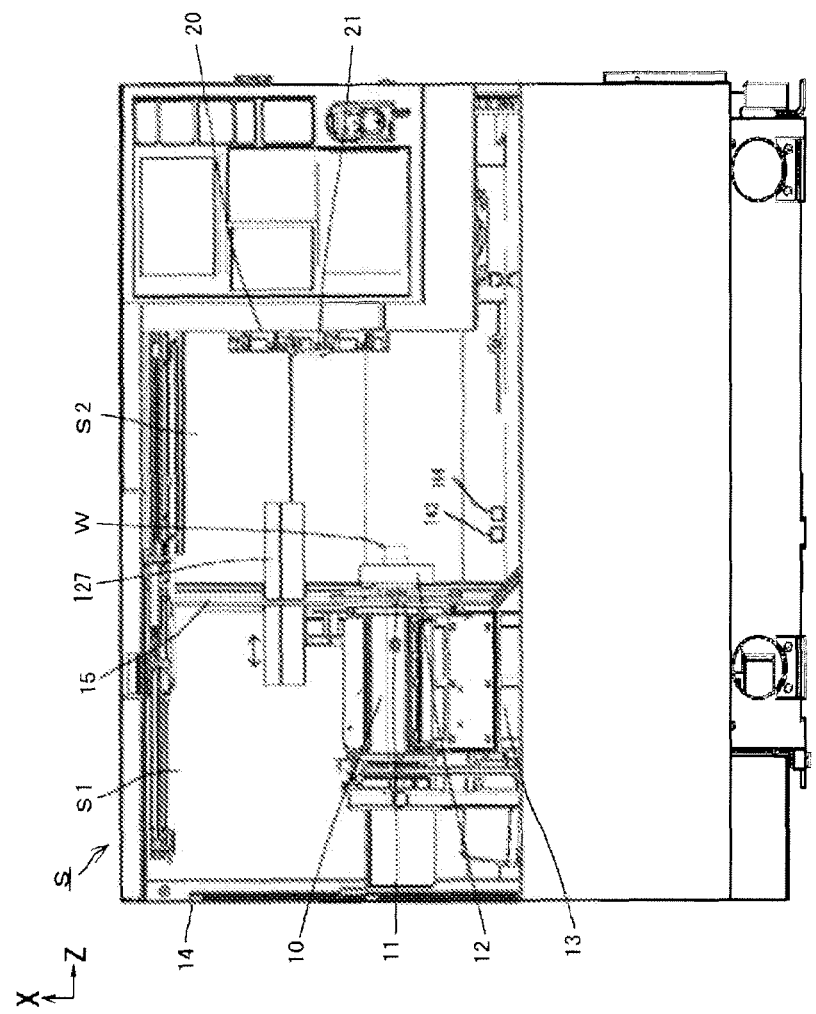
FIG. 32 is a front view illustrating a single-spindle turret lathe of fifth embodiment.
Figure 33:
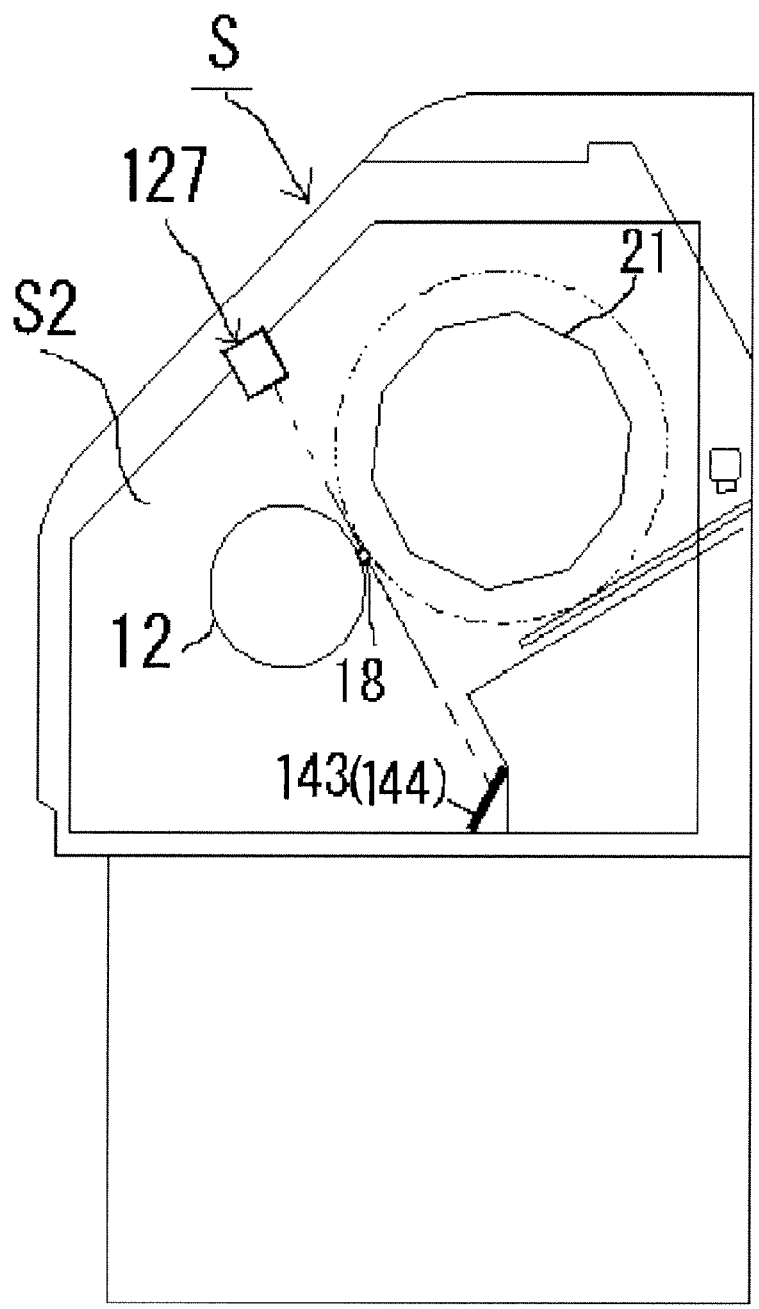
FIG. 33 is a side view illustrating a principal section of the turret lathe shown in FIG. 32.
Figure 35:
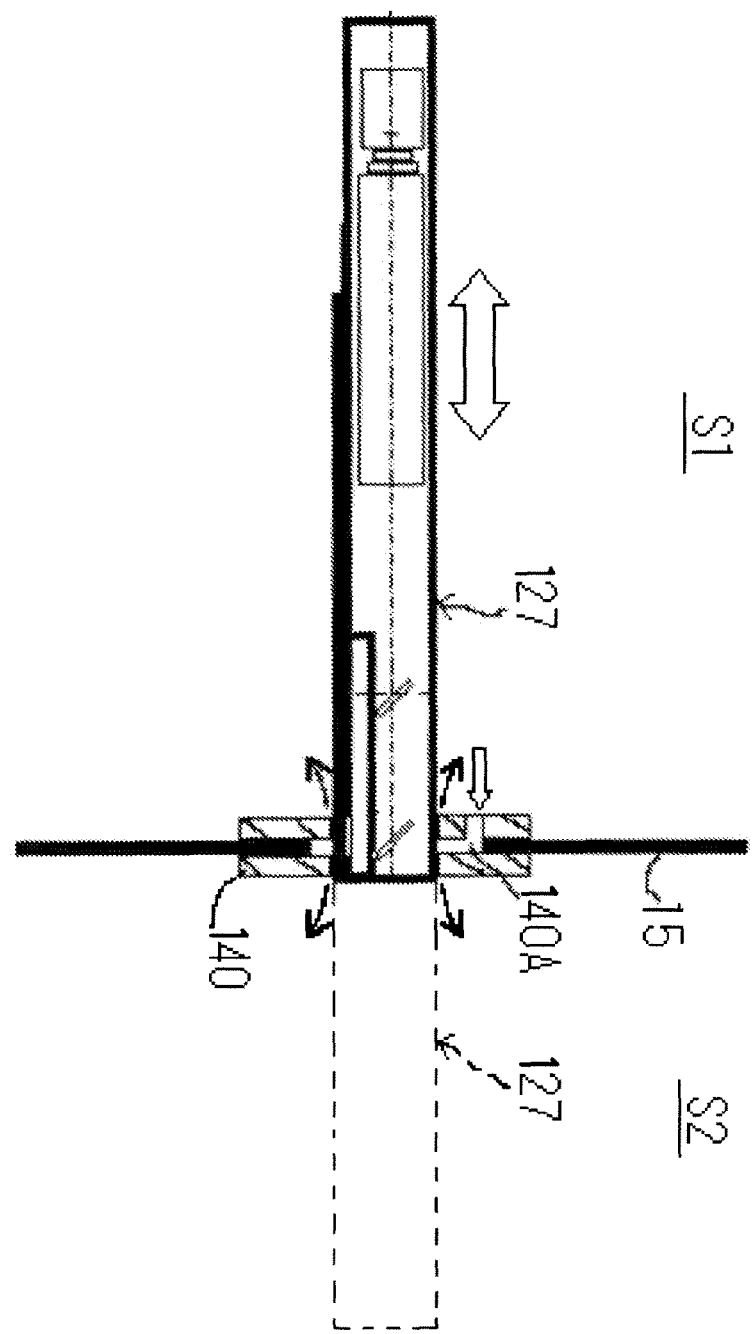
FIG. 35 is an end view illustrating a state in which the imaging apparatus shown in FIG. 34(A) is arranged on a partition wall.

As illustrated in FIG. 32 and FIG. 33, in the lathe S, the imaging apparatus 127 is slidably arranged between an isolating zone S1 and a processing zone S2 (see FIG. 35). This imaging apparatus 127 images chips 25A, 26A (see FIG. 36) or the like of cutting tools (hereinafter, also referred to as tool bit) 25, 26, which are to be a subject. More specifically, the imaging apparatus 127 slides to a processing zone S2 side when imaging the chips 25A, 26A or the like, and slides to the isolating zone S1 side when the imaging is completed. In addition, image data imaged by the imaging apparatus 127 is configured so as to be output to the CPU 60 shown in FIG. 13. In addition, the CPU 60 collates/calculates displacement or the like of chips 25A, 26A, and corrects a processing position of a cutting tool based on those results.

As illustrated in FIG. 34(A), a housing 127A of the imaging apparatus 127 is partitioned into an imaging space (also referred to as lens chamber) 128A and a dust-proof space (also referred to as shutter chamber) 128B. In particular, for example, a camera of five million pixels (including a CCD 30A which is an image pickup device) 30, an imaging lens body 29, a full mirror 31A, and a half mirror 31 are housed in the lens chamber 128A of the rectangular tube-shaped housing 127A. This half mirror 31B is arranged between the imaging lens body 29 and the full mirror 31A, and is a mirror which reflects and transmits a part of incident light of a subject. In addition, examples of the half mirror 31B (also referred to as beam splitter) include mirrors of a flat plate type, a prism type, a wedge substrate type and the like.

The full mirror 31A and the half mirror 31B mentioned above are disposed in such a manner that the fields of view of their respective imaging optical systems can be of the same size. More specifically, the full mirror 31A and the half mirror 31B are disposed so as to alternately image their respective subjects. For example, the full mirror 31A and the half mirror 31B are configured in such a manner that when a subject (chip) 23A which is indicated by a chain double-dashed line in FIG. 34(A) is imaged by the full mirror 31A, an optical path of the half mirror 31B is blocked, and when a subject (chip) 24A is imaged by the half mirror 31B, an optical path of the full mirror 31A is blocked.

Figure 34:
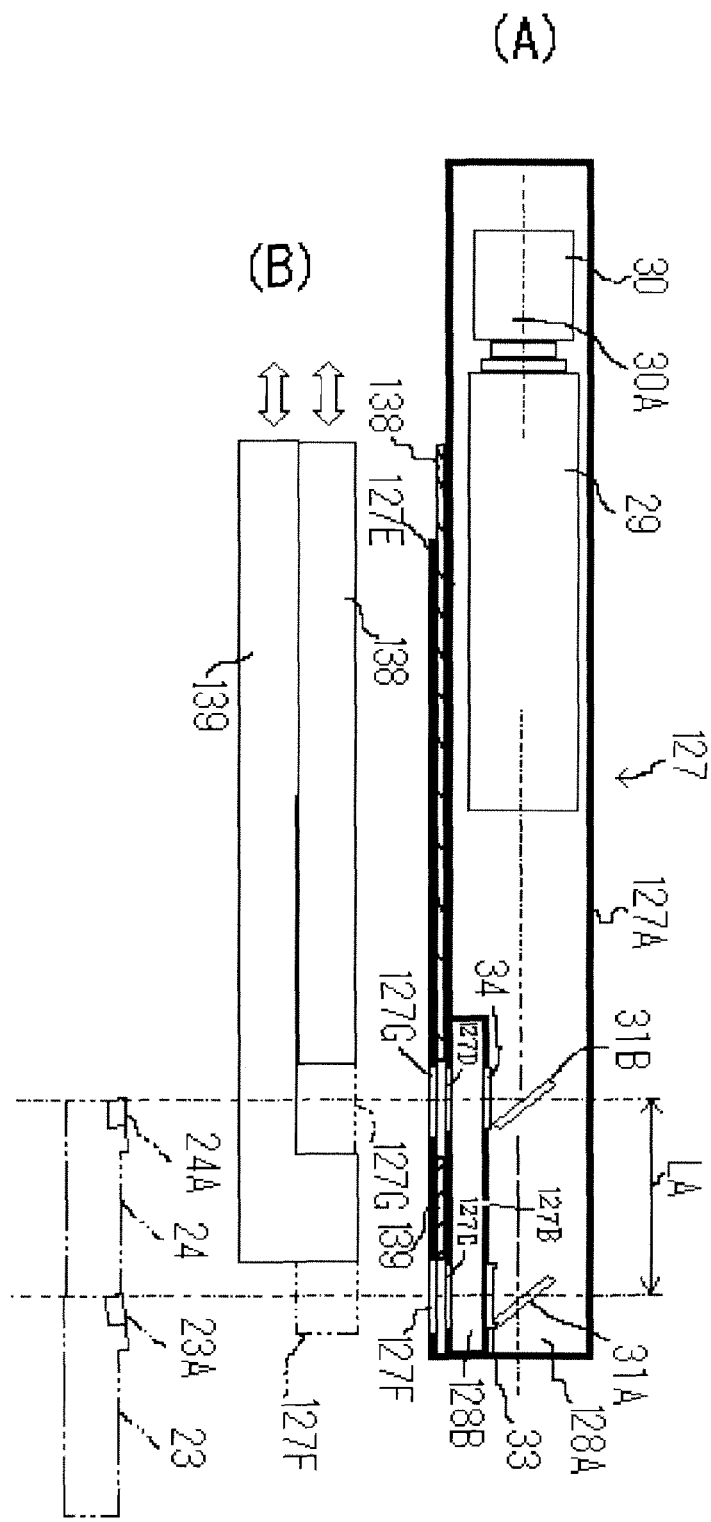
FIG. 34 is a view pertaining to an imaging apparatus shown in FIG. 33.

Therefore, each of optical paths between the imaging lens body 29 of the camera 30 and two subjects (for example, tool bits 23, 24, etc.) is bent at a right angle by each of a pair of the mirrors 31A and 31B respectively, so that each subject is imaged in the range of one field of view area (synonymous with imaging area). In addition, as illustrated in FIG. 34, for example, the chip 23A of the tool bit 23 is first imaged in one field of view area, and then the chip 24A of the tool bit 24 is subsequently imaged in one field of view area. It should be noted that the field of view area has a size of 17 mm (2000 pixels) in a short side and 21.5 mm (2500 pixels) in a long side in the case of using a camera of five million pixels A focusing lens 33 is arranged on an optical path corresponding to the full mirror 31A, and a transparent protective glass 34 is arranged on an optical path corresponding to the half mirror 31B, respectively, between the lens chamber 128A and the shutter chamber 128B. Here, the focusing lens 33 is for adjusting a focal length LA (for example, 100 mm) between two series. It should be noted that imaging space is always kept at a predetermined air pressure such as +0.05 MPa.

In addition, a hole 127B is formed between the lens chamber 128A and shutter chamber 128B, so that compressed air (hereinafter, also referred to as air) is sent out from this hole 127B to the shutter chamber 128B. More specifically, the shutter chamber 128B is always pressurized to a lower pressure than that of the lens chamber 128A, such as +0.11 MPa. Therefore, the shutter chamber 128B is pressurized, thereby preventing coolant, swarf or the like from flowing into the shutter chamber 128B. It should be noted that an air connection port (not shown) is arranged in the lens chamber 128A, and that an air passage for supplying air generated by a compressor (not shown) lies between this air connection port and the compressor. In addition, the air continues injecting to the lens chamber 128A at all times.

Apertures 127C and 127D are formed in the positions facing the focusing lens 33 and the protective glass 34 of the shutter chamber 128B, respectively. Shutters 138 and 139 which are switching means are slidably arranged between the housing 127A and a supporting piece 127E thereof to open and close the aperture 127C or 127D, respectively. More specifically, the shutter 138 and 139 for blocking the optical paths are configured so as to slide using the air supplied through the above-mentioned air passage. In addition, apertures 127F and 127G are formed in the supporting piece 127E so as to face the apertures 127C and 127D, respectively.

As illustrated in FIG. 34(B), the shutter 138 has a strip-shape plane, and the shutter 139 has a substantially L-shaped plane. In addition, the shutters 138 and 139 move, facing the apertures 127G and 127F, to open and close the apertures 127C and 127D.

More specifically, the shutters 138 and 139 open their respective optical path, so that the camera 30 can image the chips 23A, 24A of the cutting tools 23, 24 shown in FIG. 34 (indicated by a chain double-dashed line in the FIGS.) which are to be their subjects. In addition, the shutters 138 and 139 closes for the purpose of preventing coolant, swarf or the like from flowing into the shutter chamber 128B. In addition, the shutters 138 and 139 closes normally, and do not open the optical paths at the same time. It should be noted that, for example, a liquid crystal shutter which opens and closes by switching on/off of voltage, or an optical path switching mechanism may be used as a shutter.

As illustrated in FIG. 32 and FIG. 33, light sources 143 and 144 for illumination are arranged at positions on the optical paths facing the mirrors 31A and 31B (see FIG. 34) of the imaging apparatus 127, respectively. These light sources 143 and 144 comprise, for example, a light-emitting LED.

(Schematic Configuration of Sliding Mechanism of Imaging Apparatus 127)

As illustrated in FIG. 32 and FIG. 35, an imaging apparatus 127 is arranged at a predetermined place of a partition wall 15, with a sliding mechanism (not shown) (for example, a cylinder activated by the air supplied through the air passage) coupled thereto. Therefore, as mentioned above, the imaging apparatus 127 slides between the isolating zone S1 and the processing zone S2, and slides back to the isolating zone S1 from the processing zone S2 just before cutting. The reasons for sliding back the imaging apparatus 127 are to prevent interference with a tool bit or the like mounted on the turret apparatus 20 for cutting, to avoid the imaging apparatus 127 from visually impeding an operator during a cutting operation, and to improve workability.

Furthermore, as illustrated in FIG. 35, a seal cover 140 made of a synthetic resin (for example, a urethane rubber) is arranged between the imaging apparatus 127 and the partition wall 15. More specifically, the imaging apparatus 127 is held in a state of being fit into the seal cover 140. This seal cover 140 is intended to prevent the imaging apparatus 127 from picking swarf in the processing zone or the like during sliding, and to prevent a coolant from seeping into the isolating zone S1.

In addition, an induction opening 140A surrounding the imaging apparatus 127 is opened, so that air is sent out from the air passage (not shown) to the induction opening 140A (see the arrow in FIG. 35), and is blown out from a clearance between the imaging apparatus 127 and the seal cover 140 (see the bold line arrows of FIG. 35).

It should be noted that the leading edge of the imaging apparatus 127 (a portion facing the seal cover 140) has been set in advance so as to slightly protrude from the seal cover 140 into the processing zone S2 or to be flush therewith, in a position where the imaging apparatus 127 backs off to the isolating zone S1 (a waiting position shown by a solid line in FIG. 35).

(Schematic Configuration of Chuck)

Figure 36:
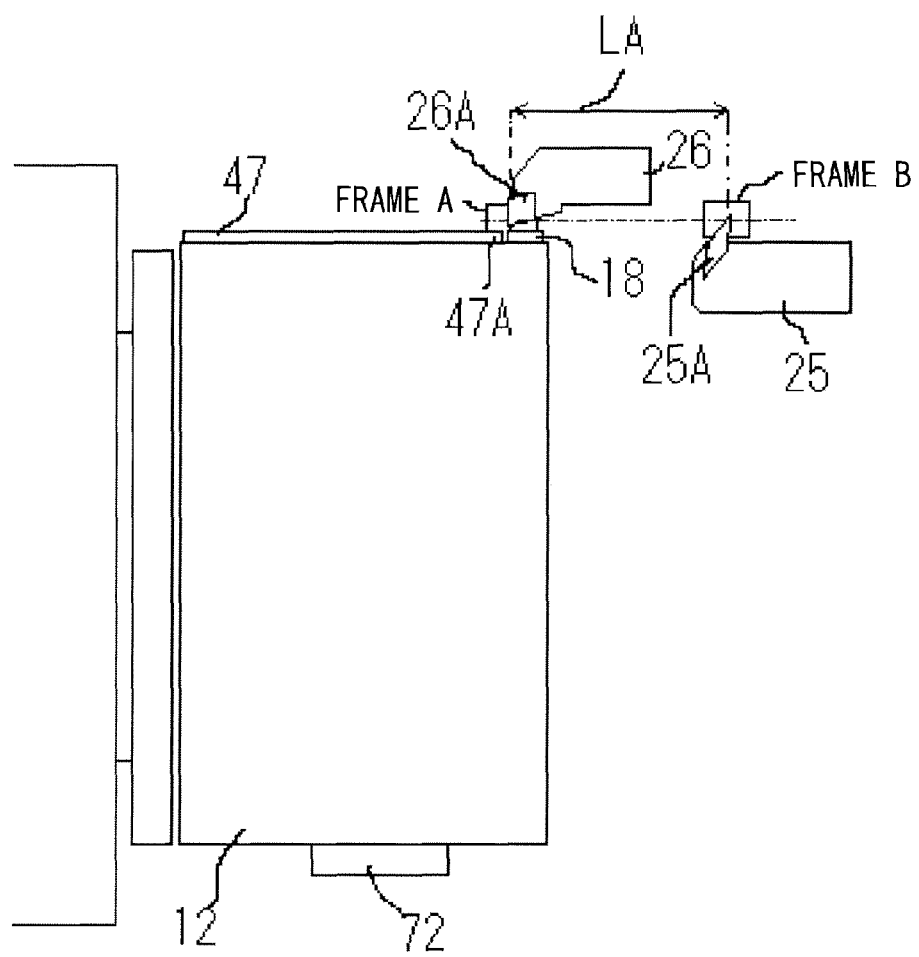
FIG. 36 is a view illustrating a positional relationship when a tool bit or a reference gauge and an invar body are included in a camera view and imaged by a camera shown in FIG. 34.

As illustrated in FIG. 36, the invar body 47 which is a reference body is arranged so as to face the above-mentioned reference gauge 18 on the outer periphery side of the chuck 12. More specifically, the invar body 47, the reference gauge 18, and the tool bit 26 are arranged in such a manner that the leading edge 47A of the invar body 47, the reference gauge 18, and the chip 26A of the tool bit 26 can be included and imaged (synonymous with viewing the whole) in the field of view area of the imaging apparatus 127. More specifically, the tool bit 26 has been set in advance so as to move to a predetermined position in a whole-viewing area A (referred to as "frame A" in FIGS.) of the imaging apparatus 127 during detection of a chip, and a tool bit 25 has been set in advance so as to move to a predetermined position in a whole-viewing area B (referred to as "frame B" in FIGS.) of the imaging apparatus 127 during detection of a chip.

The invar body 47 is formed in, for example, a prismatic shape using a material (for example, an invar which is an invariable steel) with a smaller thermal expansion coefficient than that of a heat-treated steel constituting the lathe S (see FIG. 32). In addition, the invar body 47 has one end thereof (not shown) fixed by a fastening member (such as a bolt). Therefore, a stopper for preventing jumping out (not shown) is arranged on a free end side of the invar body 47 in a state of being slightly separated from the invar body 47. In addition, a counterweight 72 for preventing vibration is arranged on the opposite side of the arrangement position of the invar body 47. More specifically, the example of FIG. 36 has substantially the same configuration as that of FIG. 26 of third embodiment.

Effects of Present Embodiment

During detection of a chip, as illustrated in FIG. 36, if the reference gauge 18, and the chip 25A or 26A of the tool bit 25 or 26 are included and imaged in a field of view area of the camera 30, the top surfaces of the reference gauge 18 and the cutting edge 25A or 26A of the tool bit 25 or 26 are aligned at the same height.

In addition, during detection of a chip, as illustrated in FIG. 35, the imaging apparatus 127 is slid from the isolating zone S1 to the processing zone S2, and the light sources 143 and 144 shown in FIG. 32 are made to emit light. Then, when the chip 26A of the tool bit 26 shown in FIG. 36 is detected, the imaging apparatus 127 at an imaging position (in a state indicated by the dashed line of FIG. 35) slides the shutter 138 and opens an optical path on the half mirror 31B side, as illustrated in FIG. 34. The camera 30 images the leading edge 47A of the invar body 47, the reference gauge 18, and the chip 26A of the tool bit 26, which are subjects positioned in the whole-viewing area A. More specifically, since an optical path on the shutter 139 side is blocked, the half mirror 31B reflects light of the subjects in the whole-viewing area A to the camera 30.

Meanwhile, when the chip 25A of the tool bit 25 shown in FIG. 36 is detected (in this case, the tool bit 26 is not present in the whole-viewing area A), the shutter 138 is first slid to open an optical path on the half mirror 31B side, as illustrated in FIG. 34. The camera 30 images the leading edge 47A of the invar body 47, and the reference gauge 18, which are subjects positioned in the whole-viewing area A. More specifically, since an optical path on the shutter 139 side is blocked, the half mirror 31B reflects light of the subjects in the whole-viewing area A to the camera 30.

Immediately after imaging, an optical path on the full mirror 31A side is opened by closing the shutter 138 and sliding the shutter 139. Switching between the shutters 138 and 139 is performed at a time difference which is a moment of switching therebetween (synonymous with approximately the same time), for example, 0.5 seconds. In addition, in order to reduce an impact at the time of closing and opening the shutter 138 or 139, loads of the shutters 138 and 139 are reduced, and the shutters 138 and 139 are driven by air or the like.

Then, as illustrated in FIG. 36, the camera 30 images the chip 25A of the tool bit 25 which is a subject positioned in the whole-viewing area B. More specifically, since an optical path on the shutter 138 side is blocked, the full mirror 31A reflects light of the subject in the whole-viewing area B to the camera 30. In this case, the half mirror 31B transmits light of the subject, which is reflected by the full mirror 31A, so that the camera 30 images only the subject in the whole-viewing area B.

In the present embodiment, the shutter 138 or 139 is opened and closed in a time considered to be a moment (time difference in switching optical paths), so that there is no variation between positions of subjects at the time of imaging, and that the leading edge 47A of the invar body 47, the reference gauge 18, and the chip 25A of the tool bit 25 can be imaged in a state which can be substantially considered as viewing the whole thereof. More specifically, according to the present embodiment, for example, five million pixels (imaging range of 17 mm in a short side and 21.5 mm in a long side) can be effectively used as they are without reducing the imaging area (synonymous with image recognition area) of the camera 30 by, for example, dividing, so that image recognition can be improved.

In addition, according to the present embodiment, the whole-viewing area B and the whole-viewing area A of the camera 30 can be separated from each other for a predetermined distance LA (see FIG. 34 and FIG. 36), so that a type of a tool bit, such as an inner diameter tool bit, an outer diameter tool bit or other special tool bits can be imaged in a state which can be substantially considered as viewing the whole thereof, without separately providing, for example, a reference gauge for an inner diameter tool bit. Moreover, according to the present embodiment, the whole-viewing area B and the whole-viewing area A are separated from each other for a predetermined distance LA (for example 100 mm), so that interference by an inner diameter tool bit 25, for example, can be prevented.

At the time of cutting, air is sent out from an air passage (not shown) to the induction opening 140A of the seal cover 140 shown in FIG. 35, and then the imaging apparatus 127 is slid to the isolating zone S1 (see the solid line of FIG. 35). More specifically, as illustrated in FIG. 35, just before the imaging apparatus 127 returns to a waiting position, air is blown out from a clearance between the imaging apparatus 127 and the seal cover 140, thereby preventing a coolant, swarf or the like in the processing zone S2 from being included in the isolating zone S1. Then, after the imaging apparatus 127 returns to the waiting position, the sending of the air from the air passage to the induction opening 140A of the seal cover 140 is terminated.

In addition, the edges of the chips 25A, 26A shown in FIG. 36 can be obtained using, for example, a seek line. This seek line is a line segment free in a length and a slope that are set in a two-dimensional virtual screen, and is intended to obtain an position of an edge with respect to a center position in a line direction thereof.

Sixth Embodiment

Sixth embodiment of the imaging apparatus according to the present invention will be described using FIG. 37. However, substantially the same parts as those of the imaging apparatus 127 shown in FIG. 34 of the above-mentioned fifth embodiment are denoted by the same reference signs to omit or simplify the explanation thereof, and different parts will be mainly described.

Figure 37:
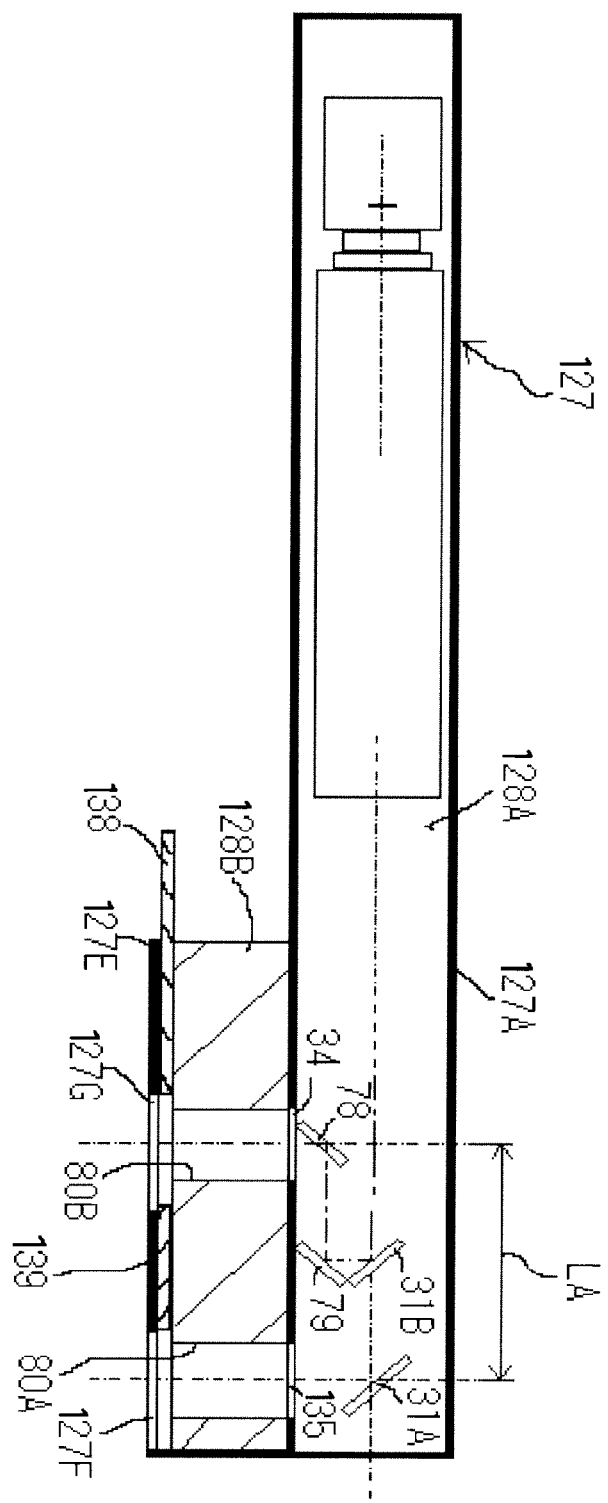
FIG. 37 is an end view of an imaging apparatus according to sixth embodiment.

Sixth embodiment is an example of a configuration where an optical path is folded back in such a manner that an optical path of a half mirror is at the same length as that of a full mirror, as illustrated in FIG. 37. More specifically, the present embodiment is an example of preventing one screen size from being smaller or larger than the other screen size in the case where optical path lengths are different from each other.

In particular, the half mirror 31B is arranged on the full mirror 31A side, interposing therebetween the half (for example, 50 mm) of a predetermined distance LA between the whole-viewing area B and the whole-viewing area A (see FIG. 36). A pair of full mirrors for folding back (hereinafter, also simply referred to as "folding back mirror") 78 and 79 are arranged in parallel so as to incline in the same direction, and lead incident light of a subject to the half mirror 31B. More specifically, the folding back mirror 78 folds back an optical path on the protective glass 34 side to a mirror 79 to lead light to the half mirror 31B. Therefore, the folding back mirror 79 is arranged so as to face the half mirror 31B.

In addition, since the optical paths of both the half mirror 31B and the full mirror 31A are at the same length, a protective glass 135 instead of a focusing lens is arranged on the shutter chamber 128B along the optical path on the full mirror 31A side. The shutter chamber 128B of the present embodiment is arranged outside of the housing 127A. In addition, the shutter chamber 128B has holes 80A and 80B for optical paths formed so as to correspond to the folding back mirror 78 and the full mirror 31A, respectively.

It should be noted that a pair of the shutters 138 and 139 for switching optical paths have a shorter longitudinal length than that of fifth embodiment. The reason for individually operating the shutters 138 and 139 only at the time of imaging is to enhance a dust-proof effect by closing the hole 80A or 80B of the shutter chamber 128B except for at the time of imaging.

In the present embodiment, the folding back mirrors 78 and 79 are interposed in front of the half mirror 31B, so that the optical path of the half mirror 31B is at the same length as that of the full mirror 31A. More specifically, according to the present embodiment, the optical paths of both the half mirror 31B and the full mirror 31A are at the same length, thereby eliminating the need of a focusing lens for focus correction.

In addition, compared to the case where optical path lengths are different (that is, screen sizes are different), the present embodiment eliminates the need to make screen sizes uniform, thereby making software simpler. More specifically, according to the present embodiment, the pixel sizes of the whole-viewing area B and the whole-viewing area A shown in FIG. 36 are the same, thereby simplifying image processing using an algorithm. Other configurations and working effects are the same as those of fifth embodiment.

It should be noted that the need to switch the shutters at the time of imaging can be eliminated by separately switching the light source 143 or 144 shown in FIG. 32 to be turned on. In this case, there may be only one shutter.

Seventh Embodiment

Figure 38:
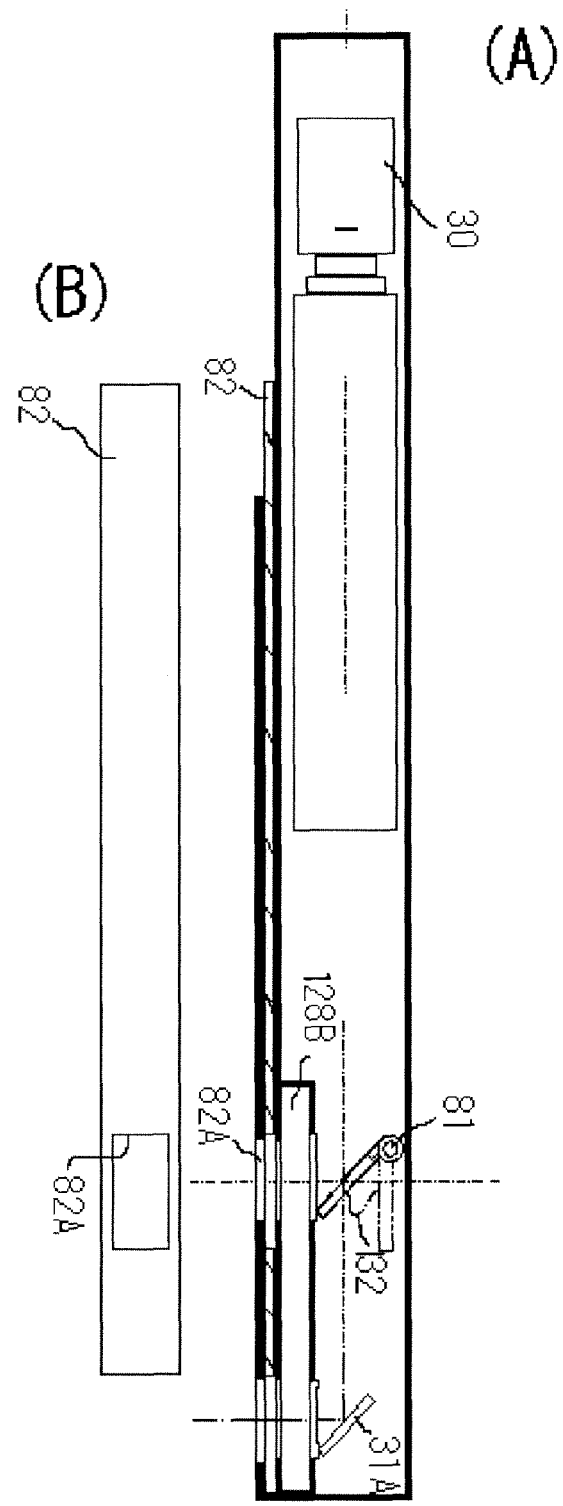
FIG. 38 is a view pertaining to an imaging apparatus according to seventh embodiment.

Seventh embodiment of the imaging apparatus according to the present invention will be described using FIG. 38. However, substantially the same parts as those of the imaging apparatus 127 shown in FIG. 34 of the above-mentioned fifth embodiment are denoted by the same reference signs to omit or simplify the explanation thereof, and different parts will be mainly described. Seventh embodiment is an example where the full mirrors 31A and 132 are used as a pair of mirrors, and the full mirror 132 on the camera 30 side is made to be rotatable, as illustrated in FIG. 38(A).

In particular, a rotation apparatus 81 is coupled to the full mirror 132 on the camera 30 side. When a subject on the full mirror 31A side (in the whole-viewing area B) is imaged, the full mirror 132 is rotated through the rotation apparatus 81 and retreated from the optical path of the full mirror 31A and the camera 30, so as to be positioned in a retreat position indicated by a chain double-dashed line.

Meanwhile, when a subject on the full mirror 132 side (in the whole-viewing area A) is imaged, the full mirror 132 is rotated through the rotation apparatus 81 so as to be positioned in an imaging position of a predetermined angle shown by a solid line, before the subject in the whole-viewing area A is imaged. In this case, light of a subject from the full mirror 31A is blocked by the full mirror 132, so that imaging is not performed.

It should be noted that in the present embodiment, a stopper (not shown) is arranged in such a manner that the full mirror 132 can temporarily stop at each of the imaging position and the retreat position. In addition, a driving means of a rotation apparatus may be configured as a stepping motor or the like so as to stop the full mirror 132 at a predetermined angle.

In the present embodiment, the full mirror 132 is rotatably arranged, and accordingly optical paths are switched respectively. More specifically, according to the present embodiment, the optical paths are switched respectively according to the rotation of the full mirror 132, and therefore there may be only one shutter 82.

Therefore, as illustrated in FIG. 38(B), the one shutter 82 has a rectangular hole 82A formed at a portion corresponding to the full mirror 132. More specifically, the shutter 82 is not a means for switching optical paths, but is only for preventing a coolant, swarf or the like from entering in the shutter chamber 128B. Other configurations and working effects are the same as those of fifth embodiment.

Eighth Embodiment

Figure 39:
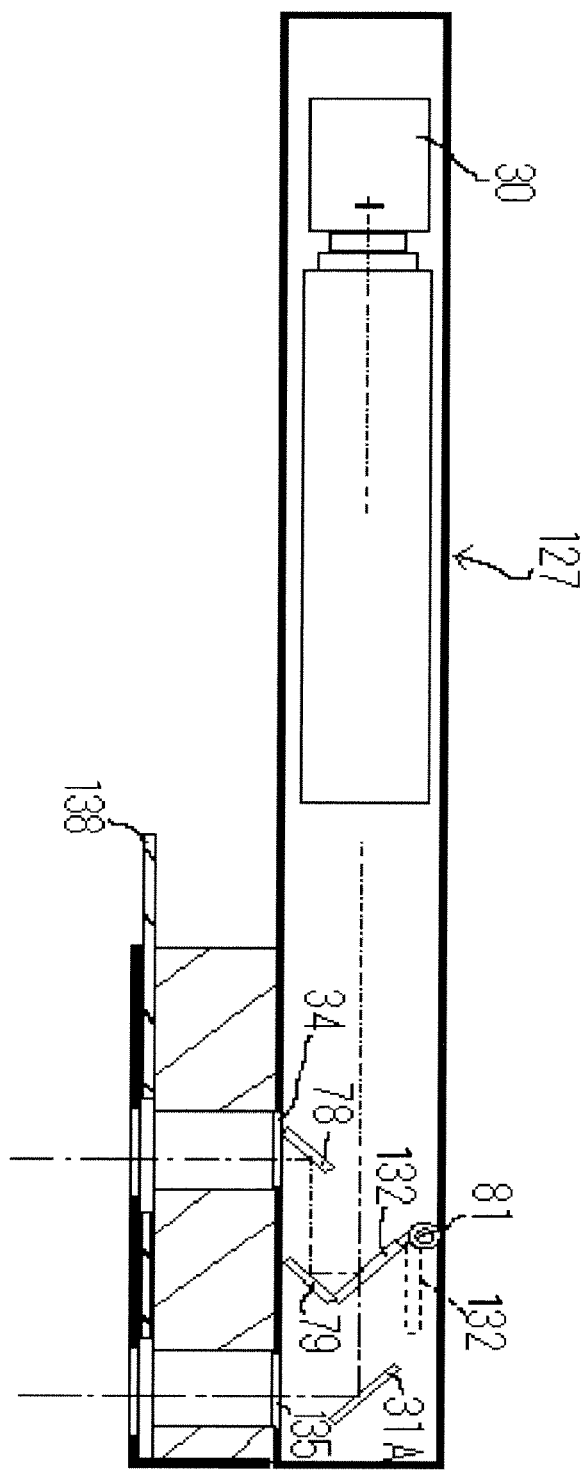
FIG. 39 is an end view of an imaging apparatus according to eighth embodiment.

Eighth embodiment of the imaging apparatus according to the present invention will be described using FIG. 39. However, substantially the same parts as those of the imaging apparatus 127 shown in FIG. 37 of the above-mentioned sixth embodiment are denoted by the same reference signs to omit or simplify the explanation thereof, and different parts will be mainly described. Eighth embodiment is an example of a combination of sixth and seventh embodiments, as illustrated in FIG. 39.

In particular, the present embodiment is configured in such a manner that the full mirrors 31A and 132 are used as a pair of mirrors, that the full mirror 132 on the camera 30 side is made to be rotatable, and that an optical path is folded back in such a manner that the optical path of the full mirror 132 by the camera 30 is at the same length as that of the full mirror 31A.

Therefore, according to the present embodiment, the optical paths of both the full mirrors 132 and 31A are at the same length, thereby eliminating the need of a focusing lens for focus correction. In addition, according to the present embodiment, the pixel sizes of the whole-viewing area B and the whole-viewing area A shown in FIG. 36 are the same, thereby simplifying image processing using an algorithm. Furthermore, according to the present embodiment, the optical paths are switched respectively according to the rotation of the full mirror 132, and therefore there may be only one shutter 138.

Ninth Embodiment

Figure 40:
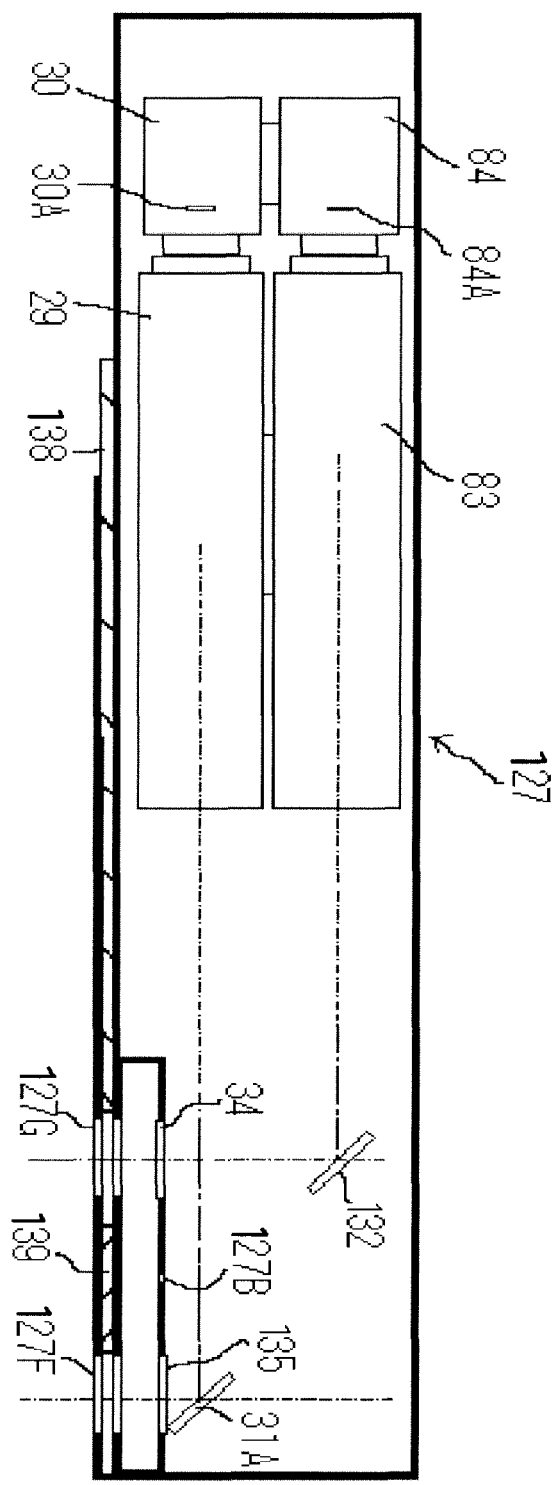
FIG. 40 is an end view of an imaging apparatus according to ninth embodiment.

Ninth embodiment of the imaging apparatus according to the present invention will be described using FIG. 40. However, substantially the same parts as those of the imaging apparatus 127 shown in FIG. 34 of the above-mentioned fifth embodiment are denoted by the same reference signs to omit or simplify the explanation thereof, and different parts will be mainly described. Ninth embodiment is an example where a pair of cameras are arranged on optical paths respectively corresponding to subjects at different imaging positions, as illustrated in FIG. 40.

In particular, the cameras 30, 84 and the imaging lens bodies 29, 83 are arranged in parallel, respectively. In addition, a pair of full mirrors 31A and 132 corresponding to the cameras 30 and 84 are arranged so as to face apertures 127F and 127G, respectively. The camera (including a CCD 84A which is an image pickup device) 84 images a subject in the whole-viewing area A through the imaging lens body 83 and the optical path of the full mirror 132. Meanwhile, the camera 30 images a subject in the whole-viewing area B through the imaging lens body 29 and the optical path of the full mirror 31A.

Here, in the present embodiment, a pair of the cameras 30 and 84 are provided, thereby eliminating the need of a focusing lens and making it possible to use a protective glass 135 instead. More specifically, in the present embodiment, focus adjustment is made for each of the cameras 30 and 84. The present embodiment is configured so as to make it possible to perform imaging with two series of optical paths, so that subjects in the whole-viewing area A and the whole-viewing area B can be imaged at the same time.

In addition, the present embodiment is an example where a pair of the shutters 138 and 139 are used, but may be configured such that only one shutter is used. In addition, if the whole-viewing area A and the whole-viewing area B are imaged at the same time, with high rigidity in couplings between the cameras 30 and 84 and the imaging lens bodies 29 and 83, the imaging will be equivalent to viewing the whole of the whole-viewing area A and the whole-viewing area B.

Tenth Embodiment

Tenth embodiment of the imaging apparatus according to the present invention will be described using FIG. 41. However, substantially the same parts as those of the imaging apparatus 127 shown in FIG. 40 of the above-mentioned ninth embodiment are denoted by the same reference signs to omit or simplify the explanation thereof, and different parts will be mainly described. Tenth embodiment is an example of respectively arranging a pair of cameras in different directions, for example, with either of the cameras rotated by 90 degrees, as illustrated in FIG. 41.

In particular, a pair of the cameras 30, 84 and the imaging lens bodes 29, 83 are fixed at both ends of a supporting body 85 having a substantially L-shaped plane, respectively. More specifically, the camera 30 and the imaging lens body 29 are horizontally coupled to an end 85A of the supporting body 85. The optical path between the camera 30 and one subject (for example, tool bit 24) is bent at a right angle by the mirror 31A, so that the subject is imaged in the range of one field of view area (whole-viewing area A).

Meanwhile, the camera 84 and the imaging lens body 83 are vertically coupled to an end 85B of the supporting body 85. The camera 84 (including the imaging lens body 83) is arranged in such a manner that the optical path between the camera and one subject (for example, tool bit 23) is in line, and images the subject in the range of one field of view area (whole-viewing area B). Furthermore, in the present embodiment, the optical paths between the subject and the respective imaging lens bodies have been set in advance to be at the same length.

Figure 41:
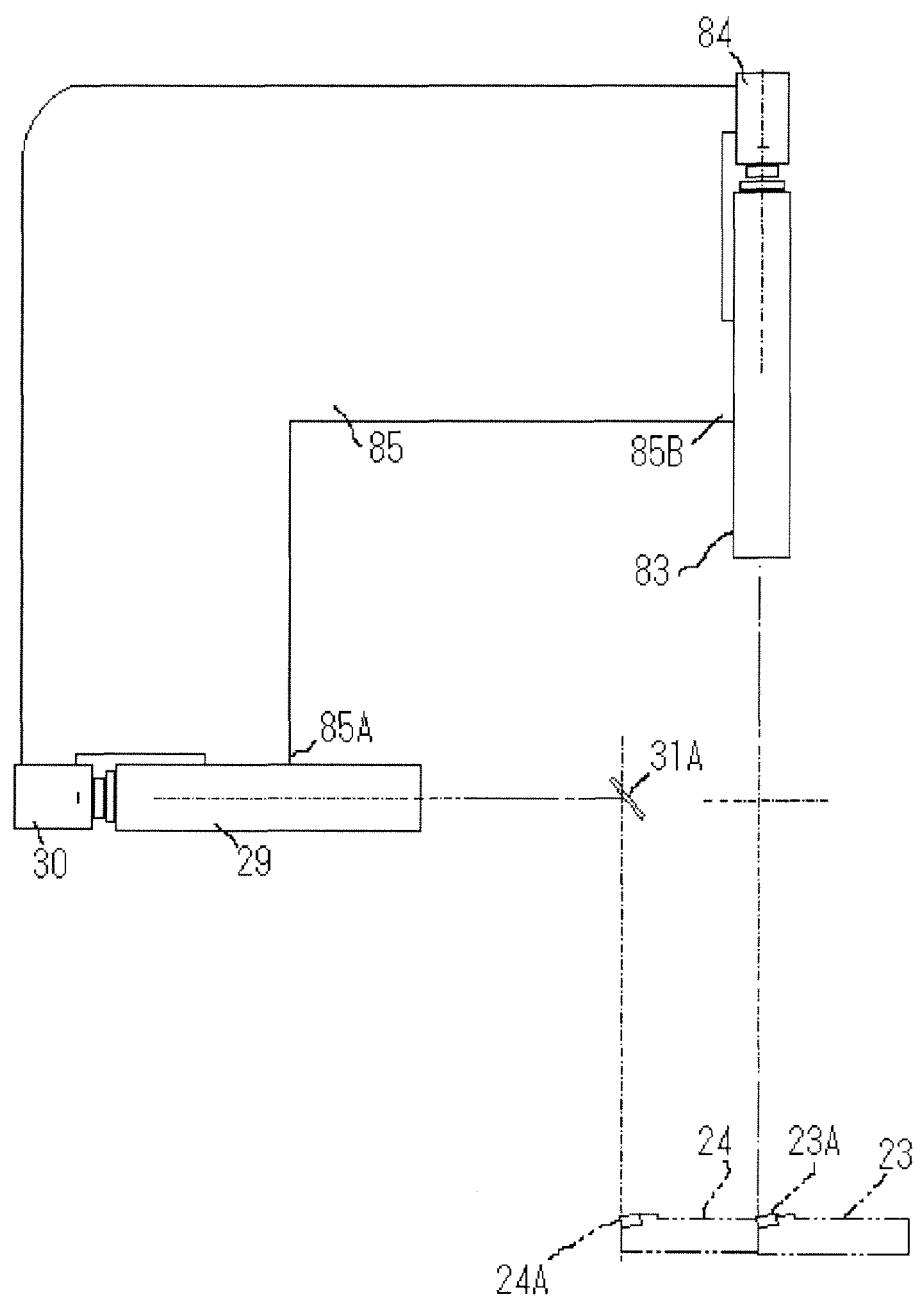
FIG. 41 is an end view of an imaging apparatus according to tenth embodiment.

It should be noted that the configuration of a shutter or the like is omitted in FIG. 41. In addition, if the supporting body 85 is manufactured with an invar with high rigidity in couplings between the cameras 30, 84 and the supporting body 85, there is no relative change due to the temperature of the cameras 30 and 84, and if the whole-viewing area A and the whole-viewing area B are imaged at the same time, the imaging will be equivalent to viewing the whole of the whole-viewing area A and the whole-viewing area B.

(Imaging State in Double-Spindle Face Lathe)

Here, an imaging state in the tool bit 26 arranged on the tool post 21, the reference gauge 18 arranged on the chuck 12, and the turret gauge 45 shown in FIG. 22 will be described using FIG. 42 and FIG. 43.

Figure 42:
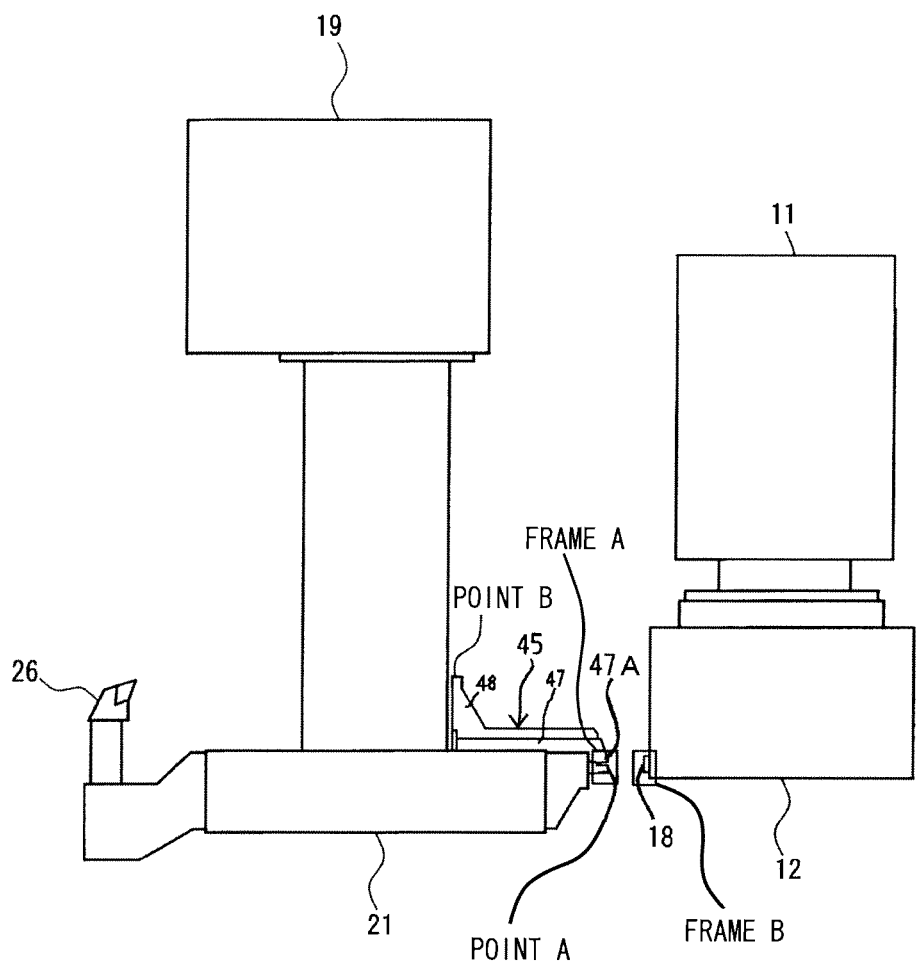
FIG. 42 is a view illustrating a measurement base point B of the turret gauge shown in FIG. 20 and a state of the field of view thereof.
Figure 43:
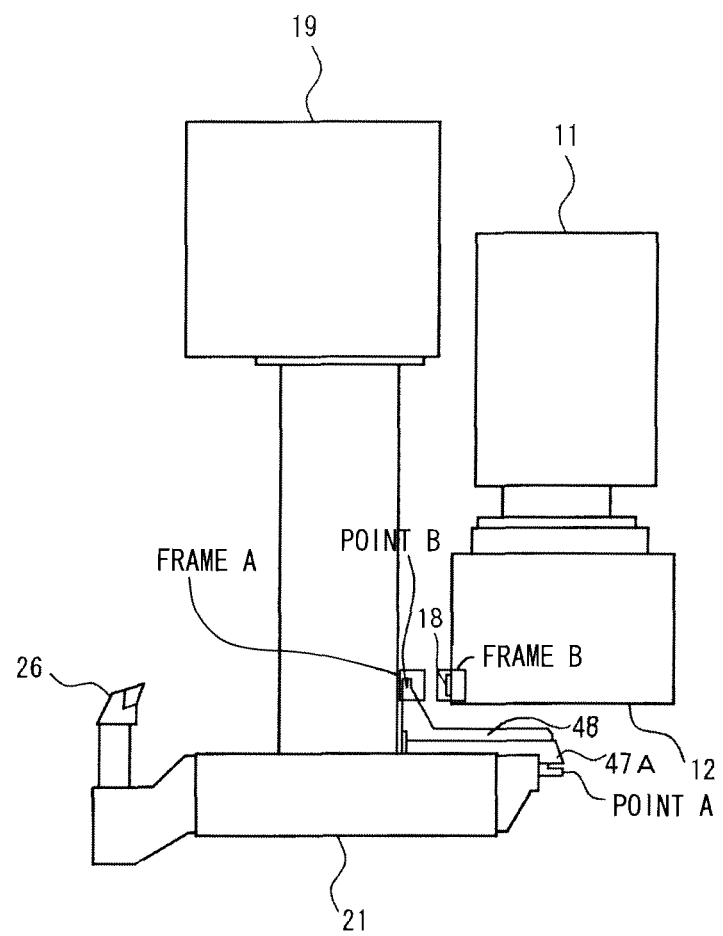
FIG. 43 is a view illustrating a measurement base point A of the turret gauge shown in FIG. 20 and a state of the field of view thereof.

For example, when imaging using the imaging apparatus 127 shown in FIG. 37, the reference gauge 18 fixed on the chuck 12 is imaged in the whole-viewing area B, and the point A of the gauge main body 48 and the leading edge 47A of the invar body 47 (or the tool bit 26) are imaged in the whole-viewing area A, as illustrated in FIG. 42. Meanwhile, as illustrated in FIG. 43, the reference gauge 18 fixed on the chuck 12 is imaged in the whole-viewing area B, and the point B of the gauge main body 48 (or the tool bit 26) is imaged in the whole-viewing area A. It should be noted that the frame A and the frame B shown in FIG. 42 and FIG. 43 correspond to in the ranges of the whole-viewing area A and the whole-viewing area B of the imaging apparatus 127 shown in FIG. 36, respectively.

(Variation of Chuck)

Hereinafter, a variation of a chuck will be described. However, substantially the same parts as those in the configuration of the chuck 12 shown in FIG. 36 of the above-mentioned fifth embodiment are denoted by the same reference signs to omit or simplify the explanation thereof, and different parts will be mainly described.

Figure 44:
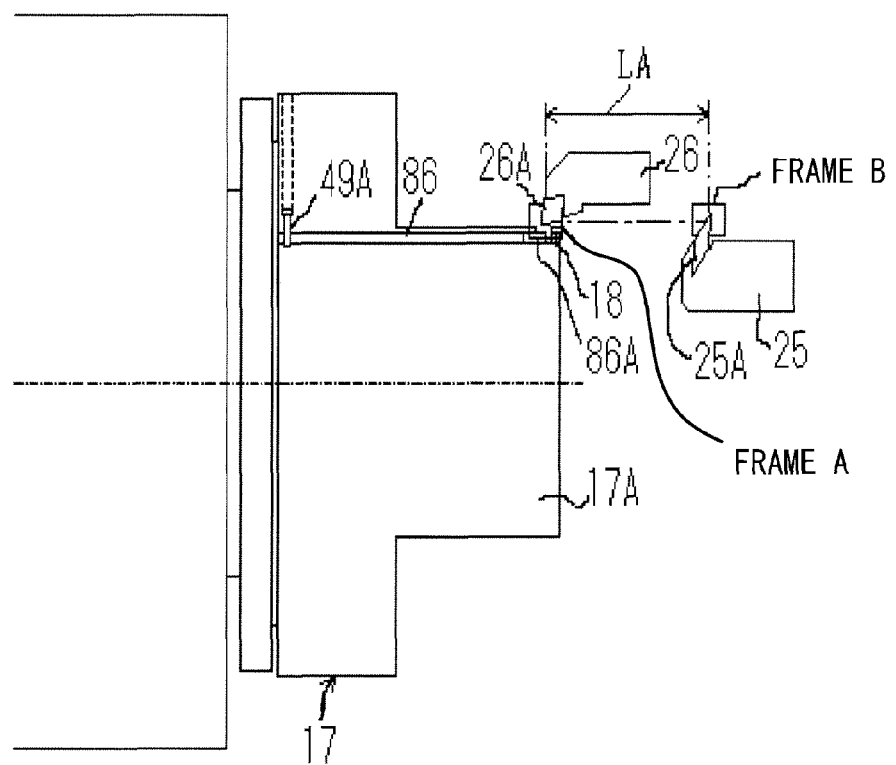
FIG. 44 is a view illustrating a variation of a chuck.
Figure 45:
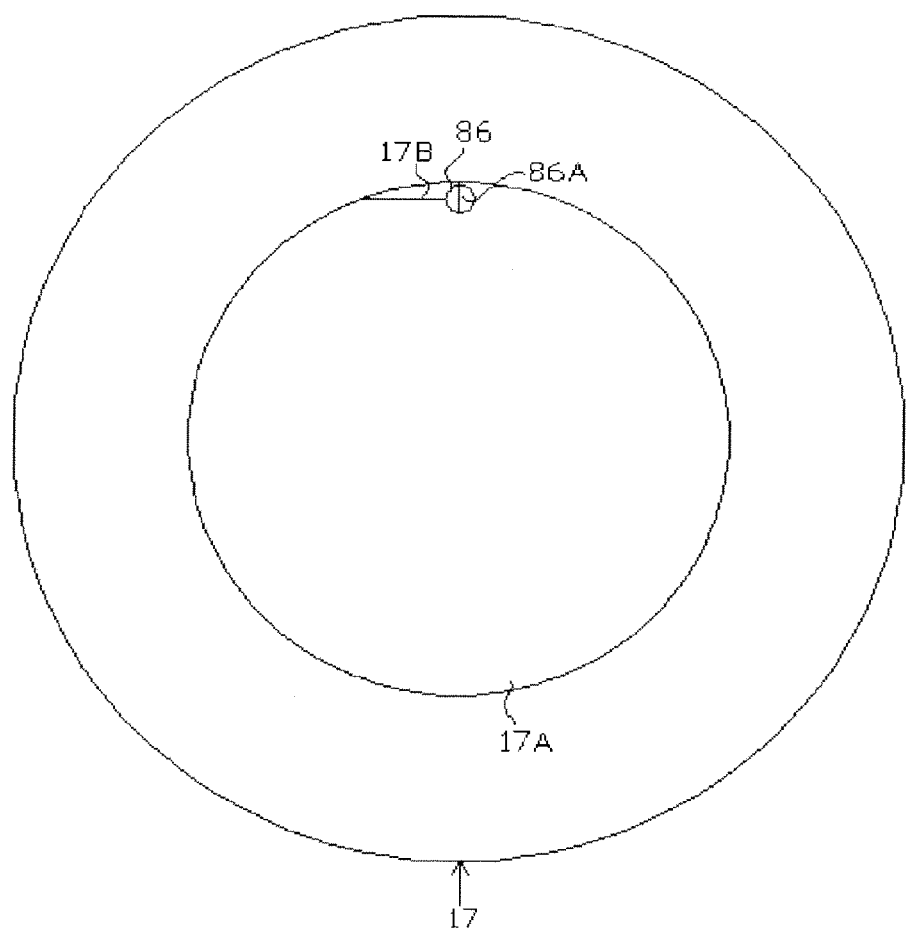
FIG. 45 is a side view of FIG. 44.

As illustrated FIG. 44 and in FIG. 45, the chuck 17 has a small-diameter section 17A constituting a leading edge. The chuck 17 also has a notch 17B (see FIG. 45) formed along the axis center direction of the chuck 17. This notch 17B is formed in the range from the outer periphery of the small-diameter section 17A to a large-diameter basal end (this portion is a "through hole"), as illustrated in FIG. 44.

In addition, the cylindrical invar body 86 has one end thereof fixed at a basal end of the chuck 17 by the bolt 49A which is a fastening member. A leading edge 86A of this invar body 86 has a semicircular shape, as illustrated in FIG. 45.

More specifically, as illustrated in FIG. 44, the leading edge 86A of the invar body 86, the reference gauge 18, and the chip 26A of the tool bit 26 are included and imaged in, for example, the field of view area (whole-viewing area A) of the imaging apparatus 127 shown in FIG. 37. It should be noted that when using the chuck 17 shown in FIG. 44, the invar body 86 can be arranged through the through hole of the chuck 17 even if the invar body 86 is a long one, and thus the long invar body 86 can be mounted on, for example, a collet chuck. In addition, the through hole of the invar body 86 is formed on the chuck 17, so that the need of a counterweight can be also eliminated.

Moreover, fifth to tenth embodiments may be configured in such a manner that the imaging apparatus 127 is made to be rotatable, and that the whole-viewing area A and the whole-viewing area B can be moved in a horizontal or vertical direction. In addition, the present invention is not limited to the double-spindle face lathe or the short spindle lathe which are illustrated in first to tenth embodiments, but is applicable to various types of cutting machines (machines which performs processing with a cutting tool and a workpiece moved relatively), such as a fraise or the like.

(Image Recognition Processing Method)

An image recognition processing method for a cutting tool according to the present embodiment will be described in detail using FIGS. 46 to 48.

(Technical Field)

This technical field relates to an image recognition processing method for recognizing an image of a subject such as a cutting tool and an image recognition processing method for a cutting tool.

(Background Art)

In the Patent Literature 1 mentioned above, a program for performing image processing and analysis using an image processing processor is stored in a program memory 65 (see paragraph [0052]), in order to repeatedly perform imaging using camera 20 to acquire images for 11 emission lines (11 frames) which are generated by performing a total of 11 times of projection and imaging (see paragraph [0072], FIG. 11 and FIG. 13). In Patent Literature 2, as mentioned above, at least either before or after processing an object to be processed, a tool is rotated or moved to capture multiple pieces of image data thereof, and image data in focus is selected and used from the multiple pieces of image data.

(Problem to be Solved)

In Patent Literature 1 and Patent Literature 2, the accuracy of recognizing a tool bit position during an image recognition process cannot be improved. More specifically, in Patent Literature 1 or Patent Literature 2, it is difficult to recognize a wear amount, a displacement amount, or the like of a tool bit with high accuracy by image recognition.

Meanwhile, in a camera of five million pixels, the X direction cutting line or the Z direction cutting line mentioned above is intended to obtain an important position which is to be a tangential line of a contour curve of a tool bit (tip curvature of a chip), and therefore position recognition accuracy is important. In a so-called multistep pattern matching (hereinafter, referred to as "MS") algorithm, even with low accuracy of position recognition of one seek line, the overall averaged accuracy is improved as more pieces of seek line data are obtained.

Given below are an image recognition processing method for improving position recognition accuracy of recognizing a subject such as a cutting tool by image recognition, and an image recognition processing method for a cutting tool.

In the above-mentioned image recognition processing method, at least one of a subject or an imaging means is relatively moved, and, with this travel amount set to a smaller value than a pixel (for example, one N (integer) th part of a pixel pitch), a recognition value based on image data is acquired, and a second averaged value calculated N times at an N (integer) th part of a pixel pitch is used as position data of the subject. Then, a standard deviation of the recognition value for the above-mentioned multiple times is calculated, the standard deviation is multiplied by a coefficient, and the multiplied value is added to or subtracted from the above-mentioned second averaged value, and the calculated value is used as, for example, cutting edge position data of the cutting tool.

Given above is a cutting machine using a numerical control system, which captures and processes images of a cutting tool using an imaging means both before and after cutting, which applies the image data to an image recognition processing method for detecting a state (deficit, expansion, wear, or heat displacement) of the cutting tool or a heat displacement amount of the cutting machine, and which corrects a processing position of the cutting tool based on the position data or the cutting edge position data of the subject such as the cutting tool.

(Method for Acquiring Position Data of Cutting Line)

Hereinafter, an image recognition processing method for a cutting tool will be described based on FIGS. 46 to 48. A method for acquiring position data of a cutting line moves the tool bit 26 shown in FIG. 36 in the Z direction by 1 μm, for example, eight times, images the tool bit 26 each time accordingly, and acquires the position data of the Z direction cutting line by the following method.

First, a position vector of the cutting line (an aggregate of a position Z and a position X) is calculated at a position of the tool bit 26. Next, a pitch of a seek line is set to 1 μm, and a seek line at which an edge position (an intersection between a seek line and a visible outline of a chip) is a maximal value (or may be a minimal value) is selected. Then, in order to enhance accuracy, the above-mentioned maximal value is set in the center (a position of the Z direction cutting line in FIG. 46), and an average value (ave) and a standard deviation (σ) at the edge positions of each 25 seek lines in the upper and lower sides (or right and left) are calculated. It should be noted that the total number of the seek lines in this case is 51.

Figure 46:
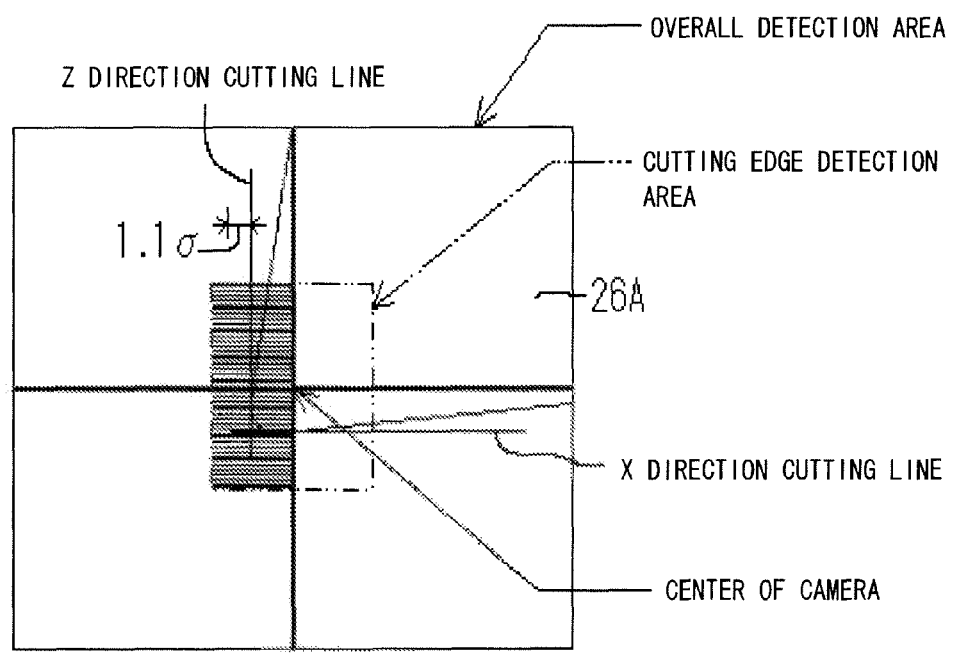
FIG. 46 is a view illustrating an inspection by a cutting tool.
Figure 46:
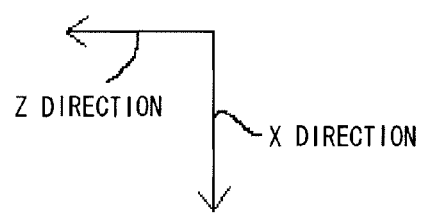

As illustrated in FIG. 46, when the chip 26A is protruded in a minus direction of the Z direction (or the X direction), a position (Cp) of the cutting line in the Z direction can be calculated by the following formula.

$$Cp = ave - 1.1\sigma$$

Here, when the chip 26A is protruded in a plus direction of the Z direction (or the X direction), the minus sign in the above-mentioned formula must be changed to a plus sign. In addition, the coefficient of 1.1 in the above-mentioned formula is a numeric value calculated based on an experimental value. Furthermore, a position of a cutting line in the X direction is also calculated by the procedure as mentioned above. Then, an accumulated value of a travel amount of the above-mentioned tool bit is subtracted from each calculated Cp value. Finally, a second averaged value for the above-mentioned data for eight times is calculated, and the position vector obtained by the above-mentioned second averaged value is calculated.

It should be noted that a pitch of moving a tool bit is measured N times at an N (integer) th part of a pixel pitch. For example, in the case where a side of a picture element (synonymous with pixel) is 8 μm, data is acquired 8 times at a feed pitch of an 8th part of the pixel, i.e., 1 μm, and position data is recorded as a second averaged value. More specifically, since the tool bit is moved at a pitch of an Nth part of one pixel, different image data can be acquired, so that image recognition accuracy can be improved. The tool bit may be moved at a pitch of, for example, a 4th part or a half of one pixel.

Here, the reason for moving the tool bit at an N (integer) th part of a pixel pitch is as follows. When image data is acquired using a smaller value than a pixel (for example, an N (integer) th part of a pixel pitch) as an travel amount, the after-mentioned nonlinear effect is exerted by the pixel, so that each data can be acquired as a separate image. According to experiment results, when one pixel (8.4 μm square) was used, recognition accuracy was improved from 2 μm for a single image data acquisition to 0.4 μm for an 8-time image data acquisition.

It should be noted that when image data is acquired multiple times by relatively moving a subject, for example, at least one of a tool bit or a camera, if a travel amount thereof is equal to, or integral times as large as, the size of a pixel, theoretically the same image data is to be acquired, and thus the amount of data does not practically increase. This is the same as when the same image data is acquired multiple times without moving a subject or the like. That is, useless operations are to be done in such a case.

(Nonlinear Effect of Pixel)

Figure 47:
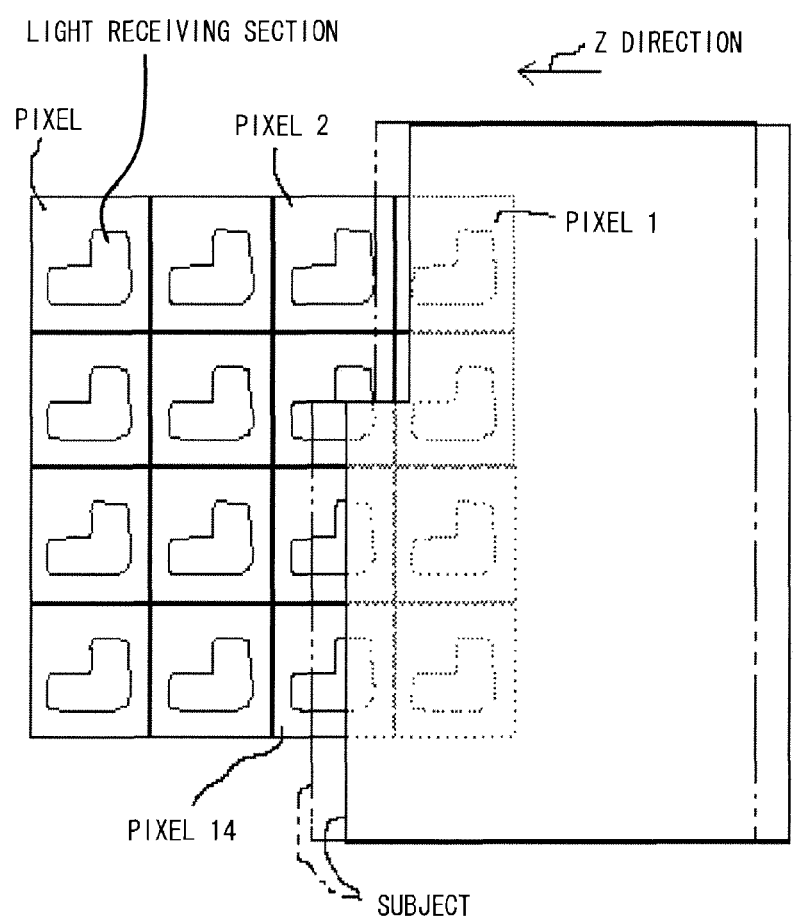
FIG. 47 is a view illustrating a processing state of image recognition.
Figure 48:
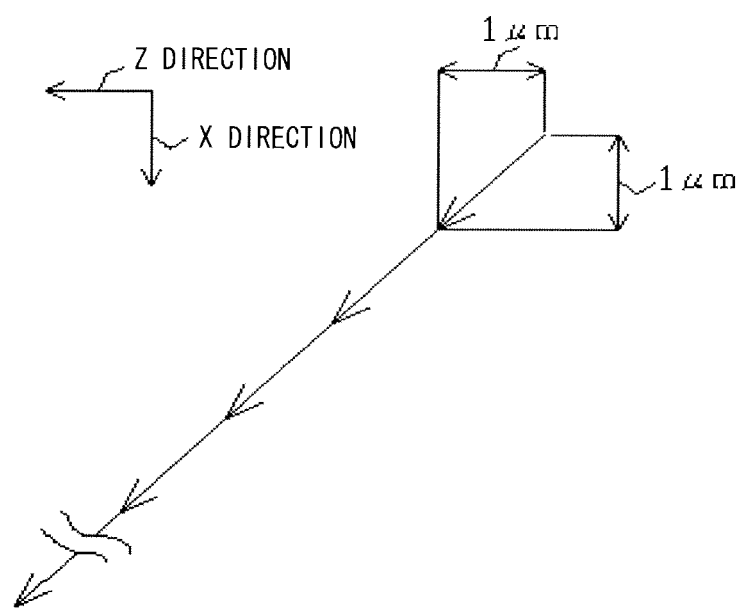
FIG. 48 is a view illustrating moving directions of a cutting tool.

As illustrated in FIG. 47, a light receiving section of a pixel has a substantially L-shaped form different from the outer shape, and as the amount of light received by this light receiving section changes, the amount of image data changes. Here, when a subject shown by a solid line is moved to a position shown by a chain double-dashed line, the amounts of light received by a pixel 1 and a pixel 2 do not change. Meanwhile, in a pixel 14, the subject moves on an L-shaped light receiving section area which is limited to a smaller area than a pixel, and therefore the amount of light received significantly changes at a higher ratio than the original one. More specifically, the change in the amount of light received of each pixel with respect to the movement of the subject becomes nonlinear. Therefore, when a subject is moved at an N (integer) th part of a pixel pitch, different image data can be acquired, so that image recognition accuracy can be improved.

In addition, FIG. 47 is a diagram of movement in the Z direction, but position data of the X direction cutting line may be acquired by moving a subject in the X direction. Furthermore, as illustrated in FIG. 48, the subject may be moved obliquely by 1 μm in the Z direction and the X direction. Moreover, the above-mentioned acquisition of the position data may be performed using an M (integral offset amount μm)+1 pixel as a travel amount of the subject. The travel amount may be, for example, 1+8=9 μm, 2+16=18 μm, 3+24=25 μm, 4+32=36 μm.

DESCRIPTION OF REFERENCE NUMERALS

12: Chuck
18: Reference gauge
21: Turret tool post (mounting table)
25: Inner diameter processing tool bit (cutting tool)
25A: Chip
26: Outer diameter processing tool bit (cutting tool)
26A: Chip
28: Camera apparatus (imaging means)
30: Camera
33A, 33B: Field of view
45, 46: Turret gauge (measuring means)
47, 86: Invar body (reference body)
47A, 86A: Leading edge of invar body
48: Gauge main body (object to be measured, mounting means)
60: CPU (collating means, calculating means, correcting means)
62: ROM (recording means)
64: RAM (recording means)
74: Bimetal body (measuring apparatus)
78, 79: Full mirror for folding back (folding back mirror means)
127: Imaging apparatus (imaging means)
138, 139: Shutter (switching means)
S: Lathe (cutting machine)
W: Workpiece

The invention claimed is:

1. A measuring apparatus comprising:
a reference body which is a reference of a heat displacement amount of a heat-displaced object to be measured;
an imaging means for imaging the reference body and the object to be measured in a same imaging area;
a recording means for recording reference image data at a reference temperature generated by the imaging means;
a central processing unit configured to
collate the reference image data, which has been recorded in advance in the recording means, with measured image data at a time of an arbitrary measurement, which is generated by the imaging means;

calculate difference values of dimensions of the reference body and the object to be measured at the time of the arbitrary measurement from dimensions of the reference body and the object to be measured at the reference temperature based on a collation result; and calculate a temperature of the object to be measured at the time of the arbitrary measurement.

2. The measuring apparatus according to claim 1, wherein the imaging means is one of a camera and an imaging apparatus, and the recording means is one of a read-only memory and a random-access memory.

3. A measuring method comprising:

imaging, as a subject, a reference body which is a reference of a heat displacement amount of a heat-displaced object to be measured in a same imaging area in an imaging means;

collating reference image data at a reference temperature, which has been recorded in advance in a recording means, with measured image data at a time of an arbitrary measurement by a collating means;

calculating difference values of dimensions of the reference body and the object to be measured at the time of the arbitrary measurement from dimensions of the reference body and the object to be measured at the reference temperature based on a collation result by the collating means; and measuring a temperature of the object to be measured at the time of the arbitrary measurement.

4. The measuring method according to claim 3, wherein the imaging means is one of a camera and an imaging apparatus, the recording means is one of a read-only memory and a random-access memory, and the collating means is a central processing unit.

5. An apparatus for correcting a processing position of a cutting machine comprising:

an imaging means for imaging a subject;

a reference gauge for measuring a position error of the imaging means;

a reference means, which is arranged on a mounting table where a cutting tool is to be mounted, for detecting a displacement amount of a cutting tool and a temperature of the mounting table;

a recording means for recording reference image data at a reference temperature, in which the reference gauge and the reference means corresponding to the reference gauge are imaged as a subject in a same imaging area by the imaging means;

a collating means for collating the reference image data, which has been recorded in advance in the recording means, with measured image data at a time of an arbitrary measurement of the subject, which is generated by the imaging means; and a correcting means for correcting a processing position of the cutting tool based on a collation result by the collating means, wherein the reference means comprises:

a mounting means which has an identical quality of material to that of a metal constituting the mounting table and has a reference section; and a reference body which has a free end fixed to only one end thereof and corresponding to the reference section, and which is a reference of a heat displacement amount of the mounting means, and wherein the reference body is formed with a material with a different thermal expansion coefficient from that of the metal constituting the mounting table.

6. The apparatus for correcting the processing position of the cutting machine according to claim 5, wherein the imaging means is one of a camera and an imaging apparatus, the reference means is a turret gauge, the recording means is one of a read-only memory and a random-access memory, the collating means is a central processing unit, the correcting means is the central processing unit, and the mounting means is a gauge main body.

7. An apparatus for correcting a processing position of a cutting machine comprising:

an imaging means for imaging a subject;

a reference gauge for measuring a position error of the imaging means;

a reference means, which is arranged on a mounting table where a cutting tool is to be mounted, for detecting a displacement amount of a cutting tool and a temperature of the mounting table;

a recording means for recording reference image data at a reference temperature, in which the reference gauge and the reference means corresponding to the reference gauge are imaged as a subject in a same imaging area by the imaging means;

a collating means for collating the reference image data, which has been recorded in advance in the recording means, with measured image data at a time of an arbitrary measurement of the subject, which is generated by the imaging means; and a correcting means for correcting a processing position of the cutting tool based on a collation result by the collating means, wherein the reference means comprises:

a mounting means which has an identical quality of material to that of a metal constituting the mounting table and has a reference section; and a reference body which has a free end fixed to only one end thereof and corresponding to the reference section, and which is a reference of a heat displacement amount of the mounting means, and wherein the reference body is a bimetal body.

8. The apparatus for correcting the processing position of the cutting machine according to claim 7, wherein the imaging means is one of a camera and an imaging apparatus, the reference means is a turret gauge, the recording means is one of a read-only memory and a random-access memory, the collating means is a central processing unit, the correcting means is the central processing unit, and the mounting means is a gauge main body.

9. An apparatus for correcting a processing position of a cutting machine, comprising:

an imaging means for imaging a subject;

a reference gauge which is arranged on a chuck for holding a workpiece in order to measure a position error of the imaging means;

a reference body which is arranged in such a manner that one end is fixed to the chuck and that a free end corresponds to the reference gauge, and which is a reference of a heat displacement amount of the reference gauge;

a recording means for recording reference image data at a reference temperature, which is obtained by imaging, as a subject, the reference gauge and the free end of the reference body corresponding to the reference gauge in a same imaging area by the imaging means;

a collating means for collating the reference image data, which has been recorded in advance in the recording means, with measured image data at a time of an arbitrary measurement of the subject, which is generated by the imaging means; and a correcting means for correcting a processing position of a cutting tool based on a collation result by the collating means, wherein the reference body is a material with a different thermal expansion coefficient from that of the material holding the reference gauge.

10. The apparatus for correcting the processing position of the cutting machine according to claim 9, wherein the imaging means is one of a camera and an imaging apparatus, the recording means is one of a read-only memory and a random-access memory, the collating means is a central processing unit, and the correcting means is the central processing unit.

11. An apparatus for correcting a processing position of a cutting machine, comprising:
an imaging means for imaging a subject;
a reference gauge which is arranged on a chuck for holding a workpiece in order to measure a position error of the imaging means;
a reference body which is arranged in such a manner that one end is fixed to the chuck and that a free end corresponds to the reference gauge, and which is a reference of a heat displacement amount of the reference gauge;
a recording means for recording reference image data at a reference temperature, which is obtained by imaging, as a subject, the reference gauge and the free end of the reference body corresponding to the reference gauge in a same imaging area by the imaging means;
a collating means for collating the reference image data, which has been recorded in advance in the recording means, with measured image data at a time of an arbitrary measurement of the subject, which is generated by the imaging means; and
a correcting means for correcting a processing position of a cutting tool based on a collation result by the collating means, wherein the reference body is a bimetal body.

12. The apparatus for correcting the processing position of the cutting machine according to claim 11, wherein the imaging means is one of a camera and an imaging apparatus, the recording means is one of a read-only memory and a random-access memory, the collating means is a central processing unit, and the correcting means is the central processing unit.

13. An imaging apparatus comprising:
an optical path separating means for separating an optical path respectively corresponding to a subject at a different imaging position; and
an image pickup device which is arranged on a same optical path in the optical path separating means,
wherein the optical path separating means blocks an optical path at one imaging position, when imaging the subject at the other imaging position,
wherein one of the optical path separating means is a half mirror, and the other is a full mirror, and
wherein an optical path is folded back to the half mirror so as to be of the same length as that of an optical path of the full mirror.

14. The imaging apparatus according to claim 13, wherein the optical path separating means is a mirror.

* * * * *